(12) United States Patent
Frank et al.

(10) Patent No.: US 7,829,568 B2
(45) Date of Patent: Nov. 9, 2010

(54) SUBSTITUTED 5,6,7,8-TETRAHYDROIMIDAZO[1,2-A]PYRIDIN-2-YLAMINE COMPOUNDS AND THEIR USE FOR PRODUCING DRUGS

(75) Inventors: Robert Frank, Aachen (DE); Bernd Sundermann, Aachen (DE); Corinna Sundermann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 459 days.

(21) Appl. No.: 11/868,273

(22) Filed: Oct. 5, 2007

(65) Prior Publication Data

US 2008/0300256 A1 Dec. 4, 2008

Related U.S. Application Data

(63) Continuation of application No. PCT/EP2006/003153, filed on Apr. 7, 2006.

(30) Foreign Application Priority Data

Apr. 8, 2005 (DE) .................. 10 2005 016 547

(51) Int. Cl.
 A61K 31/437 (2006.01)
 A61K 31/497 (2006.01)
 C07D 471/04 (2006.01)
 C07D 401/02 (2006.01)
 A61P 3/04 (2006.01)
 A61P 25/06 (2006.01)
 A61P 25/24 (2006.01)
 A61P 25/28 (2006.01)

(52) U.S. Cl. .................. 514/253.04; 514/300; 546/121; 544/362

(58) Field of Classification Search ............ 514/253.04, 514/300; 546/121; 544/362
 See application file for complete search history.

(56) References Cited

U.S. PATENT DOCUMENTS

| 5,420,138 A | 5/1995 | Corbier et al. |
| 2002/0183327 A1 | 12/2002 | Gerlach et al. |
| 2003/0022914 A1 | 1/2003 | Maul et al. |
| 2004/0204409 A1 | 10/2004 | Ando et al. |
| 2007/0004736 A1 | 1/2007 | Kubo et al. |

FOREIGN PATENT DOCUMENTS

| EP | 0 556 080 A1 | 8/1993 |
| WO | WO 01/53298 A1 | 7/2001 |
| WO | WO 01/72748 A1 | 10/2001 |
| WO | WO 02/081475 A1 | 10/2002 |
| WO | WO 2004/024074 A2 | 3/2004 |
| WO | WO 2004/048363 A1 | 6/2004 |
| WO | WO 2004/074290 A1 | 9/2004 |
| WO | WO 2004/089366 A1 | 10/2004 |

OTHER PUBLICATIONS

Paetzel et al., Liebigs Annalen der Chemie (1991), (9), pp. 975-978.*
International Preliminary Report on Patentability (English Translation) Nine (9) pages.
International Search Report dated Aug. 3, 2006 with English translation of relevant portion and PCT/ISA/237 (Eleven (11) pages).
German Search Report dated Dec. 29, 2005 with English translation of relevant portion (Nine (9) pages).
E. G. Gray, et al., "The Isolation of Nerve Endings from Brain; An Electron-Microscopic Study of Cell Fragments Derived by Homogenization and Centrifugation", Department of Anatomy, University College London, and the Biochemistry Department, Agricultural Research Council Institute of Animal Physiology, Babraham, Cambridge, pp. 79-96, vol. 96, Part 1.
Louis J Ravin, "Preformulation" Pharmaceutics Department, SmithKline Beckman Corporation, pp. 1409-1423, Chapter 76.
Anthony R. Disanto, "Bioavailability and Bioequivalency Testing", Clinical Biopharmaceutics/New Formulation Development, The Upjohn Company, pp. 1424-1431, Chapter 77.
Adelbert M. Knevel, "Separation", Purdue University: School of Pharmacy and Pharmacal Sciences, pp. 1432-1442, Chapter 78.
G. Briggs Phillips, "Sterilization", Health Industries Manufacturers Association, pp. 1443-1454, Chapter 79.
Frederick P. Siegel, "Tonicity, Osmoticity, Osmolality and Osmolarity", College of Pharmacy, University of Illinois, pp. 1455-1472, Chapter 80.
Robert L. Giles, et al., "Plastic Packaging Materials", Glenn Beall Engineering, Inc. et al, pp. 1473-1477, Chapter 81.
Carl J. Lintner, "Stability of Pharmaceutical Products", Lintner Associates, pp. 1478-1486, Chapter 82.
Clyde R. Erskine, Jr., "Quality Assurance and Control", SmithKline Beckman Corporation, pp. 1487-1491, Chapter 83.

(Continued)

Primary Examiner—D. Margaret Seaman
Assistant Examiner—Niloofar Rahmani
(74) Attorney, Agent, or Firm—Crowell & Moring LLP

(57) ABSTRACT

Substituted 5,6,7,8-tetrahydro-imidazo[1,2-a]pyridin-2-ylamine compounds corresponding to formula I, methods for the preparation thereof, pharmaceutical compositions containing said compounds, the use of said compounds for preparing pharmaceutical compositions and related treatment methods.

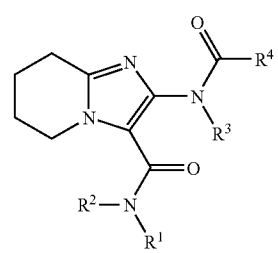

25 Claims, No Drawings

OTHER PUBLICATIONS

J. G. Nairn, "Solutions, Emulsions, Suspensions and Extractives", Faculty of Pharmacy, University of Toronto, pp. 1492-1517, Chapter 84.

Kenneth E. Avis, "Parenteral Preparations", College of Pharmacy, University of Tennessee Center for the Health Sciences, pp. 1518-1541, Chapter 85.

Salvatore J. Turco, et al., "Intravenous Admixtures", Temple University School of Pharmacy et al., pp. 1542-1552, Chapter 86.

John D. Mullins, "Ophthalmic Preparations", Alcon Laboratories: Research and Development, pp. 1553-1566, Chapter 87.

Lawrence H. Block, "Medicated Applications", Duquesne University School of Pharmacy, pp. 1567-1584, Chapter 88.

Edward G. Ripple, "Powders", University of Minnesota: College of Pharmacy, pp. 1585-1602, Chapter 89.

Robert E. King et al., "Oral Solid Dosage Forms", Philadelphia College of Pharmacy and Science, pp. 1603-1632, Chapter 90.

Stuart C. Porter, "Coating of Pharmaceutical Dosage Forms", Colorcon, Inc., pp. 1633-1643, Chapter 91.

Mark A. Longer et al., "Sustained-Release Drug Delivery Systems", University of Wisconsin: School of Pharmacy, pp. 1644-1661, Chapter 92.

John J. Sclarra et al., "AEROSOLS", Arnold & Marie Schwartz College of Pharmacy and Health Sciences, pp. 1662-1677, Chapter 93.

M. Sako, "Product Class 18:Pyridopyridazines", Science of Synthesis: Houben-Weyl, Methods of Molecular Transformations, 2004, pp. 1109-1112, and 1115-1153, Category 2, vol. 16, Georg Theime Verlag, New York.

Akimori Wada et al., "Synthesis of Pyrido [4,3-$d$] pyrimidin-5(6$H$)-ones via Anionic Cycloaddition of Methyl 2,4-Dimethoxy-6-methyl-5-pyrimidinecarboxylate with Imines", Chem. Pharm. Bull., May 1991, pp. 1189-1192, vol. 39, No. 5, 1991 Pharmaceutical Society of Japan.

Hiroki Takahata et al., "Reaction of Lactim Ethers with 2-Caebethoxymethyl Piperidines", Abstracts of Papers 12th Congress of Heterocyclic Chemistry, Oct. 22, 1979, pp. 296-300, Tokyo, Japan.

* cited by examiner

SUBSTITUTED 5,6,7,8-TETRAHYDROIMIDAZO[1,2-A]PYRIDIN-2-YLAMINE COMPOUNDS AND THEIR USE FOR PRODUCING DRUGS

CROSS REFERENCE TO RELATED APPLICATIONS

This application is a continuation of International Patent Application No. PCT/EP2005/003153, filed Apr. 7, 2006, designating the United States of America, and published in German as WO 2006/105971 A1, the entire disclosure of which is incorporated herein by reference. Priority is claimed based on German Patent Application No. 10 2005 016 547.8 filed Apr. 8, 2005.

FIELD OF THE INVENTION

The present invention relates to substituted 5,6,7,8-tetrahydro-imidazo[1,2-a]pyridin-2-ylamine compounds, to methods for their preparation, to pharmaceutical compositions containing these compounds and to the use of said compounds for preparing pharmaceutical compositions.

BACKGROUND OF THE INVENTION

The treatment of pain, in particular neuropathic pain, is of great importance in the field of medicine. There is a worldwide need for effective methods of treating pain. The urgent need for action for patient-oriented and purposeful treatment of chronic and non-chronic pain conditions, this being taken to mean the successful and satisfactory treatment of pain for the patient, is also documented in the large number of scientific papers which have recently appeared in the field of applied analgesics and fundamental research work on nociception.

A suitable starting point for treating pain, in particular neuropathic pain, is the vanilloid receptor, subtype 1 (VR1/TRPV1), which is frequently also referred to as the capsaicin receptor. Said receptor is stimulated inter alia by vanilloids such as capsaicin, heat and protons and is central to the generation of pain. In addition, it plays a significant role in a large number of further physiological and pathophysiological processes, such as migraine; depression; neurodegenerative diseases; cognitive diseases; states of anxiety; epilepsy; coughs; diarrhoea; pruritus; cardiovascular system disorders; eating disorders; medicine dependency; medicine abuse and in particular urinary incontinence.

SUMMARY OF THE INVENTION

One object of the present invention is to provide new compounds suitable in particular as pharmacological active ingredients in pharmaceutical compositions, preferably in pharmaceutical compositions for the treatment of disorders or diseases mediated at least in part by vanilloid receptors 1 (VR1/TRPV1 receptors).

Surprisingly, it has been found that substituted 5,6,7,8-tetrahydro-imidazo[1,2-a]pyridin-2-ylamine compounds of the following general formula I have a marked affinity for the vanilloid receptor, subtype 1 (VR1/TRPV1 receptor) are thus particularly suitable for the prophylaxis and/or treatment of disorders or diseases mediated at least in part by vanilloid receptors 1 (VR1/TRPV1).

The present invention therefore relates to substituted 5,6,7,8-tetrahydro-imidazo[1,2-a]pyridin-2-ylamine compounds of the general formula I,

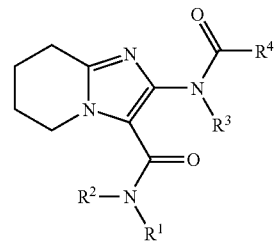

in which
$R^1$ and $R^2$, independently of one another, each represent
a hydrogen radical;
$C(=O)-OR^5$;
$-(CHR^6)-(CH_2)_m-C(=O)-OR^7$ in which m=0, 1, 2, 3, 4 or 5;
$-C(=O)-R^8$;
$-(CH_2)_n-C(=O)-R^9$ in which n=1, 2, 3, 4 or 5;
$C(=O)-NH-R^{10}$;
$-(CH_2)_o-C(=O)-NHR^{11}$ in which o=0, 1, 2, 3, 4 or 5;
$-C(=O)-NR^{12}R^{13}$;
$-(CH_2)_p-C(=O)-NR^{14}R^{15}$ in which p=1, 2, 3, 4 or 5;
$-(CHR^{16})-X_q-(CHR^{17})_r-Y_s-(CHR^{18})_t-Z_u-R^{19}$
in which q=0 or 1, r=0 or 1, s=0 or 1, t=0 or 1, u=0 or 1 and in which X, Y and Z, independently of one another, each represent O, S, NH, N(CH_3), N(C_2H_5) or N[CH(CH_3)_2];
a linear or branched, saturated or unsaturated, optionally substituted $C_{1-10}$ aliphatic radical;
a saturated or unsaturated, optionally substituted 3-, 4-, 5-, 6-, 7-, 8- or 9-membered cycloaliphatic radical which may be bridged with a linear or branched, optionally substituted $C_{1-5}$ alkylene group and/or condensed with a saturated, unsaturated or aromatic, optionally substituted monocyclic or polycylic ring system;
or an optionally substituted 5- to 14-membered aryl or heteroaryl radical which may be condensed with a saturated or unsaturated, optionally substituted monocyclic or polycyclic ring system;
or
$R^1$ and $R^2$, together with the nitrogen atom which binds them as the ring member, form a saturated or unsaturated, optionally substituted 4-, 5-, 6-, 7-, 8- or 9-membered heterocycloaliphatic radical, which can be condensed with a saturated, unsaturated or aromatic, optionally substituted monocyclic or polycyclic ring system and/or, together with a saturated or unsaturated, optionally substituted 5, 6 or 7-membered cycloaliphatic radical, can form an optionally substituted spiro compound via a common ring atom,
in which the respective heterocycloaliphatic radical and optionally the cycloaliphatic radical of the spiro compound may be substituted with 1, 2, 3, 4 or 5 substituents selected independently of one another from the group consisting of $R^{20}$, $-(CHR^{21})-(CH_2)_v-(CH_2)_w-R^{22}$ in which v=0 or 1 and w=0 or 1, $-CH=CH-R^{23}$, $-(CH_2)_x-C(=O)-OR^{24}$ in which x=0, 1, 2, 3, 4 or 5; $-(CH_2)_y-C(=O)-R^{25}$ in which y=0, 1, 2, 3, 4 or 5; $-(CH_2)_z-C(=O)-NHR^{26}$ in which z=0, 1, 2, 3, 4 or 5; $-(CH_2)_{aa}-C(=O)-NR^{27}R^{28}$ in which aa=0, 1, 2, 3, 4 or 5; F; Cl; Br; $-CN$; $-CF_3$; $-NO_2$; oxo $(=O)$; thioxo $(=S)$; $-C_{1-5}$-alkyl; $-OH$; $-O-C_{1-5}$-alkyl; $-SH$; $-S-C_{1-5}$-alkyl; $-NH_2$; $NH-C_{1-5}$ alkyl and $-N(C_{1-5}$-alkyl$)_2$ and/or may each have a further 1, 2, 3, 4 or 5 heteroatom(s) as the ring member(s) selected independently of one another from the group consisting of oxygen, nitrogen and sulphur;

$R^3$ represents a hydrogen radical;
- a linear or branched, saturated or unsaturated, optionally substituted $C_{1-10}$ aliphatic radical,
- a saturated or unsaturated, optionally substituted 3-, 4-, 5-, 6-, 7-, 8- or 9-membered cycloaliphatic radical which may be bound by a linear or branched, optionally substituted $C_{1-5}$ alkylene, $C_{2-5}$ alkenylene or $C_{2-5}$ alkynylene group,
- or an optionally substituted 5- to 14-membered aryl or heteroaryl radical which may be condensed with a saturated or unsaturated, optionally substituted monocyclic or polycyclic ring system and/or may be bound by a linear or branched, optionally substituted $C_{1-5}$ alkylene, $C_{2-5}$ alkenylene or $C_{2-5}$ alkynylene group;

$R^4$ represents a linear or branched, saturated or unsaturated, optionally substituted $C_{1-10}$ aliphatic radical,
- a saturated or unsaturated, optionally substituted 3-, 4-, 5-, 6-, 7-, 8- or 9-membered cycloaliphatic radical which may be bound by a linear or branched, optionally substituted $C_{1-5}$ alkylene, $C_{2-5}$ alkenylene or $C_{2-5}$ alkynylene group,
- or an optionally substituted 5- to 14-membered aryl or heteroaryl radical which may be condensed with a saturated or unsaturated, optionally substituted monocyclic or polycyclic ring system and/or may be bound by a linear or branched, optionally substituted $C_{1-5}$ alkylene, $C_{2-5}$ alkenylene or $C_{2-5}$ alkynylene group;

$R^5, R^7, R^8, R^9, R^{10}, R^{11}, R^{12}, R^{13}, R^{14}, R^{15}, R^{24}, R^{25}, R^{26}, R^{27}$ and $R^{28}$, independently of one another, each represent
- a linear or branched, saturated or unsaturated, optionally substituted $C_{1-10}$ aliphatic radical,
- an unsaturated or saturated, optionally substituted 3-, 4-, 5-, 6-, 7-, 8- or 9-membered cycloaliphatic radical which may be condensed with a saturated, unsaturated or aromatic, optionally substituted monocyclic or polycyclic ring system and/or may be bound by a linear or branched, optionally substituted $C_{1-5}$ alkylene, $C_{2-5}$ alkenylene or $C_{2-5}$ alkynylene group,
- or an optionally substituted 5- to 14-membered aryl or heteroaryl radical which may be condensed with a saturated or unsaturated, optionally substituted monocyclic or polycylic ring system and/or may be bound by a linear or branched, optionally substituted $C_{1-5}$ alkylene, $C_{2-5}$ alkenylene or $C_{2-5}$ alkynylene group;

$R^6$ represents a hydrogen radical;
- a linear or branched, saturated or unsaturated, optionally substituted $C_{1-10}$ aliphatic radical, which may have 1, 2, 3, 4 or 5 heteroatom(s) as the chain link(s) selected from the group consisting of oxygen, sulphur and nitrogen;
- or an optionally substituted 5- to 14-membered aryl or heteroaryl radical which may be condensed with a saturated or unsaturated, optionally substituted monocyclic or polycylic ring system and/or may be bound by a linear or branched, optionally substituted $C_{1-5}$ alkylene, $C_{2-5}$ alkenylene or $C_{2-5}$ alkynylene group;

$R^{16}, R^{17}$ and $R^{18}$, independently of one another, each represent
- a hydrogen radical;
- a linear or branched, saturated or unsaturated, optionally substituted $C_{1-10}$ aliphatic radical, which may have 1, 2, 3, 4 or 5 heteroatom(s) as the chain link(s) selected independently of one another from the group consisting of oxygen, sulphur and nitrogen;
- or an optionally substituted 5- to 14-membered aryl or heteroaryl radical which may be condensed with a saturated or unsaturated, optionally substituted monocyclic or polycyclic ring system;

$R^{19}$ represents an unsaturated or saturated, optionally substituted 3-, 4-, 5-, 6-, 7-, 8- or 9-membered cycloaliphatic radical which may be bridged with 1, 2, 3, 4 or 5 linear or branched, optionally substituted $C_{1-5}$ alkylene groups and/or condensed with a saturated, unsaturated or aromatic, optionally substituted monocyclic or polycylic ring system;
- or an optionally substituted 5- to 14-membered aryl or heteroaryl radical which may be condensed with a saturated or unsaturated, optionally substituted monocyclic or polycyclic ring system;

$R^{20}$ represents a linear or branched, saturated or unsaturated, optionally substituted $C_{1-10}$ aliphatic radical;
- an unsaturated or saturated, optionally substituted 3-, 4-, 5-, 6-, 7-, 8- or 9-membered cycloaliphatic radical;
- or an optionally substituted 5- to 14-membered aryl or heteroaryl radical which may be condensed with a saturated or unsaturated, optionally substituted monocyclic or polycylic ring system;

$R^{21}$ represents a hydrogen radical;
- a linear or branched, saturated or unsaturated, optionally substituted $C_{1-10}$ aliphatic radical;
- an unsaturated or saturated, optionally substituted 3-, 4-, 5-, 6-, 7-, 8- or 9-membered cycloaliphatic radical;
- or an optionally substituted 5- to 14-membered aryl or heteroaryl radical which may be condensed with a saturated or unsaturated, optionally substituted monocyclic or polycylic ring system;

and $R^{22}$ and $R^{23}$, independently of one another, each represent
- an unsaturated or saturated, optionally substituted 3-, 4-, 5-, 6-, 7-, 8- or 9-membered cycloaliphatic radical;
- or an optionally substituted 5- to 14-membered aryl or heteroaryl radical which may be condensed with a saturated or unsaturated, optionally substituted monocyclic or polycylic ring system;

in which the aforementioned $C_{1-10}$ aliphatic radicals may optionally each be substituted with 1, 2, 3, 4 or 5 substituents selected independently of one another from the group consisting of F, Cl, Br, I, —CN, —NO$_2$, —OH, —SH and —NH$_2$;

the aforementioned cycloaliphatic radicals may optionally each be substituted with 1, 2, 3, 4 or 5 substituents selected independently of one another from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —(CH$_2$)-benzo[b]furanyl, —O-phenyl, —O-benzyl, phenyl and benzyl, in which the respective cyclic portion of the —O-phenyl, —O-benzyl, phenyl, —(CH$_2$)-benzo[b]furanyl and benzyl radicals may be substituted with 1, 2, 3, 4 or 5 substituents selected independently of one another from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl and the aforementioned cycloaliphatic radicals may optionally each have 1, 2, 3, 4 or 5 heteroatom(s) as the ring member(s) selected independently of one another from the group consisting of oxygen, nitrogen and sulphur;

the aforementioned $C_{1-5}$ alkylene, $C_{2-5}$ alkenylene or $C_{2-5}$ alkynylene groups may optionally each be substituted with 1, 2, 3, 4 or 5 substituents selected independently of one another from the group consisting of F, Cl, Br, —OH, —SH, —NH$_2$, —CN, NO$_2$ and phenyl;

the rings of the aforementioned monocyclic or polycyclic ring systems may optionally each be substituted with 1, 2, 3, 4 or 5 substituents selected independently of one another from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —(CH$_2$)— benzo[b]furanyl, —O-phenyl, —O-benzyl, phenyl and benzyl, in which the respective cyclic portion of the —O-phenyl, —O-benzyl, phenyl, —(CH$_2$)-benzo[b]furanyl and benzyl radicals may be substituted with 1, 2, 3, 4 or 5 substituents selected independently of one another from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl and the rings of the aforementioned monocyclic or polycylic ring systems each have 5, 6, or 7 members and may optionally each have 1, 2, 3, 4 or 5 heteroatom(s) as the ring member(s) selected independently of one another from the group consisting of oxygen, nitrogen and sulphur;

and the aforementioned aryl or heteroaryl radicals may optionally each be substituted with 1, 2, 3, 4 or 5 substituents selected independently of one another from the group consisting of F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —NH—C(=O)—O—C$_{1-5}$-alkyl, —C(=O)—H, —C(=O)—C$_{1-5}$-alkyl, —C(=O)—NH$_2$, —C(=O)—NH—C$_{1-5}$-alkyl, C(=O)—N—(C$_{1-5}$-alkyl)$_2$, —(CH$_2$)-benzo[b]furanyl, —O-phenyl, —O-benzyl, phenyl and benzyl in which the respective cyclic portion of the —O-phenyl, —O-benzyl, phenyl, —(CH$_2$)-benzo[b]furanyl and benzyl radicals may be substituted with 1, 2, 3, 4 or 5 substituents selected independently of one another from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl and the aforementioned heteroaryl radicals may optionally each have 1, 2, 3, 4 or 5 heteroatom(s) as the ring member(s) selected independently of one another from the group consisting of oxygen, nitrogen and sulphur;

each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In the context of the present invention, "monocyclic or polycylic ring system" is to be understood as monocyclic or polycylic hydrocarbon radicals which are saturated, unsaturated or aromatic and may optionally have 1, 2, 3, 4 or 5 heteroatoms as ring members selected, independently of one another, from the group consisting of oxygen, nitrogen and sulphur. A monocyclic or polycyclic ring system of this type may be condensed (annelated) with a cycloaliphatic radical, an aryl radical or a heteroaryl radical.

Provided a polycyclic ring system is present, for example a bicyclic ring system, the various cycles, independently of one another may each have different degrees of saturation, i.e. they may be saturated, unsaturated or aromatic. A polycyclic ring system is preferably a bicyclic ring system.

In the context of the present invention, aliphatic radicals include saturated alkyl radicals and also unsaturated alkenyl radicals with at least a C=C double bond and unsaturated alkynyl radicals with at least a CC triple bond. Examples of aliphatic radicals include methyl, ethyl, n-propyl, isopropyl, n-butyl, isobutyl, sec-butyl, tert-butyl, n-pentyl, sec-pentyl, 2-pentyl, 3-pentyl, isopentyl, neopentyl, n-hexyl, 2-hexyl, 3-hexyl, n-heptyl, n-octyl, n-nonyl, n-decyl, —C(H)(C$_2$H$_5$)$_2$, —C(H)(CH$_3$)—C(H)(CH$_3$)$_2$, —(CH$_2$)—(CH$_2$)—C(CH$_3$)$_3$, —C(H)(n-C$_3$H$_7$)$_2$, —CH$_2$—CH$_2$—C(H)(CH$_3$)—(CH$_2$)$_3$—CH$_3$, vinyl, ethynyl, 1-propenyl, 2-propenyl, 1-propynyl, 2-propynyl, 1-butenyl, 2-butenyl, 3-butenyl, 1-butynyl, 2-butynyl, 3-butynyl, 1-pentenyl, 2-pentenyl, 3-pentenyl, 4-pentenyl, 1-pentynyl, 2-pentynyl, 3-pentynyl, 4-pentynyl, hexenyl, hexynyl and —CH=CH—CH=CH—CH$_3$.

In the context of the present invention, cycloaliphatic radicals include both saturated and unsaturated cyclic hydrocarbon radicals, which may each have 1, 2, 3, 4 or 5 heteroatom(s) as the ring member(s) selected independently of one another from the group consisting of oxygen, nitrogen and sulphur. Examples include cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl, morpholinyl, pyrrolidinyl, tetrahydrothiophenyl, tetrahydropyranyl, thiomorpholinyl, dioxolanyl, azepanyl, diazepanyl and dithiolanyl radicals.

Suitable aryl radicals include phenyl and naphthyl (1-naphtyl and 2-naphthyl).

Suitable heteroaryl radicals include pyridinyl, thiophenyl (thienyl), furanyl (furyl), pyrazolinyl, pyrimidinyl, pyridinyl, 2-pyridinyl, 3-pyridinyl, 4-pyridinyl, 2-pyrimidinyl, 4-pyrimidinyl, 5-pyrimidinyl, pyridazinyl, 3-pyridazinyl, 4-pyridazinyl, pyrazinyl, 3-pyrazinyl, imidazolyl, 2-imidazolyl, 4-imidazolyl, isoxazolyl, 3-isoxazolyl, 4-isoxazolyl, 5-isoxazolyl, pyrazolyl, 3-pyrazolyl, 4-pyrazolyl, 5-pyrazolyl, oxazolyl, 2-oxazolyl, 4-oxazolyl, 5-oxazolyl, 1,2,3-oxathiazolyl, 1,2,3-oxadiazolyl, 1,2,4-oxadiazolyl, 1,2,5-oxadiazolyl, 1,3,4-oxadiazolyl, thiazolyl, 2-thiazolyl, 4-thiazolyl, 5-thiazolyl, 3-isothiazolyl, 4-isothiazolyl, 5-isothiazolyl, 2-thiophenyl, 3-thiophenyl, pyrrolyl, 2-pyrrolyl, 3-pyrrolyl, 3-isopyrrolyl, 4-isopyrrolyl, 5-isopyrrolyl, 1,2,4-oxadiazol-3-yl, 1,2,4-oxadiazol-5-yl, 1,2,4-thiadiazol-3-yl, 1,2,4-thiadiazol-5-yl, 1,3,4-thiadiazol-5-yl, triazolyl, 1,2,4-triazol-3-yl, 1,2,4-triazol-5-yl, 1,2,3,4-tetrazol-5-yl, 1,2,3,4-thiatriazolyl, quinolinyl, triazinyl, quinoxalinyl, pyranyl, indolyl, isoindolyl, benzo[b]furanyl, benzo[b]thiophenyl, indazolyl and isoquinolinyl.

The person skilled in the art would understand that some of the substituted 5,6,7,8-tetrahydro-imidazo[1,2-a]pyridin-2-ylamine compounds of the general formula I according to the invention may be present in the form of tautomers, which are also the subject of the present invention and may also each be present as active ingredients in the pharmaceutical compositions described hereinafter.

Preferred substituted 5,6,7,8-tetrahydro-imidazo[1,2-a]pyridin-2-ylamine compounds of the aforementioned general formula I are those in which $R^1$ represents a hydrogen radical; —C(=O)—OR$^5$; —(CHR$^6$)—(CH$_2$)$_m$—C(=O)—OR$^7$ in which m=0, 1, 2, 3, 4 or 5; —C(=O)—NH—R$^{10}$; —(CH$_2$)$_o$—C(=O)—NHR$^{11}$ in which o=0, 1, 2, 3, 4 or 5; —(CHR$^{16}$)—X$_q$—(CHR$^{17}$)$_r$—Y$_s$—(CHR$^{18}$)$_t$—Z$_u$—R$^{19}$ in which q=0 or 1, r=0 or 1, s=0 or 1, t=0 or 1, u=0 or 1 and in which X,Y and Z, independently of one another, each represent O, S, NH and N(CH$_3$);

an optionally substituted alkyl radical selected from the group consisting of methyl, ethyl, n-propyl, isopropyl, —(CH$_2$)—(CH$_2$)—(CN), n-butyl, sec-butyl, isobutyl, tert-butyl, —C(H)(CH$_3$)—C(H)(CH$_3$)$_2$ and —(CH$_2$)—(CH$_2$)—(C(CH$_3$)$_3$), an alkenyl radical selected from the group consisting of vinyl, 1-propenyl and 2-propenyl, a (hetero)cycloaliphatic radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, (6,6)-dimethyl-[3.1.1]-bicycloheptyl, indanyl, indenyl, (1,4)-benzodioxanyl, (1,2,3,4)-tetrahydronaphthyl, (1,2,3,4)-tetrahydroquinolinyl and (1,2,3,4)-tetrahydroquinazolinyl, in which the respective (hetero)cycloaliphatic radical may optionally be substituted with 1, 2, 3, 4 or 5 substituents selected independently of one another from the group consisting of F, Cl, Br, I, —CN, —CF$_3$, —SF$_5$, —OH, —NH$_2$, —O—CF$_3$, —SH, —O—CH$_3$, —O—C$_2$H$_5$, methyl, ethyl, n-propyl, isopropyl, n-butyl, sec-butyl, isobutyl, tert-butyl, —S—CH$_3$, —S—C$_2$H$_5$, —C(=O)—O—CH$_3$, —C(=O)—O—C$_2$H$_5$, oxo (=O), —N(CH$_3$)$_2$, —N(C$_2$H$_5$)$_2$, —N(H)(CH$_3$), —N(H)(C$_2$H$_5$), —NO$_2$, —SCF$_3$, —C(=O)—OH, —(CH$_2$)-benzo[b]furanyl, —O-phenyl, —O-benzyl, phenyl and benzyl, in which the respective cyclic portion of the —(CH$_2$)-benzo[b]furanyl, —O-phenyl, —O-benzyl-, benzyl and phenyl radicals may be substituted with 1, 2, 3, 4 or 5 substituents selected independently of one another from the group consisting of F, Cl, Br, —OH, —CF$_3$, —SF$_5$, —CN, —NO$_2$, methyl, ethyl, isopropyl, n-propyl, —O—CH$_3$, —O—C$_2$H$_5$, —O—CF$_3$, phenyl and —O-benzyl, or a radical selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, in which the respective radical may optionally be substituted with 1, 2, 3, 4 or 5 substituents selected independently of one another from the group consisting of F, Cl, Br, I, —CN, —NO$_2$, —OH, —SH, methyl, ethyl, n-Propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$ and —NH—C(=O)—O—C(CH$_3$)$_3$, and the respective remaining radicals R$^1$ and R$^2$ together, and also R$^2$-R$^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which
R$^2$ represents a hydrogen radical,
—(CHR$^{16}$)—R$^{19}$,
or an alkyl radical selected from the group consisting of methyl, ethyl, n-propyl, isopropyl, n-butyl, sec-butyl, isobutyl and tert-butyl, and the respective remaining radicals R$^1$, R$^1$ and R$^2$ together, and R$^3$-R$^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which R$^1$ and R$^2$ form a radical with the nitrogen atom which binds them as the ring member, the radical being selected from the group consisting of

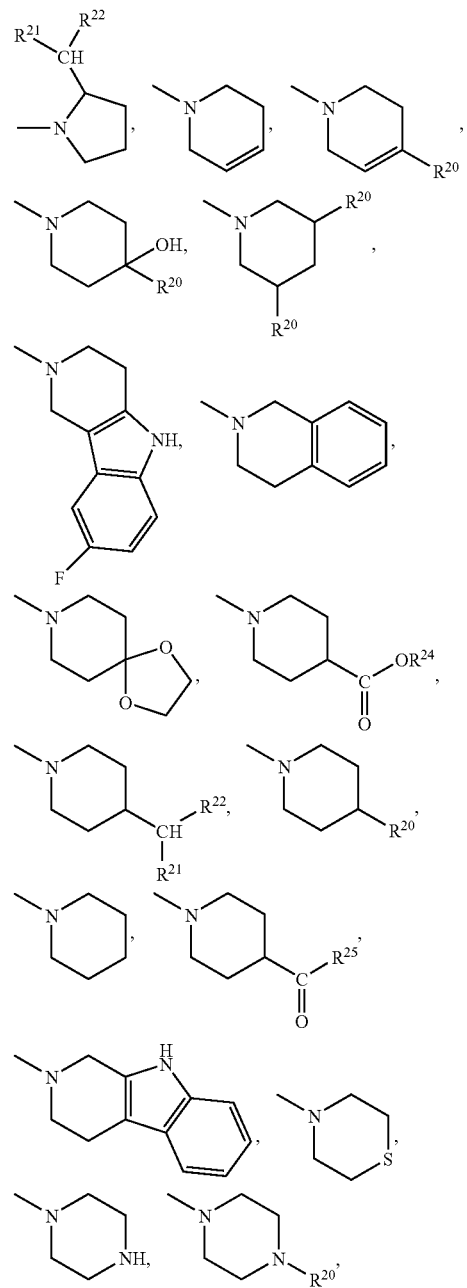

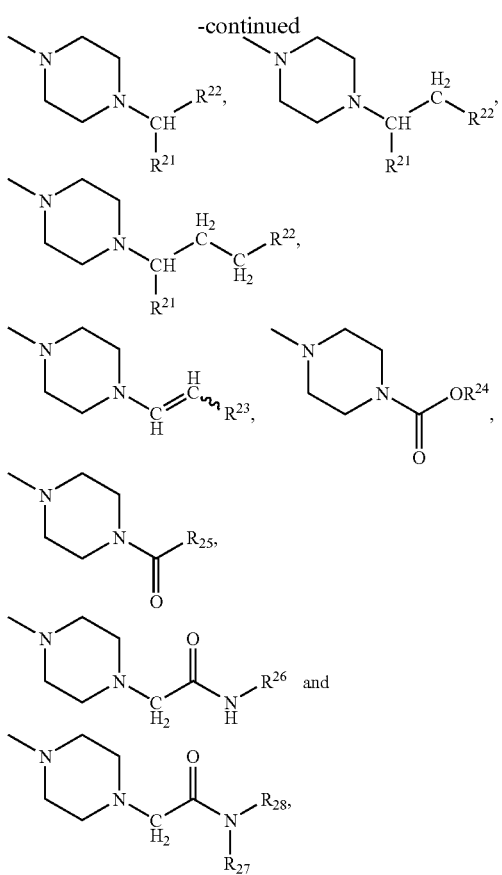

and the respective remaining radicals $R^1$ and $R^2$ separately and $R^3$-$R^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which $R^3$ represents a hydrogen radical or an alkyl radical selected from the group consisting of methyl, ethyl, n-propyl, isopropyl, n-butyl, sec-butyl, isobutyl and tert-butyl and n-pentyl, and the respective remaining radicals $R^1$, $R^2$ and $R^4$-$R^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which $R^4$ represents a phenyl or naphthyl radical which may each be substituted with 1, 2, 3, 4 or 5 substituents selected independently of one another from the group consisting of methyl, ethyl, n-propyl, isopropyl, n-butyl, isobutyl, sec-butyl, tert-butyl, F, Cl, Br, I, —CN, —SF$_5$, —S—CF$_3$, —NH$_2$, —N(CH$_3$)$_2$, —N(C$_2$H$_5$)$_2$, —N(H)(CH$_3$), —N(H) (C$_2$H$_5$), —SH, —NO$_2$, —CF$_3$, —OCF$_3$, —OH, —O—CH$_3$ and —O—C$_2$H$_5$ and/or bound by a —(CH$_2$)—, —(CH$_2$)$_2$— or —(CH$_2$)$_3$ group, and the respective remaining radicals $R^1$-$R^3$ and $R^5$-$R^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which $R^5$, $R^7$, $R^8$, $R^9$, $R^{10}$, $R^{11}$, $R^{12}$, $R^{13}$, $R^{14}$ and $R^{15}$, independently of one another, each represent an alkyl radical selected from the group consisting of methyl, ethyl, n-propyl, isopropyl, n-butyl, sec-butyl, isobutyl and tert-butyl, in which the respective alkyl radical may optionally be substituted with 1, 2, 3, 4 or 5 substituents selected independently of one another from the group consisting of F, Cl, Br, I, —CN, —NO$_2$, —OH, —SH and —NH$_2$, or a radical selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, in which the respective radical may be bound by a —(CH$_2$)—, —(CH$_2$)$_2$— or —(CH$_2$)$_3$ group and/or optionally substituted with 1, 2, 3, 4 or 5 substituents selected independently of one another from the group consisting of F, Cl, Br, I, —CN, —NO$_2$, —OH, —SH, methyl, ethyl, n-propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$), —N(H)(C$_2$H$_5$), —NH—C (=O)—O—CH$_3$, —NH—C(=O)—O—C$_2$H$_5$ and —NH—C(=O)—O—C(CH$_3$)$_3$, and the respective remaining radicals $R^1$-$R^4$, $R^6$ and $R^{16}$-$R^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which $R^6$ represents a hydrogen radical, a radical selected from the group consisting of methyl, ethyl, n-propyl, isopropyl, n-butyl, sec-butyl, isobutyl, tert-butyl, n-pentyl, sec-pentyl, —C(H)(CH$_3$)—C(H)(CH$_3$)$_2$, —(CH$_2$)—(CH$_2$)—(C(CH$_3$)$_3$), —C(H)(CH$_3$)(O(C (CH$_3$)$_3$)) and n-hexyl, in which the respective radical may be substituted with 1, 2, 3, 4 or 5 substituents selected independently of one another from the group consisting of F, Cl, Br, I, —CN, —NO$_2$, —OH, —SH and —NH$_2$, or a radical selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, in which the respective radical may be bound by a —(CH$_2$)—, —(CH$_2$)$_2$— or —(CH$_2$)$_3$ group and/or optionally substituted with 1, 2, 3, 4 or 5 substituents selected independently of one another from the group consisting of F, Cl, Br, I, —CN, —NO$_2$, —OH, —SH, methyl, ethyl, n-propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$ and —NH—C(=O)—O—C(CH$_3$)$_3$, and the respective remaining radicals R$^1$-R$^5$ and R$^7$-R$^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which R$^{16}$, R$^{17}$ and R$^{18}$, independently of one another, each represent a hydrogen radical, a radical selected from the group consisting of methyl, ethyl, n-propyl, isopropyl, n-butyl, sec-butyl, isobutyl, tert-butyl, n-pentyl, sec-pentyl, —C(H)(CH$_3$)—C(H)(CH$_3$)$_2$, —(CH$_2$)—(CH$_2$)—(C(CH$_3$)$_3$), —(CH$_2$)—O—(CH$_3$) and n-hexyl, in which the respective radical may optionally be substituted with 1, 2, 3, 4 or 5 substituents selected independently of one another from the group consisting of F, Cl, Br, I, —CN, —NO$_2$, —OH, —SH and —NH$_2$, or a radical selected from the group consisting of phenyl and naphthyl, in which the respective radical may be substituted with 1, 2, 3, 4 or 5 substituents selected independently of one another from the group consisting of F, Cl, Br, I, —CN, —NO$_2$, —OH, —SH, methyl, ethyl, n-propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$ and —NH—C(=O)—O—C(CH$_3$)$_3$, and the respective remaining radicals R$^1$-R$^{15}$ and R$^{19}$-R$^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which R$^{19}$ represents a (hetero)cycloaliphatic radical selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, (6,6)-dimethyl-[3.1.1]-bicycloheptyl, adamantyl (tricyclo-[3.3.1.1$^{3,7}$]-decanyl), indanyl, indenyl, (1,4)-benzodioxanyl, (1,2,3,4)-tetrahydronaphthyl, (1,2,3,4)-tetrahydroquinolinyl and (1,2,3,4)-tetrahydroquinazolinyl, in which the respective (hetero)cycloaliphatic radical may optionally be substituted with 1, 2, 3, 4 or 5 substituents selected independently of one another from the group consisting of F, Cl, Br, I, —CN, —CF$_3$, —SF$_5$, —OH, —NH$_2$, —O—CF$_3$, —SH, —O—CH$_3$, —O—C$_2$H$_5$, methyl, ethyl, n-propyl, isopropyl, n-butyl, sec-butyl, isobutyl, tert-butyl, —S—CH$_3$, —S—C$_2$H$_5$, —C(=O)—O—CH$_3$, —C(=O)—O—C$_2$H$_5$, Oxo (=O), —N(CH$_3$)$_2$, —N(C$_2$H$_5$)$_2$, —N(H)(CH$_3$), —N(H)(C$_2$H$_5$), —NO$_2$, —SCF$_3$, —C(=O)—OH, —(CH$_2$)-benzo[b]furanyl, —O-phenyl, —O-benzyl, phenyl and benzyl, or a radical selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, in which the respective radical may optionally be substituted with 1, 2, 3, 4 or 5 substituents selected independently of one another from the group consisting of F, Cl, Br, I, —CN, —NO$_2$, —OH, —SH, methyl, ethyl, n-Propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$ and —NH—C(=O)—O—C(CH$_3$)$_3$, and the respective remaining radicals R$^1$-R$^{18}$ and R$^{20}$-R$^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which R$^{20}$ represents an alkyl radical selected from the group consisting of methyl, ethyl, n-propyl, isopropyl, n-butyl, isobutyl, sec-butyl, tert-butyl and n-pentyl, a (hetero)cycloaliphatic radical selected from the group consisting of cyclopentyl, cyclohexyl, piperidinyl and cycloheptyl, in which the respective (hetero)cycloaliphatic radical may optionally be substituted with 1, 2, 3, 4 or 5 substituents selected independently of one another from the group consisting of F, Cl, Br, I, —CN, —CF$_3$, —SF$_5$, —OH, —NH$_2$, —O—CF$_3$, —SH, —O—CH$_3$, —O—C$_2$H$_5$, methyl, ethyl, n-propyl, isopropyl, n-butyl, sec-butyl, isobutyl and tert-butyl, or a radical selected from the group consisting of phenyl, naphthyl, (1,3)-benzodioxolyl, thiophenyl, furanyl, pyridinyl, imidazolyl, indolyl, benzo[b]furanyl, benzo[b]thiophenyl, thiazolyl, oxazolyl, isoxazolyl, pyridazinyl, pyrazinyl, pyrimidinyl, and quinolinyl, in which the respective radical may optionally be substituted with 1, 2, 3, 4 or 5 substituents selected independently of one another from the group consisting of methyl, ethyl, n-propyl, isopropyl, n-butyl, isobutyl, sec-butyl, tert-butyl, F, Cl, Br, —CN, —SF$_5$, —O—CF$_3$, —S—CF$_3$, —NH$_2$, —N(CH$_3$)$_2$, —N(C$_2$H$_5$)$_2$, —N(H)(CH$_3$), —N(H)(C$_2$H$_5$), —SH, —NO$_2$, —CF$_3$, —OCF$_3$, —OH, —O—CH$_3$ and —O—C$_2$H$_5$, and the respective remaining radicals R$^1$-R$^{19}$ and R$^{21}$-R$^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which $R^{21}$ represents a hydrogen radical or a phenyl or naphthyl radical, which may be substituted with 1, 2 or 3 substituents selected independently of one another from the group consisting of methyl, ethyl, n-propyl, isopropyl, n-butyl, isobutyl, sec-butyl, tert-butyl, F, Cl and Br, and the respective remaining radicals $R^1$-$R^{20}$ and $R^{22}$-$R^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which $R^{22}$ and $R^{23}$, independently of one another, each represent a (hetero)cycloaliphatic radical selected from the group consisting of pyrrolidinyl, morpholinyl and thiomorpholinyl, in which the respective (hetero)cycloaliphatic radical may be substituted with 1, 2, 3, 4 or 5 substituents selected independently of one another from the group consisting of F, Cl, Br, I, —CN, —CF$_3$, —SF$_5$, —OH, —NH$_2$, —O—CF$_3$, —SH, —O—CH$_3$, —O—C$_2$H$_5$, methyl, ethyl, n-propyl, isopropyl, n-butyl, sec-butyl, isobutyl and tert-butyl, or a radical selected from the group consisting of phenyl, naphthyl, (1,3)-benzodioxolyl, thiophenyl, furanyl, pyridinyl, imidazolyl, indolyl, benzo[b]furanyl, benzo[b]thiophenyl, thiazolyl, oxazolyl, isoxazolyl, pyridazinyl, pyrazinyl, pyrimidinyl, and quinolinyl, in which the radical may optionally be substituted with 1, 2, 3, 4 or 5 substituents selected independently of one another from the group consisting of methyl, ethyl, n-propyl, isopropyl, n-butyl, isobutyl, sec-butyl, tert-butyl, F, Cl, Br, —CN, —SF$_5$, —O—CF$_3$, —S—CF$_3$, —NH$_2$, —N(CH$_3$)$_2$, —N(C$_2$H$_5$)$_2$, —N(H)(CH$_3$), —N(H)(C$_2$H$_5$), —SH, —NO$_2$, —CF$_3$, —OCF$_3$, —OH, —O—CH$_3$ and —O—C$_2$H$_5$, and the respective remaining radicals $R^1$-$R^{21}$ and $R^{24}$-$R^{28}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

In addition, preferred substituted 5,6,7,8-tetrahydro-imidazo[1,2-a]pyridin-2-ylamine compounds of the general formula I are also those in which $R^{24}$ represents an alkyl radical selected from the group consisting of methyl, ethyl, n-propyl, isopropyl, n-butyl, sec-butyl, isobutyl and tert-butyl, $R^{25}$ represents a radical selected from the group consisting of phenyl, naphthyl, furanyl, pyrazinyl and pyrimidinyl, which may be bound by a —(CH$_2$), —(CH$_2$)$_2$ or —(CH$_2$)$_3$ group and/or substituted with 1, 2 or 3 substituents selected independently of one another from the group consisting of methyl, ethyl, n-propyl and isopropyl, $R^{26}$ represents an alkyl radical selected from the group consisting of methyl, ethyl, n-propyl and isopropyl, $R^{27}$ represents an alkyl radical selected from the group consisting of methyl, ethyl, isopropyl and n-propyl or a phenyl radical, and $R^{28}$ represents an alkyl radical selected from the group consisting of methyl, ethyl, isopropyl and n-propyl or a phenyl radical, and the respective remaining radicals $R^1$-$R^{23}$ are as defined hereinbefore, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

Particularly preferred substituted 5,6,7,8-tetrahydro-imidazo[1.2-a]pyridin-2-ylamine compounds of the general formula I are those in which $R^1$ represents —C(=O)—OR$^5$; —(CHR$^6$)—C(=O)—OR$^7$; —C(=O)—NHR$^{11}$; —(CH$_2$)—C(=O)—NHR$^{11}$; —(CHR$^{16}$)—R$^{19}$; —(CHR$^{16}$)—(CHR$^{17}$)—R$^{19}$; —(CHR$^{16}$)—(CHR$^{17}$)—O—R$^{19}$; —(CHR$^{16}$)—(CHR$^{17}$)—(CHR$^{18}$)—R$^{19}$; —(CHR$^{16}$)—(CHR$^{17}$)—S—(CHR$^{18}$)—R$^{19}$; —(CHR$^{16}$)—(CHR$^{17}$)—(CHR$^{18}$)—N(CH$_3$)—R$^{19}$, an optionally substituted alkyl radical selected from the group consisting of methyl, ethyl, n-propyl, isopropyl, —CH$_2$—CH$_2$—CN, n-butyl, sec-butyl, isobutyl, tert-butyl, —CH(CH$_3$)—CH(CH$_3$)$_2$ and —CH$_2$—CH$_2$—C(CH$_3$)$_3$, an alkenyl radical selected from the group consisting of 1-propenyl and 2-propenyl, a radical selected from the group consisting of cyclopentyl, cyclohexyl, cycloheptyl, (6,6)-dimethyl-[3.1.1]-bicycloheptyl, indanyl and indenyl, in which the respective radical may be substituted with 1, 2 or 3 substituents selected independently from the group consisting of F, Cl, Br, methyl, ethyl, isopropyl, n-propyl and —O-benzyl, a pyrrolidinyl radical which may be substituted with a —(CH$_2$)— benzo[b]furanyl or benzyl radical, in which the respective cyclic portion of the benzyl radical may be substituted with 1, 2 or 3 substituents selected independently of one another from the group consisting of F, Cl, Br, —OH, methyl, ethyl, isopropyl, n-propyl, —CF$_3$, —O—CH$_3$, —O—C$_2$H$_5$, phenyl and —O-benzyl, or a radical selected from the group consisting of phenyl, naphthyl, (1,3)-benzodioxolyl and (1,4)-benzodioxanyl, in which the respective radical may be substituted with 1, 2 or 3 substituents selected independently of one another from the group consisting of F, Cl, Br, I, methyl, ethyl, n-propyl, isopropyl, n-butyl, sec-butyl, isobutyl, tert-butyl, —O-phenyl, —O-benzyl, —NH—C(=O)—O—CH$_3$, —NH—C(=O)—O—C$_2$H$_5$ and —NH—C(=O)—O—C(CH$_3$)$_3$;

$R^2$ represents a hydrogen radical,

—(CHR$^{16}$)—R$^{19}$, or an alkyl radical selected from the group consisting of methyl, ethyl, n-propyl, isopropyl, n-butyl, sec-butyl, isobutyl and tert-butyl;

or $R^1$ and $R^2$, together with the nitrogen atom which binds them as a ring member, form a radical selected from the group consisting of

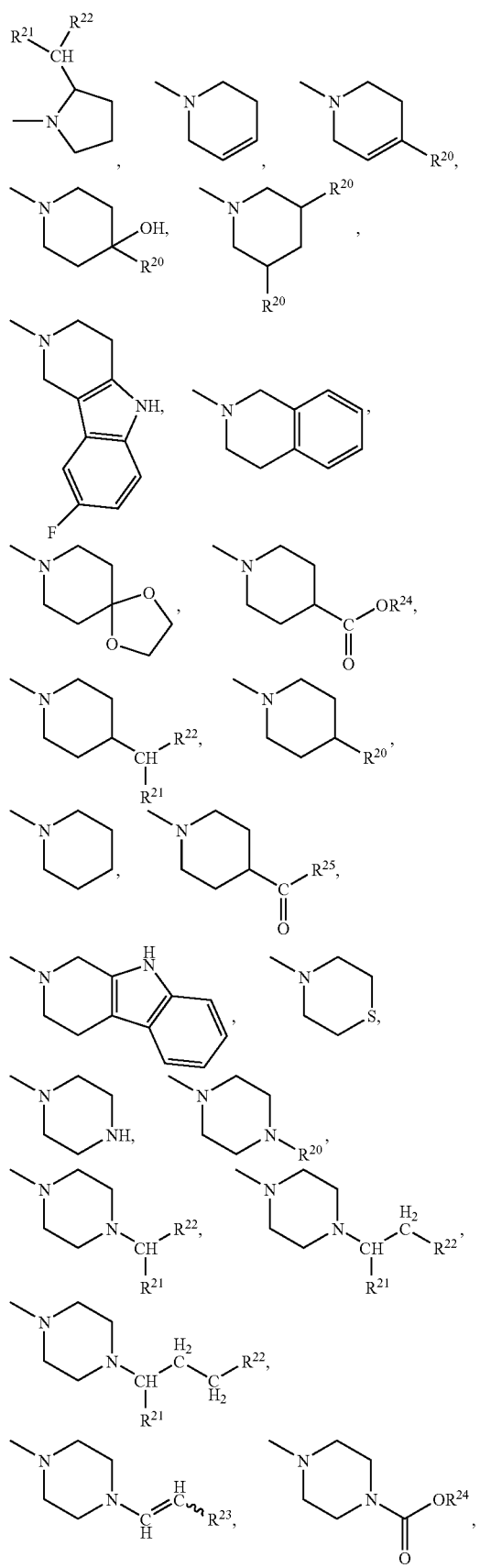

-continued

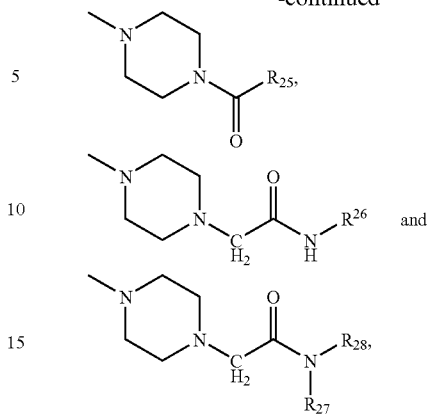

$R^4$ represents a radical selected from the group consisting of

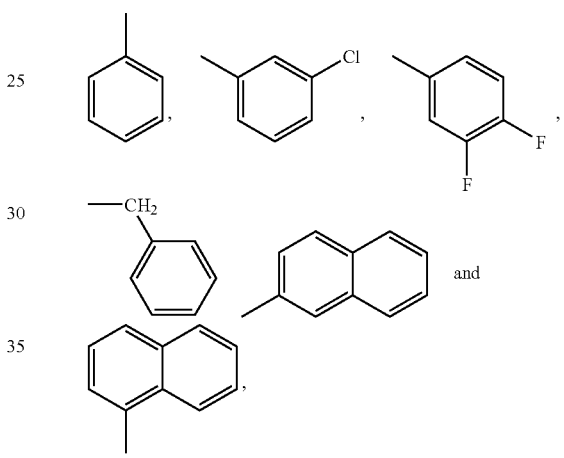

$R^5$, $R^7$ and $R^{11}$, independently of one another, each represent
an alkyl radical selected from the group consisting of methyl, ethyl, n-propyl, isopropyl, n-butyl, sec-butyl, isobutyl and tert-butyl;
or a benzyl or naphthyl radical;

$R^6$ represents a hydrogen radical,
a radical selected from the group consisting of methyl, ethyl, n-propyl, isopropyl, n-butyl, sec-butyl, isobutyl, tert-butyl, n-pentyl, sec-pentyl, neopentyl and —C(H)(CH$_3$)(O(C(CH$_3$)$_3$)),
or an indolyl radical, bound by a —(CH$_2$) group;

$R^{16}$ represents a hydrogen radical,
a radical selected from the group consisting of methyl, ethyl, isopropyl, n-propyl, n-butyl, sec-butyl, isobutyl, tert-butyl and —(CH$_2$)—O—(CH$_3$),
or a phenyl radical;

$R^{17}$ represents a hydrogen radical,
an alkyl radical selected from the group consisting of methyl, ethyl, isopropyl, n-propyl, n-butyl, isobutyl, sec-butyl and tert-butyl or a phenyl radical;

$R^{18}$ represents a hydrogen radical
or a phenyl radical;

$R^{19}$ represents a (hetero)cycloaliphatic radical selected from the group consisting of cyclopentyl, cyclohexyl, cycloheptyl, tetrahydrofuranyl, tetrahydrothiophenyl, pyrrolidinyl, piperidinyl, adamantyl (tricyclo-[3.3.1.1$^{3,7}$]-decanyl) and (1,4)-benzodioxanyl, in which the respective (hetero)cycloaliphatic radical may be substituted with 1 or 2 substituents selected independently of one another from the group consisting of methyl, ethyl, isopropyl and n-propyl, or a radical selected from the group consisting of phenyl, naphthyl, (1,3)-benzodioxolyl, (1,4)-benzodioxanyl, thiophenyl, furanyl, pyridinyl, imidazolyl, indolyl and isoindolyl, in which the respective radical may optionally be substituted with 1, 2, 3, 4 or 5 substituents selected independently of one another from the group consisting of F, Cl, Br, I, methyl, ethyl, n-propyl, isopropyl, n-butyl, sec-butyl, isobutyl, tert-butyl, —$CF_3$, —O—$CH_3$, —O—$C_2H_5$, —O—$CF_3$, —O-phenyl, —O-benzyl, —$NH_2$, —$N(CH_3)_2$, —$N(C_2H_5)_2$, —N(H)($CH_3$) and —N(H)($C_2H_5$);

$R^{20}$ represents a methyl or ethyl radical,
a (hetero)cycloaliphatic radical selected from the group consisting of cyclopentyl, cyclohexyl, piperidinyl and cycloheptyl,
or a phenyl or pyridinyl radical, which may be substituted with 1, 2 or 3 substituents selected independently of one another from the group consisting of methyl, ethyl, n-propyl, isopropyl, n-butyl, isobutyl, sec-butyl, tert-butyl, F, Cl, Br, —$CF_3$, —OH, —O—$CH_3$ and —O—$C_2H_5$;

$R^{21}$ represents a hydrogen radical
or a phenyl radical, which may be substituted with 1, 2 or 3 substituents selected independently of one another from the group consisting of methyl, ethyl, n-propyl, isopropyl, n-butyl, isobutyl, sec-butyl, tert-butyl, F, Cl and Br;

$R^{22}$ represents a pyrrolidinyl or morpholinyl radical
or a radical selected from the group consisting of phenyl, naphthyl, (1,3)-benzodioxolyl, thiophenyl, benzo[b]furanyl, benzo[b]thiophenyl and quinolinyl, in which the respective radical may be substituted with 1, 2 or 3 substituents selected independently of one another from the group consisting of methyl, ethyl, n-propyl, F, Cl, Br, —OH, —O—$CH_3$ and —O—$C_2H_5$;

$R^{23}$ represents a phenyl radical;

$R^{24}$ represents an alkyl radical selected from the group consisting of methyl, ethyl, n-propyl, isopropyl, n-butyl, isobutyl, sec-butyl and tert-butyl;

$R^{25}$ represents a radical selected from the group consisting of phenyl, naphthyl, furanyl, pyrazinyl and pyrimidinyl, which may be bound by a —($CH_2$) group and/or substituted with 1, 2 or 3 substituents selected independently of one another from the group consisting of methyl, ethyl, n-propyl and isopropyl;

$R^{26}$ represents an alkyl radical selected from the group consisting of methyl, ethyl, n-propyl and isopropyl;

$R^{27}$ represents an alkyl radical selected from the group consisting of methyl, ethyl, isopropyl and n-propyl
and
$R^{28}$ represents a phenyl radical;

each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

Very particularly preferred substituted 5,6,7,8-tetrahydroimidazo[1.2-a]pyridin-2-ylamine compounds of the general formula I are those in which
$R^1$ represents —C(=O)—O—$CH_3$, —C(=O)—O—$C_2H_5$,
a radical selected from the group consisting of

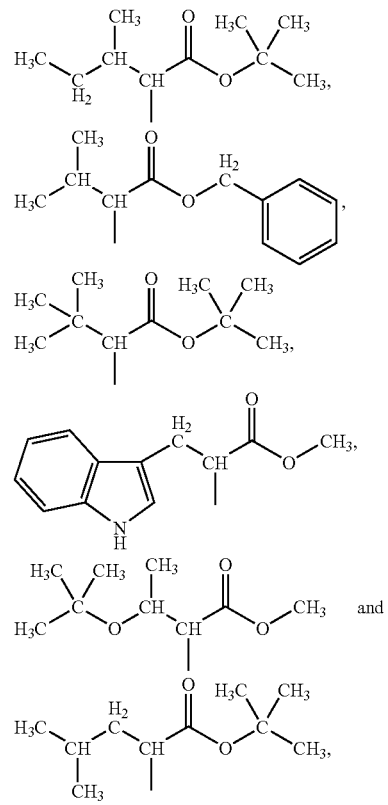

the following radical

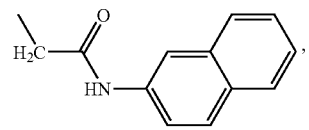

an optionally substituted alkyl radical selected from the group consisting of methyl, ethyl, n-propyl, isopropyl, —$CH_2$—$CH_2$—CN, n-butyl, sec-butyl, isobutyl, tert-butyl, —CH($CH_3$)—CH($CH_3$)$_2$ and —$CH_2$—$CH_2$—C($CH_3$)$_3$, an alkenyl radical selected from the group consisting of 1-propenyl and 2-propenyl, a cycloaliphatic radical selected from the group consisting of cyclopentyl, cyclohexyl, (6,6)-dimethyl-[3.1.1]-bicycloheptyl, adamantyl (tricyclo-[3.3.1.1$^{3,7}$]-decanyl), indanyl and indenyl, in which the respective cycloaliphatic radical may be substituted with 1, 2 or 3 substituents selected, independently of one another, from the group consisting of F, Cl, Br, methyl, ethyl, n-propyl and —O-benzyl, a pyrrolidinyl radical which may be substituted with a ($CH_2$)-benzo[b]furanyl or benzyl radical, in which the respective cyclic portion of the benzyl radical may be substituted with 1, 2 or 3 substituents selected independently of one another from the group consisting of F, Cl, Br, —OH, —$CF_3$, —O—$CH_3$, —O—$C_2H_5$, phenyl and —O-benzyl, a radical selected from the group consisting of phenyl, naphthyl, (1,3)-benzodioxolyl and (1,4)-benzodioxanyl, in which the respective radical may be substituted with 1, 2 or 3 substituents selected independently of one another from the group consisting of F, Cl, Br, I, methyl, ethyl, n-propyl, isopropyl, n-butyl, sec-butyl, isobutyl, tert-butyl, —O-phenyl, —O-benzyl, —NH—C(=O)—O—CH₃, —NH—C(=O)—O—C₂H₅ and —NH—C(=O)—O—C(CH₃)₃ a radical selected from the group consisting of

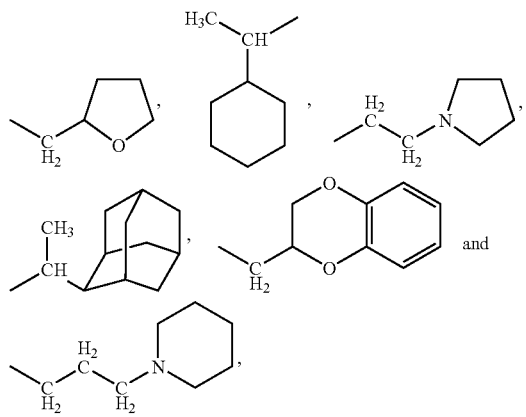

in which the respective (hetero)cycloaliphatic portion may be substituted with 1 or 2 substituents selected independently of one another from the group consisting of methyl, ethyl, isopropyl and n-propyl, or a radical selected from the group consisting of

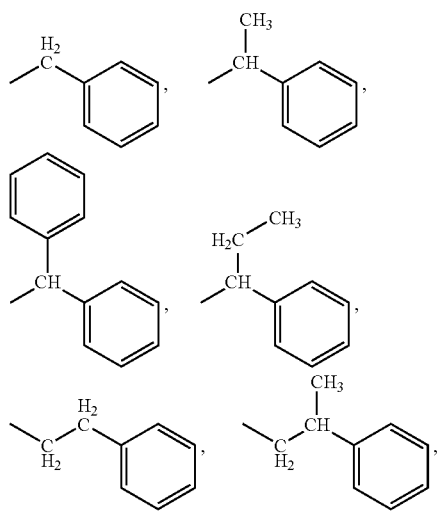

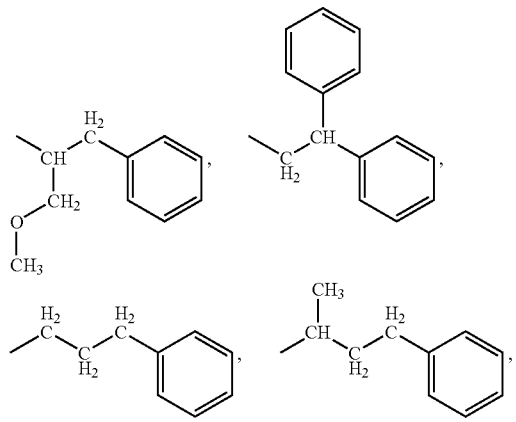

-continued

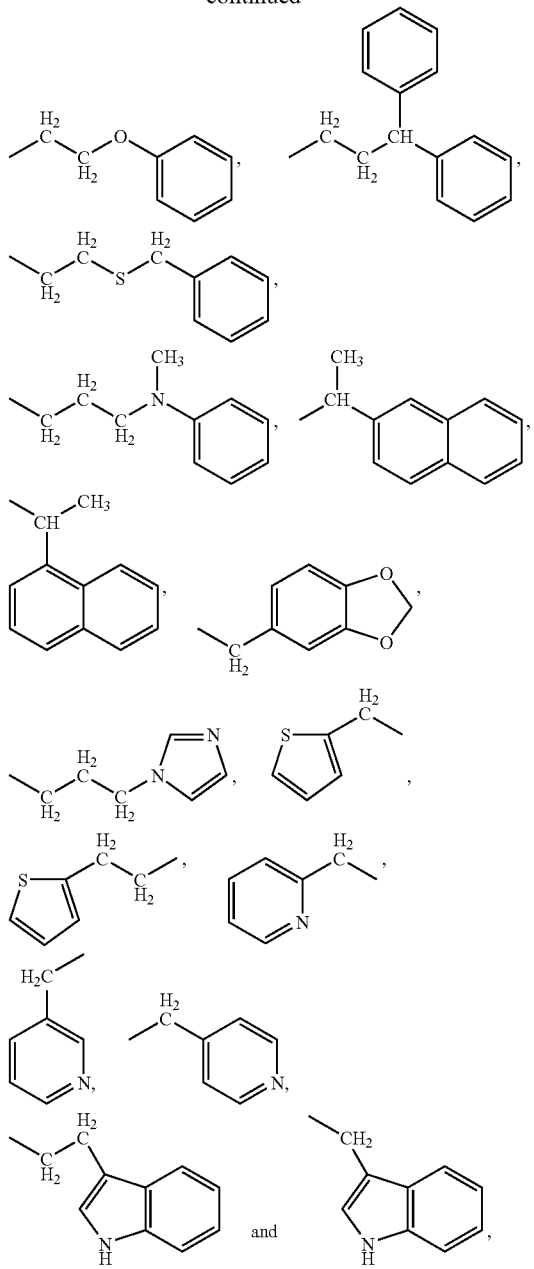

in which the respective (hetero)aromatic portion may be substituted with 1, 2, 3, 4 or substituents selected independently of one another from the group consisting of F, Cl, Br, I, methyl, ethyl, n-propyl, isopropyl, n-butyl, sec-butyl, isobutyl, tert-butyl, —CF₃, —O—CH₃, —O—C₂H₅, —O—CF₃, —O-phenyl, —O-benzyl, —NH₂, —N(CH₃)₂, —N(C₂H₅)₂, —N(H)(CH₃) and —N(H)(C₂H₅), R² represents a hydrogen radical,
a benzyl radical which may be substituted once, twice or three times with —O—CH₃,
or an alkyl radical selected from the group consisting of methyl, ethyl, n-propyl, isopropyl, n-butyl, sec-butyl, isobutyl tert-butyl, or R¹ and R², together with the nitrogen atom which binds them as a ring member, form a radical from the group consisting of

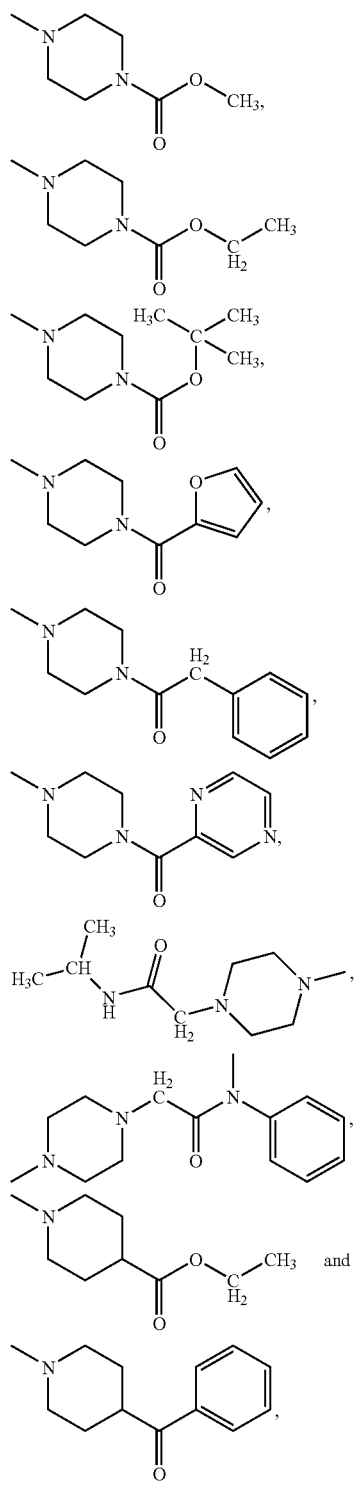

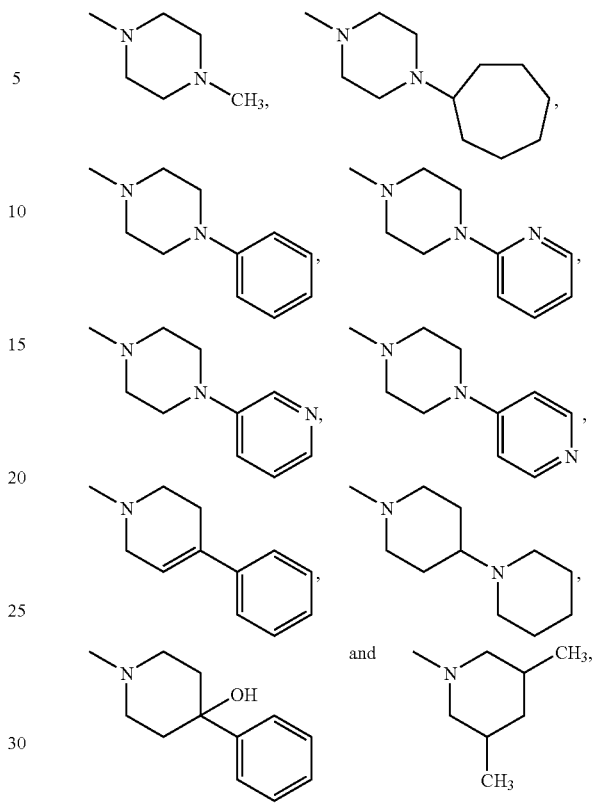

in which the respective (hetero)aromatic portion of the aforementioned radicals may optionally be substituted with 1, 2 or 3 substituents selected independently of one another from the group consisting of methyl, ethyl, n-propyl and isopropyl, or $R^1$ and $R^2$, together with the nitrogen atom which binds them as a ring member, form a radical selected from the following group in which the respective (hetero)aromatic portion of the aforementioned radicals may be substituted with 1, 2 or 3 substituents selected independently of one another from the group consisting of methyl, ethyl, n-propyl, isopropyl, n-butyl, isobutyl, sec-butyl, tert-butyl, F, Cl, Br, —$CF_3$, —OH, —O—$CH_3$ and —O—$C_2H_5$, or $R^1$ and $R^2$, together with the nitrogen atom which binds them as a ring member, form a radical selected from the group consisting of

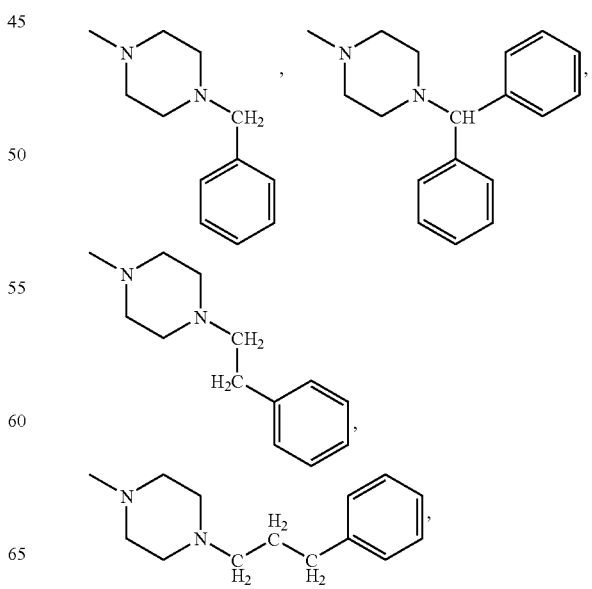

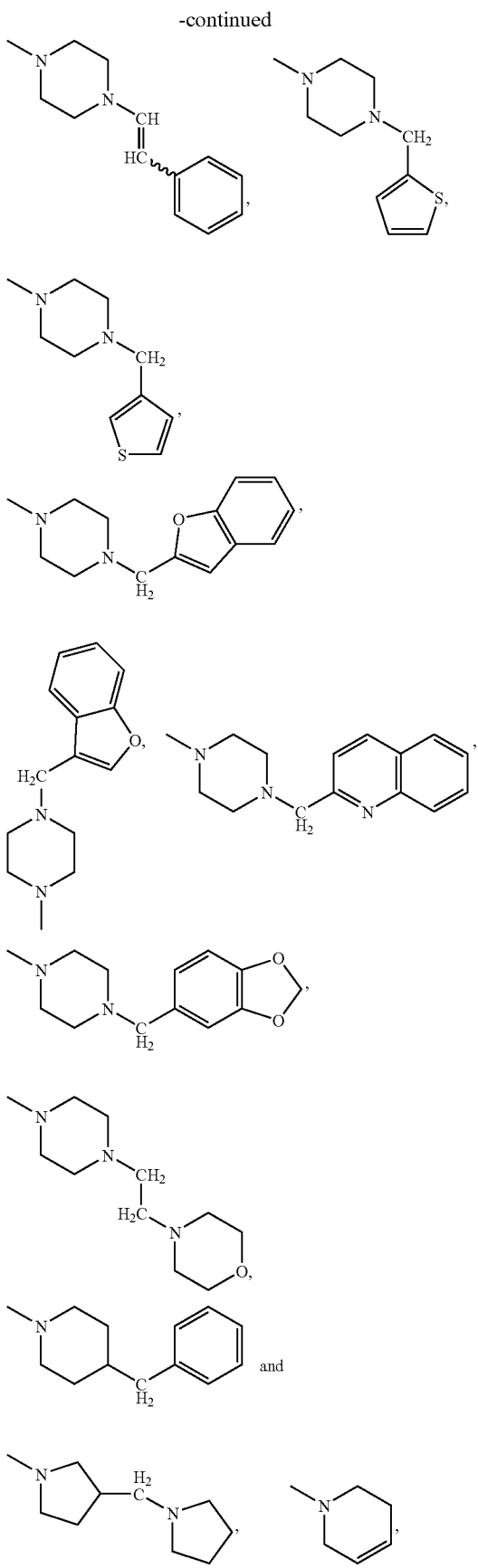

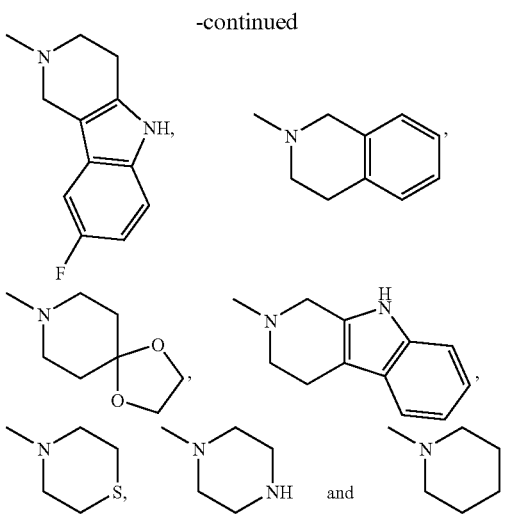

in which the respective (hetero)aromatic portion of the aforementioned radicals may be substituted with 1, 2 or 3 substituents selected independently of one another from the group consisting of methyl, ethyl, n-propyl, F, Cl, Br, —OH, —O—$CH_3$ and —O—$C_2H_5$, or $R^1$ and $R^2$, together with the nitrogen atom which binds them as a ring member, form a radical selected from the group consisting of $R^3$ represents an alkyl radical selected from the group consisting of methyl, ethyl, n-propyl, isopropyl, n-butyl, sec-butyl, isobutyl and tert-butyl;

$R^4$ represents a radical selected from the group consisting of

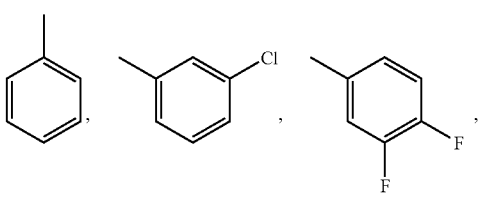

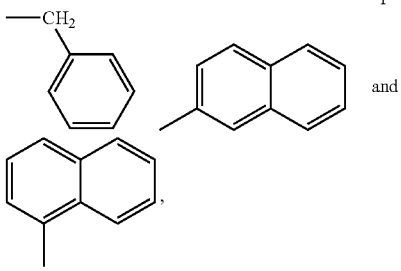

each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

More particularly preferred substituted 5,6,7,8-tetrahydro-imidazo[1,2-a]pyridin-2-ylamine compounds of the general formula I are those selected from the group consisting of

[1]   2-[(3-chloro-benzoyl)-methyl-amino]-5,6,7,8-tetrahydro-imidazo[1,2-a]pyridine-3-carboxylic   acid (2-thiophen-2-yl-ethyl)-amide,

[2] 2-[butyl-(3-chloro-benzoyl)-amino]-5,6,7,8-tetrahydro-imidazo[1,2-a]pyridine-3-carboxylic acid [2-(2,5-dimethoxy-phenyl)-ethyl]-amide,

[3] N-[3-[4-(2-ethyl-phenyl)-piperazine-1-carbonyl]-5,6,7,8-tetrahydro-imidazo[1,2-a]pyridin-2-yl]-N-methyl-benzamide,

[4] 2-(methyl-phenylacetyl-amino)-5,6,7,8-tetrahydro-imidazo[1,2-a]pyridine-3-carboxylic acid [3-(2-methyl-piperidin-1-yl)-propyl]-amide,

[5] 2-[(3-chloro-benzoyl)-methyl-amino]-5,6,7,8-tetrahydro-imidazo[1,2-a]pyridine-3-carboxylic acid (2-phenyl-propyl)-amide,

[6] 2-[(3-chloro-benzoyl)-methyl-amino]-5,6,7,8-tetrahydro-imidazo[1,2-a]pyridine-3-carboxylic acid (2-pyrrolidin-1-yl-ethyl)-amide,

[7] 2-[methyl-(naphthalene-1-carbonyl)-amino]-5,6,7,8-tetrahydro-imidazo[1,2-a]pyridine-3-carboxylic acid ethyl-pyridin-4-ylmethyl-amide,

[8] 2-(benzoyl-methyl-amino)-5,6,7,8-tetrahydro-imidazo[1,2-a]pyridine-3-carboxylic acid (2-thiophen-2-yl-ethyl)-amide,

[9] 2-[butyl-(3-chloro-benzoyl)-amino]-5,6,7,8-tetrahydro-imidazo[1,2-a]pyridine-3-carboxylic acid (3-imidazol-1-yl-propyl)-amide,

[10] 3-chloro-N-{3-[4-(3-chlorophenyl)-piperazine-1-carbonyl]-5,6,7,8-tetrahydro-imidazo[1,2-a]pyridin-2-yl}-N-methyl-benzamide,

[11] 3-chloro-N-methyl-N-[3-(4-phenyl-piperazine-1-carbonyl)-5,6,7,8-tetrahydro-imidazo[1,2-a]pyridin-2-yl]-benzamide,

[12] 2-[butyl-(3,4-difluorobenzoyl)-amino]-5,6,7,8-tetrahydro-imidazo[1,2-a]pyridine-3-carboxylic acid indan-1-ylamide,

[13] N-butyl-3-chloro-N-{3-[4-(2-morpholin-4-yl-ethyl)-piperazine-1-carbonyl]-5,6,7,8-tetrahydro-imidazo[1,2-a]pyridin-2-yl}-benzamide,

[14] 3-chloro-N-methyl-N-{3-[4-(3-trifluoromethyl-phenyl)-piperazine-1-carbonyl]-5,6,7,8-tetrahydro-imidazo[1,2-a]pyridin-2-yl}-benzamide,

[15] 2-[methyl-(naphthalene-1-carbonyl)-amino]-5,6,7,8-tetrahydro-imidazo[1,2-a]pyridine-3-carboxylic acid 3,5-bis-trifluoromethyl-benzylamide,

[16] 2-[butyl-(3,4-difluorobenzoyl)-amino]-5,6,7,8-tetrahydro-imidazo[1,2-a]pyridine-3-carboxylic acid (4-methyl-cyclohexyl)-amide,

[17] 2-(benzoyl-methyl-amino)-5,6,7,8-tetrahydro-imidazo[1,2-a]pyridine-3-carboxylic acid 3-methoxy-benzylamide,

[18] 2-[methyl-(naphthalene-1-carbonyl)-amino]-5,6,7,8-tetrahydro-imidazo[1,2-a]pyridine-3-carboxylic acid (1-p-tolyl-ethyl)-amide,

[19] 2-[butyl-(3-chloro-benzoyl)-amino]-5,6,7,8-tetrahydro-imidazo[1,2-a]pyridine-3-carboxylic acid (1,2-dimethyl-propyl)-amide,

[20] 2-(benzoyl-methyl-amino)-5,6,7,8-tetrahydro-imidazo[1,2-a]pyridine-3-carboxylic acid (4-methyl-cyclohexyl)-amide,

[21] 2-(benzoyl-methyl-amino)-5,6,7,8-tetrahydro-imidazo[1,2-a]pyridine-3-carboxylic acid (2-phenyl-propyl)-amide,

[22] 4-[2-(benzoyl-methyl-amino)-5,6,7,8-tetrahydro-imidazo[1,2-a]pyridine-3-carbonyl]-piperazine-1-carboxylic acid ethyl ester,

[23] 3-chloro-N-methyl-N-(3-{4-[(methyl-phenyl-carbamoyl)-methyl]-piperazine-1-carbonyl}-5,6,7,8-tetrahydro-imidazo[1,2-a]pyridin-2-yl)-benzamide,

[24] 3-chloro-N-{3-[4-(furan-2-carbonyl)-piperazine-1-carbonyl]-5,6,7,8-tetrahydro-imidazo[1,2-a]pyridin-2-yl}-N-methyl-benzamide,

[25] N-methyl-N-[3-(4-p-tolyl-piperazine-1-carbonyl)-5,6,7,8-tetrahydro-imidazo[1,2-a]pyridin-2-yl]-benzamide,

[26] N-butyl-3-chloro-N-{3-[4-(3-phenyl-propyl)-piperazine-1-carbonyl]-5,6,7,8-tetrahydro-imidazo[1,2-a]pyridin-2-yl}-benzamide,

[27] 2-[(3-chloro-benzoyl)-methyl-amino]-5,6,7,8-tetrahydro-imidazo[1,2-a]pyridine-3-carboxylic acid (2,6,6-trimethyl-bicyclo[3.1.1]hept-3-yl)-amide,

[28] 2-[butyl-(3,4-difluorobenzoyl)-amino]-5,6,7,8-tetrahydro-imidazo[1,2-a]pyridine-3-carboxylic acid (3-phenyl-propyl)-amide,

[29] naphthalene-1-carboxylic acid {3-[4-(4-methoxy-phenyl)-piperazine-1-carbonyl]-5,6,7,8-tetrahydro-imidazo[1,2-a]pyridin-2-yl}-methyl-amide,

[30] 2-[methyl-(naphthalene-1-carbonyl)-amino]-5,6,7,8-tetrahydro-imidazo[1,2-a]pyridine-3-carboxylic acid [1-(4-trifluoromethyl-benzyl)-pyrrolidin-3-yl]-amide,

[31] 2-[(3-chloro-benzoyl)-methyl-amino]-5,6,7,8-tetrahydro-imidazo[1,2-a]pyridine-3-carboxylic acid (4-ethyl-phenyl)-amide,

[32] 2-[methyl-(naphthalene-1-carbonyl)-amino]-5,6,7,8-tetrahydro-imidazo[1,2-a]pyridine-3-carboxylic acid (3-methoxy-benzyl)-(tetrahydro-furan-2-ylmethyl)-amide,

[33] 2-[methyl-(naphthalene-1-carbonyl)-amino]-5,6,7,8-tetrahydro-imidazo[1,2-a]pyridine-3-carboxylic acid 2,3-dichloro-benzylamide,

[34] 2-[butyl-(3,4-difluorobenzoyl)-amino]-5,6,7,8-tetrahydro-imidazo[1,2-a]pyridine-3-carboxylic acid (1-benzofuran-2-ylmethyl-pyrrolidin-3-yl)-methyl-amide,

[35] 3-chloro-N-{3-[4-(4-chlorophenyl)-piperazine-1-carbonyl]-5,6,7,8-tetrahydro-imidazo[1,2-a]pyridin-2-yl}-N-methyl-benzamide,

[36] 2-({2-[(3-chloro-benzoyl)-methyl-amino]-5,6,7,8-tetrahydro-imidazo[1,2-a]pyridine-3-carbonyl}-amino)-3-(1H-indol-3-yl)-propanoic acid methyl ester,

[37] N-butyl-3-chloro-N-[3-(4-phenylacetyl-piperazine-1-carbonyl)-5,6,7,8-tetrahydro-imidazo[1,2-a]pyridin-2-yl]-benzamide,

[38] 2-({2-[(3-chloro-benzoyl)-methyl-amino]-5,6,7,8-tetrahydro-imidazo[1,2-a]pyridine-3-carbonyl}-amino)-3-methyl-pentanoic acid-tert-butyl ester,

[39] 2-[butyl-(3-chloro-benzoyl)-amino]-5,6,7,8-tetrahydro-imidazo[1,2-a]pyridine-3-carboxylic acid (1-naphthalen-1-yl-ethyl)-amide,

[40] 2-[methyl-(naphthalene-1-carbonyl)-amino]-5,6,7,8-tetrahydro-imidazo[1,2-a]pyridine-3-carboxylic acid allyl-methyl-amide,

[41] N-butyl-N-[3-(3,6-dihydro-2H-pyridine-1-carbonyl)-5,6,7,8-tetrahydro-imidazo[1,2-a]pyridin-2-yl]-3,4-difluoro-benzamide,

[42] 2-({2-[(3-chloro-benzoyl)-methyl-amino]-5,6,7,8-tetrahydro-imidazo[1,2-a]pyridine-3-carbonyl}-amino)-4-methyl-pentanoic acid-benzyl ester,

[43] 2-[butyl-(3-chloro-benzoyl)-amino]-5,6,7,8-tetrahydro-imidazo[1,2-a]pyridine-3-carboxylic acid 2-ethoxy-benzylamide,

[44] N-butyl-3-chloro-N-{3-[4-(5-methyl-pyrazine-2-carbonyl)-piperazine-1-carbonyl]-5,6,7,8-tetrahydro-imidazo[1,2-a]pyridin-2-yl}-benzamide,

[45] N-[3-(4-benzo[1,3]dioxol-5-ylmethyl-piperazine-1-carbonyl)-5,6,7,8-tetrahydro-imidazo[1,2-a]pyridin-2-yl]-3-chloro-N-methyl-benzamide,

[46] 2-[methyl-(naphthalene-1-carbonyl)-amino]-5,6,7,8-tetrahydro-imidazo[1,2-a]pyridine-3-carboxylic acid (2,2-diphenyl-ethyl)-amide,
[47] 2-[butyl-(3-chloro-benzoyl)-amino]-5,6,7,8-tetrahydro-imidazo[1,2-a]pyridine-3-carboxylic acid 2,4-difluoro-benzylamide,
[48] N-butyl-3-chloro-N-{3-[4-(2-fluoro-phenyl)-piperazine-1-carbonyl]-5,6,7,8-tetrahydro-imidazo[1,2-a]pyridin-2-yl}-benzamide,
[49] 2-[methyl-(naphthalene-1-carbonyl)-amino]-5,6,7,8-tetrahydro-imidazo[1,2-a]pyridine-3-carboxylic acid (2-p-tolyl-ethyl)-amide,
[50] 2-[methyl-(naphthalene-1-carbonyl)-amino]-5,6,7,8-tetrahydro-imidazo[1,2-a]pyridine-3-carboxylic acid (pyridin-2-ylmethyl)-amide,
[51] 2-[butyl-(3-chloro-benzoyl)-amino]-5,6,7,8-tetrahydro-imidazo[1,2-a]pyridine-3-carboxylic acid 2-trifluoromethyl-benzylamide,
[52] 2-[butyl-(3-chloro-benzoyl)-amino]-5,6,7,8-tetrahydro-imidazo[1,2-a]pyridine-3-carboxylic acid indan-1-ylamide,
[53] 3-chloro-N-methyl-N-[3-(4-quinolin-2-ylmethyl-piperazine-1-carbonyl)-5,6,7,8-tetrahydro-imidazo[1,2-a]pyridin-2-yl]-benzamide,
[54] N-butyl-3,4-difluoro-N-[3-(4-methyl-piperazine-1-carbonyl)-5,6,7,8-tetrahydro-imidazo[1,2-a]pyridin-2-yl]-benzamide,
[55] 2-[(3-chloro-benzoyl)-methyl-amino]-5,6,7,8-tetrahydro-imidazo[1,2-a]pyridine-3-carboxylic acid 2,4-difluoro-benzylamide,
[56] N-[3-(4-benzhydryl-piperazine-1-carbonyl)-5,6,7,8-tetrahydro-imidazo[1,2-a]pyridin-2-yl]-N-butyl-3,4-difluoro-benzamide,
[57] 4-methyl-2-({2-[methyl-(naphthalene-1-carbonyl)-amino]-5,6,7,8-tetrahydro-imidazo[1,2-a]pyridine-3-carbonyl}-amino)-pentanoic acid-benzyl ester,
[58] 2-[butyl-(3-chloro-benzoyl)-amino]-5,6,7,8-tetrahydro-imidazo[1,2-a]pyridine-3-carboxylic acid (2-pyrrolidin-1-yl-ethyl)-amide,
[59] 2-[(3-chloro-benzoyl)-methyl-amino]-5,6,7,8-tetrahydro-imidazo[1,2-a]pyridine-3-carboxylic acid [1-(2-benzyloxy-benzyl)-pyrrolidin-3-yl]-amide,
[60] 2-[butyl-(3,4-difluorobenzoyl)-amino]-5,6,7,8-tetrahydro-imidazo[1,2-a]pyridine-3-carboxylic acid (pyridin-3-ylmethyl)-amide,
[61] 3-chloro-N-{3-[4-(4-fluorophenyl)-3,6-dihydro-2H-pyridine-1-carbonyl]-5,6,7,8-tetrahydro-imidazo[1,2-a]pyridin-2-yl}-N-methyl-benzamide,
[62] 2-[(3-chloro-benzoyl)-methyl-amino]-5,6,7,8-tetrahydro-imidazo[1,2-a]pyridine-3-carboxylic acid cyclohexylamide,
[63] N-[3-(4-cycloheptyl-piperazine-1-carbonyl)-5,6,7,8-tetrahydro-imidazo[1,2-a]pyridin-2-yl]-N-methyl-benzamide,
[64] naphthalene-1-carboxylic acid methyl-[3-(4-thiophen-3-ylmethyl-piperazine-1-carbonyl)-5,6,7,8-tetrahydro-imidazo[1,2-a]pyridin-2-yl]-amide,
[65] 2-[butyl-(3-chloro-benzoyl)-amino]-5,6,7,8-tetrahydro-imidazo[1,2-a]pyridine-3-carboxylic acid 2,4-dimethoxy-benzylamide,
[66] 1-[2-(benzoyl-methyl-amino)-5,6,7,8-tetrahydro-imidazo[1,2-a]pyridine-3-carbonyl]-piperidine-4-carboxylic acid ethyl ester,
[67] 2-[(3-chloro-benzoyl)-methyl-amino]-5,6,7,8-tetrahydro-imidazo[1,2-a]pyridine-3-carboxylic acid (2-benzyloxy-cyclohexyl)-amide,
[68] 2-[methyl-(naphthalene-1-carbonyl)-amino]-5,6,7,8-tetrahydro-imidazo[1,2-a]pyridine-3-carboxylic acid [2-(4-phenoxy-phenyl)-ethyl]-amide,
[69] 2-[butyl-(3-chloro-benzoyl)-amino]-5,6,7,8-tetrahydro-imidazo[1,2-a]pyridine-3-carboxylic acid [2-(7-methyl-1H-indol-3-yl)-ethyl]-amide,
[70] naphthalene-1-carboxylic acid methyl-[3-(4-phenyl-piperazine-1-carbonyl)-5,6,7,8-tetrahydro-imidazo[1,2-a]pyridin-2-yl]-amide,
[71] 2-[(3-chloro-benzoyl)-methyl-amino]-5,6,7,8-tetrahydro-imidazo[1,2-a]pyridine-3-carboxylic acid [2-(3-trifluoromethyl-phenyl)-ethyl]-amide,
[72] N-butyl-3-chloro-N-[3-(4-pyridin-2-yl-piperazine-1-carbonyl)-5,6,7,8-tetrahydro-imidazo[1,2-a]pyridin-2-yl]-benzamide,
[73] 2-[methyl-(naphthalene-1-carbonyl)-amino]-5,6,7,8-tetrahydro-imidazo[1,2-a]pyridine-3-carboxylic acid 3-methoxy-benzylamide,
[74] 2-[butyl-(3,4-difluorobenzoyl)-amino]-5,6,7,8-tetrahydro-imidazo[1,2-a]pyridine-3-carboxylic acid 2,4-difluoro-benzylamide,
[75] 3-chloro-N-methyl-N-[3-(4-pyridin-2-yl-piperazine-1-carbonyl)-5,6,7,8-tetrahydro-imidazo[1,2-a]pyridin-2-yl]-benzamide,
[76] 2-[methyl-(naphthalene-1-carbonyl)-amino]-5,6,7,8-tetrahydro-imidazo[1,2-a]pyridine-3-carboxylic acid (1-biphenyl-4-ylmethyl-pyrrolidin-3-yl)-methyl-amide,
[77] 2-[butyl-(3-chloro-benzoyl)-amino]-5,6,7,8-tetrahydro-imidazo[1,2-a]pyridine-3-carboxylic acid (2,3-dihydro-benzo[1,4]dioxin-2-ylmethyl)-amide,
[78] 2-[butyl-(3-chloro-benzoyl)-amino]-5,6,7,8-tetrahydro-imidazo[1,2-a]pyridine-3-carboxylic acid [2-(1H-indol-3-yl)-ethyl]-methyl-amide,
[79] N-butyl-3-chloro-N-{3-[4-(3-trifluoromethyl-phenyl)-piperazine-1-carbonyl]-5,6,7,8-tetrahydro-imidazo[1,2-a]pyridin-2-yl}-benzamide,
[80] 2-(benzoyl-methyl-amino)-5,6,7,8-tetrahydro-imidazo[1,2-a]pyridine-3-carboxylic acid [2-(1H-indol-3-yl)-ethyl]-methyl-amide,
[81] 3-chloro-N-{3-[4-hydroxy-4-(3-trifluoromethyl-phenyl)-piperidine-1-carbonyl]-5,6,7,8-tetrahydro-imidazo[1,2-a]pyridin-2-yl}-N-methyl-benzamide,
[82] 2-[butyl-(3,4-difluoro-benzoyl)-amino]-5,6,7,8-tetrahydro-imidazo[1,2-a]pyridine-3-carboxylic acid (1-methoxymethyl-2-phenyl-ethyl)-amide,
[83] 2-[(3-chloro-benzoyl)-methyl-amino]-5,6,7,8-tetrahydro-imidazo[1,2-a]pyridine-3-carboxylic acid [1-(2,6-dichloro-benzyl)-pyrrolidin-3-yl]-amide,
[84] 2-[(3-chloro-benzoyl)-methyl-amino]-5,6,7,8-tetrahydro-imidazo[1,2-a]pyridine-3-carboxylic acid [1-(2-bromo-4,5-dimethoxy-benzyl)-pyrrolidin-3-yl]-amide,
[85] 2-(benzoyl-methyl-amino)-5,6,7,8-tetrahydro-imidazo[1,2-a]pyridine-3-carboxylic acid benzo[1,3]dioxol-5-ylamide,
[86] 2-[butyl-(3-chloro-benzoyl)-amino]-5,6,7,8-tetrahydro-imidazo[1,2-a]pyridine-3-carboxylic acid (1-methoxymethyl-2-phenyl-ethyl)-amide,
[87] 2-[butyl-(3-chloro-benzoyl)-amino]-5,6,7,8-tetrahydro-imidazo[1,2-a]pyridine-3-carboxylic acid [1-(2,6-dichloro-benzyl)-pyrrolidin-3-yl]-methyl-amide,
[88] 2-[butyl-(3,4-difluorobenzoyl)-amino]-5,6,7,8-tetrahydro-imidazo[1,2-a]pyridine-3-carboxylic acid 2-trifluoromethoxy-benzylamide,
[89] N-butyl-3,4-difluoro-N-{3-[4-(isopropylcarbamoyl-methyl)-piperazine-1-carbonyl]-5,6,7,8-tetrahydro-imidazo[1,2-a]pyridin-2-yl}-benzamide,

[90] 2-[(3-Chloro-benzoyl)-methyl-amino]-5,6,7,8-tetrahydro-imidazo[1,2-a]pyridine-3-carboxylic acid (1-methyl-3-phenyl-propyl)-amide,

[91] 2-({2-[butyl-(3-chloro-benzoyl)-amino]-5,6,7,8-tetrahydro-imidazo[1,2-a]pyridine-3-carbonyl}-amino)-3-methyl-ethyl butyrate,

[92] 2-[(3-chloro-benzoyl)-methyl-amino]-5,6,7,8-tetrahydro-imidazo[1,2-a]pyridine-3-carboxylic acid (thiophen-2-ylmethyl)-amide,

[93] 2-[butyl-(3,4-difluorobenzoyl)-amino]-5,6,7,8-tetrahydro-imidazo[1,2-a]pyridine-3-carboxylic acid (2-methyl-cyclohexyl)-amide,

[94] 2-(benzoyl-methyl-amino)-5,6,7,8-tetrahydro-imidazo[1,2-a]pyridine-3-carboxylic acid benzyl-methyl-amide,

[95] 2-[butyl-(3-chloro-benzoyl)-amino]-5,6,7,8-tetrahydro-imidazo[1,2-a]pyridine-3-carboxylic acid [2-(2,6-dichloro-benzylsulphanyl)-ethyl]-amide,

[96] 2-[butyl-(3,4-difluorobenzoyl)-amino]-5,6,7,8-tetrahydro-imidazo[1,2-a]pyridine-3-carboxylic acid (2,3-dihydro-benzo[1,4]dioxin-2-ylmethyl)-amide,

[97] 2-[(3-chloro-benzoyl)-methyl-amino]-5,6,7,8-tetrahydro-imidazo[1,2-a]pyridine-3-carboxylic acid 4-trifluoromethyl-benzylamide,

[98] N-[3-(4-benzyl-piperidine-1-carbonyl)-5,6,7,8-tetrahydro-imidazo[1,2-a]pyridin-2-yl]-N-methyl-benzamide,

[99] 2-[methyl-(naphthalene-1-carbonyl)-amino]-5,6,7,8-tetrahydro-imidazo[1,2-a]pyridine-3-carboxylic acid 2-trifluoromethoxy-benzylamide,

[100] 3-chloro-N-{3-[4-(2,5-dimethyl-phenyl)-piperazine-1-carbonyl]-5,6,7,8-tetrahydro-imidazo[1,2-a]pyridin-2-yl}-N-methyl-benzamide,

[101] 2-(benzoyl-methyl-amino)-5,6,7,8-tetrahydro-imidazo[1,2-a]pyridine-3-carboxylic acid [1-(2,6-dichloro-benzyl)-pyrrolidin-3-yl]-amide,

[102] 2-[butyl-(3,4-difluorobenzoyl)-amino]-5,6,7,8-tetrahydro-imidazo[1,2-a]pyridine-3-carboxylic acid 2-chloro-6-methyl-benzylamide,

[103] N-butyl-3-chloro-N-[3-(3,5-dimethyl-piperidine-1-carbonyl)-5,6,7,8-tetrahydro-imidazo[1,2-a]pyridin-2-yl]-benzamide,

[104] 2-({2-[(3-chloro-benzoyl)-methyl-amino]-5,6,7,8-tetrahydro-imidazo[1,2-a]pyridine-3-carbonyl}-amino)-3,3-dimethyl-butyric acid tert-butylester,

[105] 2-[methyl-(naphthalene-1-carbonyl)-amino]-5,6,7,8-tetrahydro-imidazo[1,2-a]pyridine-3-carboxylic acid (1-cyclohexyl-ethyl)-amide,

[106] 3-chloro-N-methyl-N-[3-(4-phenethyl-piperazine-1-carbonyl)-5,6,7,8-tetrahydro-imidazo[1,2-a]pyridin-2-yl]-benzamide,

[107] 2-[butyl-(3-chloro-benzoyl)-amino]-5,6,7,8-tetrahydro-imidazo[1,2-a]pyridine-3-carboxylic acid (2-phenoxy-ethyl)-amide,

[108] naphthalene-1-carboxylic acid [3-(4-benzofuran-2-yl-methyl-piperazine-1-carbonyl)-5,6,7,8-tetrahydro-imidazo[1,2-a]pyridin-2-yl]-methyl-amide,

[109] N-[3-([1,4']bipiperidinyl-1'-carbonyl)-5,6,7,8-tetrahydro-imidazo[1,2-a]pyridin-2-yl]-N-butyl-3-chloro-benzamide,

[110] N-butyl-3-chloro-N-[3-(8-fluoro-1,3,4,5-tetrahydropyrido[4,3-b]indole-2-carbonyl)-5,6,7,8-tetrahydro-imidazo[1,2-a]pyridin-2-yl]-benzamide,

[111] 2-[methyl-(naphthalene-1-carbonyl)-amino]-5,6,7,8-tetrahydro-imidazo[1,2-a]pyridine-3-carboxylic acid 4-dimethylamino-benzylamide,

[112] 2-[methyl-(naphthalene-1-carbonyl)-amino]-5,6,7,8-tetrahydro-imidazo[1,2-a]pyridine-3-carboxylic acid (1-methyl-3-phenyl-propyl)-amide,

[113] 2-[butyl-(3-chloro-benzoyl)-amino]-5,6,7,8-tetrahydro-imidazo[1,2-a]pyridine-3-carboxylic acid 3-methyl-benzylamide,

[114] 2-[(3-chloro-benzoyl)-methyl-amino]-5,6,7,8-tetrahydro-imidazo[1,2-a]pyridine-3-carboxylic acid (2,3-dihydro-benzo[1,4]dioxin-6-yl)-amide,

[115] naphthalene-1-carboxylic acid methyl-[3-(4-quinolin-2-ylmethyl-piperazine-1-carbonyl)-5,6,7,8-tetrahydro-imidazo[1,2-a]pyridin-2-yl]-amide,

[116] 2-[butyl-(3,4-difluorobenzoyl)-amino]-5,6,7,8-tetrahydro-imidazo[1,2-a]pyridine-3-carboxylic acid (2-cyano-ethyl)-methyl-amide,

[117] 2-(methyl-phenylacetyl-amino)-5,6,7,8-tetrahydro-imidazo[1,2-a]pyridine-3-carboxylic acid (2-p-tolyl-ethyl)-amide,

[118] 2-[butyl-(3,4-difluorobenzoyl)-amino]-5,6,7,8-tetrahydro-imidazo[1,2-a]pyridine-3-carboxylic acid [1-(4-fluoro-phenyl)-ethyl]-amide,

[119] N-butyl-N-{3-[4-(5-chloro-2-methyl-phenyl)-piperazine-1-carbonyl]-5,6,7,8-tetrahydro-imidazo[1,2-a]pyridin-2-yl}-3,4-difluoro-benzamide,

[120] 2-[butyl-(3-chloro-benzoyl)-amino]-5,6,7,8-tetrahydro-imidazo[1,2-a]pyridine-3-carboxylic acid cyclohexylamide,

[121] 2-[(3-chloro-benzoyl)-methyl-amino]-5,6,7,8-tetrahydro-imidazo[1,2-a]pyridine-3-carboxylic acid (benzo[1,3]dioxol-5-ylmethyl)-amide,

[122] 2-[butyl-(3,4-difluorobenzoyl)-amino]-5,6,7,8-tetrahydro-imidazo[1,2-a]pyridine-3-carboxylic acid 3-methoxy-benzylamide,

[123] 3-tert-butoxy-2-({2-[(3-chloro-benzoyl)-methyl-amino]-5,6,7,8-tetrahydro-imidazo[1,2-a]pyridine-3-carbonyl}-amino)-methyl butyrate,

[124] 2-[butyl-(3-chloro-benzoyl)-amino]-5,6,7,8-tetrahydro-imidazo[1,2-a]pyridine-3-carboxylic acid (2-benzyloxy-cyclohexyl)-amide,

[125] N-{3-[4-(4-fluoro-phenyl)-piperazine-1-carbonyl]-5,6,7,8-tetrahydro-imidazo[1,2-a]pyridin-2-yl}-N-methyl-benzamide,

[126] 2-(benzoyl-methyl-amino)-5,6,7,8-tetrahydro-imidazo[1,2-a]pyridine-3-carboxylic acid (naphthalen-2-ylcarbamoylmethyl)-amide,

[127] 2-[butyl-(3-chloro-benzoyl)-amino]-5,6,7,8-tetrahydro-imidazo[1,2-a]pyridine-3-carboxylic acid 4-trifluoromethoxy-benzylamide,

[128] 2-[(3-chloro-benzoyl)-methyl-amino]-5,6,7,8-tetrahydro-imidazo[1,2-a]pyridine-3-carboxylic acid (3,3-diphenyl-propyl)-amide,

[129] 2-[(3-chloro-benzoyl)-methyl-amino]-5,6,7,8-tetrahydro-imidazo[1,2-a]pyridine-3-carboxylic acid (4-benzyloxy-phenyl)-amide,

[130] N-{3-[4-(5-bromo-2-ethoxy-benzyl)-piperazine-1-carbonyl]-5,6,7,8-tetrahydro-imidazo[1,2-a]pyridin-2-yl}-N-methyl-2-phenyl-acetamide,

[131] N-[3-(3,4-dihydro-1H-isoquinoline-2-carbonyl)-5,6,7,8-tetrahydro-imidazo[1,2-a]pyridin-2-yl]-N-methyl-benzamide,

[132] 2-[butyl-(3-chloro-benzoyl)-amino]-5,6,7,8-tetrahydro-imidazo[1,2-a]pyridine-3-carboxylic acid (1-phenyl-propyl)-amide,

[133] 2-[butyl-(3-chloro-benzoyl)-amino]-5,6,7,8-tetrahydro-imidazo[1,2-a]pyridine-3-carboxylic acid 2,3-dimethyl-benzylamide,

[134] 2-[butyl-(3-chloro-benzoyl)-amino]-5,6,7,8-tetrahydro-imidazo[1,2-a]pyridine-3-carboxylic acid [2-(4-phenoxy-phenyl)-ethyl]-amide,

[135] N-{3-[4-(4-ethoxy-phenyl)-piperazine-1-carbonyl]-5,6,7,8-tetrahydro-imidazo[1,2-a]pyridin-2-yl}-N-methyl-2-phenyl-acetamide,

[136] naphthalene-1-carboxylic acid {3-[4-(2-ethyl-phenyl)-piperazine-1-carbonyl]-5,6,7,8-tetrahydro-imidazo[1,2-a]pyridin-2-yl}-methyl-amide,

[137] N-[3-(4-benzo[1,3]dioxol-5-ylmethyl-piperazine-1-carbonyl)-5,6,7,8-tetrahydro-imidazo[1,2-a]pyridin-2-yl]-N-butyl-3,4-difluoro-benzamide,

[138] N-butyl-N-{3-[4-(2,5-dimethyl-phenyl)-piperazine-1-carbonyl]-5,6,7,8-tetrahydro-imidazo[1,2-a]pyridin-2-yl}-3,4-difluoro-benzamide,

[139] 2-[methyl-(naphthalene-1-carbonyl)-amino]-5,6,7,8-tetrahydro-imidazo[1,2-a]pyridine-3-carboxylic acid [(4-chloro-phenyl)-phenyl-methyl]-amide,

[140] N-butyl-3-chloro-N-{3-[4-(4-chloro-benzyl)-piperazine-1-carbonyl]-5,6,7,8-tetrahydro-imidazo[1,2-a]pyridin-2-yl}-benzamide,

[141] 2-[butyl-(3-chloro-benzoyl)-amino]-5,6,7,8-tetrahydro-imidazo[1,2-a]pyridine-3-carboxylic acid (1-naphthalen-2-yl-ethyl)-amide,

[142] 2-(methyl-phenylacetyl-amino)-5,6,7,8-tetrahydro-imidazo[1,2-a]pyridine-3-carboxylic acid 2-fluoro-benzylamide,

[143] N-[3-(1,4-dioxa-8-aza-spiro[4.5]decane-8-carbonyl)-5,6,7,8-tetrahydro-imidazo[1,2-a]pyridin-2-yl]-N-methyl-2-phenyl-acetamide,

[144] naphthalene-1-carboxylic acid methyl-[3-(1,3,4,9-tetrahydro-b-carboline-2-carbonyl)-5,6,7,8-tetrahydro-imidazo[1,2-a]pyridin-2-yl]-amide,

[145] 2-[butyl-(3-chloro-benzoyl)-amino]-5,6,7,8-tetrahydro-imidazo[1,2-a]pyridine-3-carboxylic acid (1-methyl-3-phenyl-propyl)-amide,

[146] 3-chloro-N-methyl-N-{3-[4-(2,4,6-trimethoxy-benzyl)-piperazine-1-carbonyl]-5,6,7,8-tetrahydro-imidazo[1,2-a]pyridin-2-yl}-benzamide,

[147] 2-[butyl-(3-chloro-benzoyl)-amino]-5,6,7,8-tetrahydro-imidazo[1,2-a]pyridine-3-carboxylic acid benzhydryl-amide,

[148] naphthalene-1-carboxylic acid {3-[4-(2-chloro-phenyl)-piperazine-1-carbonyl]-5,6,7,8-tetrahydro-imidazo[1,2-a]pyridin-2-yl}-methyl-amide,

[149] 2-[butyl-(3-chloro-benzoyl)-amino]-5,6,7,8-tetrahydro-imidazo[1,2-a]pyridine-3-carboxylic acid (thiophen-2-ylmethyl)-amide,

[150] N-butyl-N-{3-[4-(4-chlorobenzyl)-piperazine-1-carbonyl]-5,6,7,8-tetrahydro-imidazo[1,2-a]pyridin-2-yl}-3,4-difluoro-benzamide,

[151] 2-(benzoyl-methyl-amino)-5,6,7,8-tetrahydro-imidazo[1,2-a]pyridine-3-carboxylic acid (3-phenyl-propyl)-amide,

[152] 2-[butyl-(3-chloro-benzoyl)-amino]-5,6,7,8-tetrahydro-imidazo[1,2-a]pyridine-3-carboxylic acid (4-tert-butyl-phenyl)-amide,

[153] 2-[butyl-(3-chloro-benzoyl)-amino]-5,6,7,8-tetrahydro-imidazo[1,2-a]pyridine-3-carboxylic acid (4-ethyl-phenyl)-amide,

[154] 2-[methyl-(naphthalene-1-carbonyl)-amino]-5,6,7,8-tetrahydro-imidazo[1,2-a]pyridine-3-carboxylic acid cyclohexylamide,

[155] 2-[methyl-(naphthalene-1-carbonyl)-amino]-5,6,7,8-tetrahydro-imidazo[1,2-a]pyridine-3-carboxylic acid [3-(methyl-phenyl-amino)-propyl]-amide,

[156] 2-(methyl-phenylacetyl-amino)-5,6,7,8-tetrahydro-imidazo[1,2-a]pyridine-3-carboxylic acid [2-(3-trifluormethyl-phenyl)-ethyl]-amide,

[157] 2-(benzoyl-methyl-amino)-5,6,7,8-tetrahydro-imidazo[1,2-a]pyridine-3-carboxylic acid 4-chloro-benzylamide,

[158] 2-[butyl-(3-chloro-benzoyl)-amino]-5,6,7,8-tetrahydro-imidazo[1,2-a]pyridine-3-carboxylic acid 3-fluoro-benzylamide,

[159] 2-(methyl-phenylacetyl-amino)-5,6,7,8-tetrahydro-imidazo[1,2-a]pyridine-3-carboxylic acid p-tolylamide,

[160] 2-(benzoyl-methyl-amino)-5,6,7,8-tetrahydro-imidazo[1,2-a]pyridine-3-carboxylic acid (2-phenoxy-ethyl)-amide,

[161] 2-[butyl-(3,4-difluorobenzoyl)-amino]-5,6,7,8-tetrahydro-imidazo[1,2-a]pyridine-3-carboxylic acid (2-benzyloxy-cyclohexyl)-amide,

[162] naphthalene-1-carboxylic acid {3-[4-(4-fluoro-phenyl)-piperazine-1-carbonyl]-5,6,7,8-tetrahydro-imidazo[1,2-a]pyridin-2-yl}-methyl-amide,

[163] 2-[methyl-(naphthalene-1-carbonyl)-amino]-5,6,7,8-tetrahydro-imidazo[1,2-a]pyridine-3-carboxylic acid [2-(4-chloro-phenyl)-propyl]-amide,

[164] N-butyl-3,4-difluoro-N-[3-(thiomorpholine-4-carbonyl)-5,6,7,8-tetrahydro-imidazo[1,2-a]pyridin-2-yl]-benzamide,

[165] 2-[(3-chloro-benzoyl)-methyl-amino]-5,6,7,8-tetrahydro-imidazo[1,2-a]pyridine-3-carboxylic acid (1-adamantan-1-yl-ethyl)-amide,

[166] 2-(benzoyl-methyl-amino)-5,6,7,8-tetrahydro-imidazo[1,2-a]pyridine-3-carboxylic acid [(4-chloro-phenyl)-phenyl-methyl]-amide,

[167] N-methyl-N-{3-[4-(4-trifluoromethyl-phenyl)-piperazine-1-carbonyl]-5,6,7,8-tetrahydro-imidazo[1,2-a]pyridin-2-yl}-benzamide,

[168] 2-(methyl-phenylacetyl-amino)-5,6,7,8-tetrahydro-imidazo[1,2-a]pyridine-3-carboxylic acid (1-biphenyl-4-ylmethyl-pyrrolidin-3-yl)-methyl-amide,

[169] N-[3-(4-benzoyl-piperidine-1-carbonyl)-5,6,7,8-tetrahydro-imidazo[1,2-a]pyridin-2-yl]-3-chloro-N-methyl-benzamide,

[170] 2-[methyl-(naphthalene-1-carbonyl)-amino]-5,6,7,8-tetrahydro-imidazo[1,2-a]pyridine-3-carboxylic acid (4-tert-butyl-phenyl)-amide,

[171] 2-[butyl-(3,4-difluoro-benzoyl)-amino]-5,6,7,8-tetrahydro-imidazo[1,2-a]pyridine-3-carboxylic acid (3,3-dimethyl-butyl)-amide,

[172] 2-[butyl-(3-chloro-benzoyl)-amino]-5,6,7,8-tetrahydro-imidazo[1,2-a]pyridine-3-carboxylic acid [1-(2-bromo-4,5-dimethoxy-benzyl)-pyrrolidin-3-yl]-amide,

[173] naphthalene-1-carboxylic acid methyl-{3-[4-(3-phenyl-allyl)-piperazine-1-carbonyl]-5,6,7,8-tetrahydro-imidazo[1,2-a]pyridin-2-yl}-amide,

[174] naphthalene-1-carboxylic acid methyl-[3-(4-phenethyl-piperazine-1-carbonyl)-5,6,7,8-tetrahydro-imidazo[1,2-a]pyridin-2-yl]-amide,

[175] N-butyl-3-chloro-N-{3-[4-hydroxy-4-(3-trifluormethyl-phenyl)-piperidine-1-carbonyl]-5,6,7,8-tetrahydro-imidazo[1,2-a]pyridin-2-yl}-benzamide,

[176] N-methyl-2-phenyl-N-{3-[4-(3-phenyl-propyl)-piperazine-1-carbonyl]-5,6,7,8-tetrahydro-imidazo[1,2-a]pyridin-2-yl}-acetamide,

[177] 2-(benzoyl-methyl-amino)-5,6,7,8-tetrahydro-imidazo[1,2-a]pyridine-3-carboxylic acid 3-fluoro-benzylamide,

[178] N-butyl-N-{3-[4-(2-chlorophenyl)-piperazine-1-carbonyl]-5,6,7,8-tetrahydro-imidazo[1,2-a]pyridin-2-yl}-3,4-difluoro-benzamide,

[179] 2-[methyl-(naphthalene-1-carbonyl)-amino]-5,6,7,8-tetrahydro-imidazo[1,2-a]pyridine-3-carboxylic acid benzo[1,3]dioxol-5-ylamide,

[180] 2-[butyl-(3,4-difluorobenzoyl)-amino]-5,6,7,8-tetrahydro-imidazo[1,2-a]pyridine-3-carboxylic acid (3,3-diphenyl-propyl)-amide,

[181] 2-[butyl-(3-chloro-benzoyl)-amino]-5,6,7,8-tetrahydro-imidazo[1,2-a]pyridine-3-carboxylic acid (2,3-dihydro-benzo[1,4]dioxin-6-yl)-amide,

[182] 2-(benzoyl-methyl-amino)-5,6,7,8-tetrahydro-imidazo[1,2-a]pyridine-3-carboxylic acid [2-(3,4-dimethoxy-phenyl)-ethyl]-amide,

[183] naphthalene-1-carboxylic acid [3-(4-benzoyl-piperidine-1-carbonyl)-5,6,7,8-tetrahydro-imidazo[1,2-a]pyridin-2-yl]-methyl-amide,

[184] 4-methyl-2-({2-[methyl-(naphthalene-1-carbonyl)-amino]-5,6,7,8-tetrahydro-imidazo[1,2-a]pyridine-3-carbonyl}-amino)-valeric acid tert-butylester,

[185] 2-[methyl-(naphthalene-1-carbonyl)-amino]-5,6,7,8-tetrahydro-imidazo[1,2-a]pyridine-3-carboxylic acid (4-phenoxy-phenyl)-amide,

[186] N-methyl-2-phenyl-N-[3-(4-phenyl-piperazine-1-carbonyl)-5,6,7,8-tetrahydro-imidazo[1,2-a]pyridin-2-yl]-acetamide,

[187] N-butyl-3,4-difluoro-N-{3-[4-(5-trifluoromethyl-pyridin-2-yl)-piperazine-1-carbonyl]-5,6,7,8-tetrahydro-imidazo[1,2-a]pyridin-2-yl}-benzamide,

[188] 2-(benzoyl-methyl-amino)-5,6,7,8-tetrahydro-imidazo[1,2-a]pyridine-3-carboxylic acid 2,4-dichloro-6-methyl-benzylamide,

[189] [4-({2-[butyl-(3-chloro-benzoyl)-amino]-5,6,7,8-tetrahydro-imidazo[1,2-a]pyridine-3-carbonyl}-amino)-phenyl]-carbamic acid tert-butyl ester,

[190] N-methyl-2-phenyl-N-[3-(2-pyrrolidin-1-ylmethyl-pyrrolidine-1-carbonyl)-5,6,7,8-tetrahydro-imidazo[1,2-a]pyridin-2-yl]-acetamide and 4-[2-(methyl-phenylacetyl-amino)-5,6,7,8-tetrahydro-imidazo[1,2-a]pyridine-3-carbonyl]-piperazine-1-carboxylic acid tert-butyl ester, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of corresponding salts or each in the form of corresponding solvates.

Similarly preferred are substituted 5,6,7,8-tetrahydro-imidazo[1,2-a]pyridin-2-ylamine compounds of the general formula I according to the invention which inhibit the $Ca^{2+}$ ion influx in the dorsal root ganglia of rats by at least 30%, preferably by at least 50%, particularly preferably by at least 70%, more particularly preferably by at least 80% and most particularly preferably by at least 90% in the FLIPR assay at a concentration of 10 µM, in comparison with the maximum level of inhibition of the $Ca^{2+}$ ion influx of capsaicin at a concentration of 10 µM.

This was quantified in the FLIPR assay of the $Ca^{2+}$ influx by means of a $Ca^{2+}$-sensitive dye (Fluo-4, Molecular Probes Europe BV, Leiden, The Netherlands) in the fluorescent imaging plate reader (FLIPR, Molecular Devices, Sunnyvale, USA), as described below.

The present invention further relates to a method for preparing compounds of the aforementioned general formula I according to the invention, according to which at least a compound of the general formula II,

II in which R represents a linear or branched $C_{1-6}$ alkyl radical, preferably a methyl or ethyl radical, is reacted in a reaction medium in the presence of at least a reducing agent, optionally in the presence of at least an organic acid, preferably in the presence of acetic acid, with at least a compound of the general formula $R^3$—C(=O)—H, in which $R^3$ is as defined hereinbefore with the exception of the hydrogen radical, to form a compound of the general formula III,

III in which R is defined as hereinbefore and $R^3$ is as defined hereinbefore with the exception of the hydrogen radical, and said compound is optionally purified and/or isolated, and at least a compound of the general formula III is reacted in a reaction medium, optionally in the presence of at least a base, with at least a compound of the general formula $R^4$—C(=O)—X, in which $R^4$ is as defined hereinbefore and X represents a leaving group, preferably a halogen radical, particularly preferably a chlorine or bromine atom, or in a reaction medium in the presence of at least a coupling reagent, optionally in the presence at least of a base, with a compound of the general formula $R^4$—C(=O)—OH, in which $R^4$ is as defined hereinbefore, to form a compound of the general formula IV,

IV in which R and $R^4$ are as defined hereinbefore and $R^3$ is as defined hereinbefore with the exception of the hydrogen radical, and said compound is optionally purified and/or isolated, or at least a compound of the general formula II, in which R is as defined hereinbefore, is reacted in a reaction medium, optionally in the presence of at least a base, with at least a compound of the general formula $R^4$—C(=O)—X, in which $R^4$ is as defined hereinbefore and X represents a leaving group, preferably a halogen radical, particularly preferably a chlorine or bromine atom, or in a reaction medium in the presence of at least a coupling reagent, optionally in the presence of at least a base, with a compound of the general formula $R^4$—C(=O)—OH, in which $R^4$ is as defined hereinbefore, to form a compound of the general formula V,

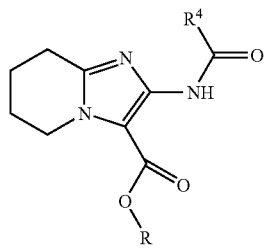

V in which R and $R^4$ are as defined hereinbefore, and said compound is optionally purified and/or isolated and at least a compound of the general formula V is reacted in a reaction medium in the presence of at least a base, preferably at least a metal hydride, with at least a compound of the general formula $R^3$—X, in which $R^3$ is as defined hereinbefore with the exception of the hydrogen radical and X represents a leaving group, preferably a halogen radical, particularly preferably a chlorine or bromine atom, to form a compound of the general formula IV, in which R, $R^3$ and $R^4$ are as defined hereinbefore and $R^3$ is not hydrogen, and said compound is optionally purified and/or isolated, and at least a compound of the general formula IV is reacted in a reaction medium in the presence of at least a base, preferably in the presence of at least a metal hydroxide, to form a compound of the general formula VI,

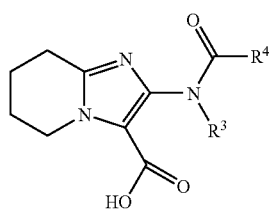

VI in which $R^3$ is as defined hereinbefore with the exception of the hydrogen radical and $R^4$ is as defined hereinbefore, and said compound is purified and/or isolated and at least a compound of the general formula VI is reacted in a reaction medium in the presence of at least a coupling reagent, optionally in the presence of at least a base with at least a compound of the general formula $HNR^1R^2$, in which $R^1$ is as defined hereinbefore and $R^2$ is hydrogen, to form a compound of the general formula I

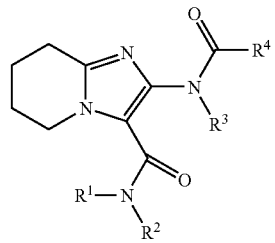

I in which $R^3$ is as defined hereinbefore with the exception of the hydrogen radical, $R^1$ and $R^4$ are as defined hereinbefore and $R^2$ represents hydrogen, and said compound is optionally purified and/or isolated and optionally at least a compound of the general formula I, in which $R^3$ is as defined hereinbefore with the exception of the hydrogen radical, $R^1$ and $R^4$ are as defined as hereinbefore and $R^2$ represents hydrogen, is reacted in a reaction medium in the presence of at least a base, preferably a metal hydride, with at least a compound of the general formula $R^2$—X, in which $R^2$ is as defined hereinbefore with the exception of the hydrogen radical and X represents a leaving group, preferably a halogen radical, particularly preferably a chlorine or bromine atom, to form a compound of the general formula I, in which $R^1$ and $R^4$ are as defined hereinbefore and $R^2$ and $R^3$ are as defined hereinbefore with the exception of the hydrogen radical, and said compound is purified and/or isolated or at least a compound of the general formula VI is reacted in a reaction medium in the presence of at least a coupling reagent, optionally in the presence of at least a base with at least a compound of the general formula $HNR^1R^2$, in which $R^1$ and $R^2$ are as defined hereinbefore with the exception of the hydrogen radical, to form a compound of the general formula I, in which $R^1$, $R^2$ and $R^3$ are as defined hereinbefore with the exception of the hydrogen radical and $R^4$ is as defined hereinbefore, and said compound is optionally purified and/or isolated.

The present invention further relates to a method for preparing compounds of the aforementioned general formula I according to the invention, according to which at least a compound of the general formula II,

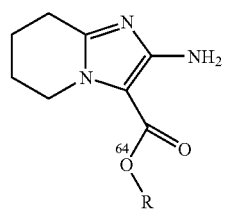 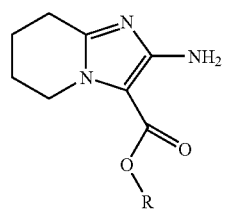

II in which R represents a linear or branched $C_{1-6}$ alkyl radical, preferably a methyl or ethyl radical, is reacted in a reaction medium, optionally in the presence of at least a base with at least a compound of the general formula $R^4$—C(=O)—X, in which $R^4$ is as defined hereinbefore and X represents a leaving group, preferably a halogen radical, particularly preferably a chlorine or bromine atom, or in a reaction medium in the presence of at least a coupling reagent, optionally in the presence of at least a base, with a compound of the general formula R⁴—C(=O)—OH, in which R⁴ is as defined hereinbefore, to form a compound of the general formula IV,

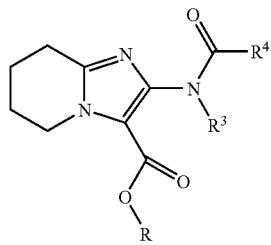

in which R and R⁴ are as defined hereinbefore and R³ is hydrogen, and said compound is optionally purified and/or isolated, and at least a compound of the general formula IV is reacted in a reaction medium in the presence of at least a base, preferably in the presence of at least a metal hydroxide, to form a compound of the general formula VI,

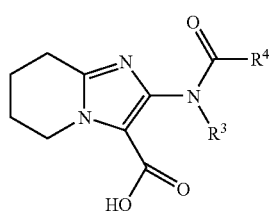

in which R⁴ is as defined hereinbefore and R³ is hydrogen, and said compound is optionally purified and/or isolated and at least a compound of the general formula VI is reacted in a reaction medium in the presence of at least a coupling reagent, optionally in the presence of at least a base, with at least a compound of the general formula HNR¹R², in which R¹ and R² are as defined hereinbefore, to form a compound of the general formula I,

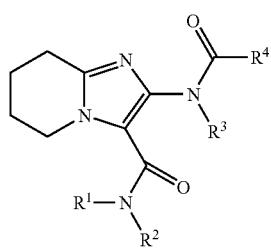

in which R¹, R² and R⁴ are as defined hereinbefore and R³ is hydrogen, and said compound is optionally purified and/or isolated.

The methods for preparing substituted 5,6,7,8-tetrahydro-imidazo[1,2-a]pyridin-2-ylamine compounds of the afore-mentioned formula I are also described in the following diagrams 1 to 3.

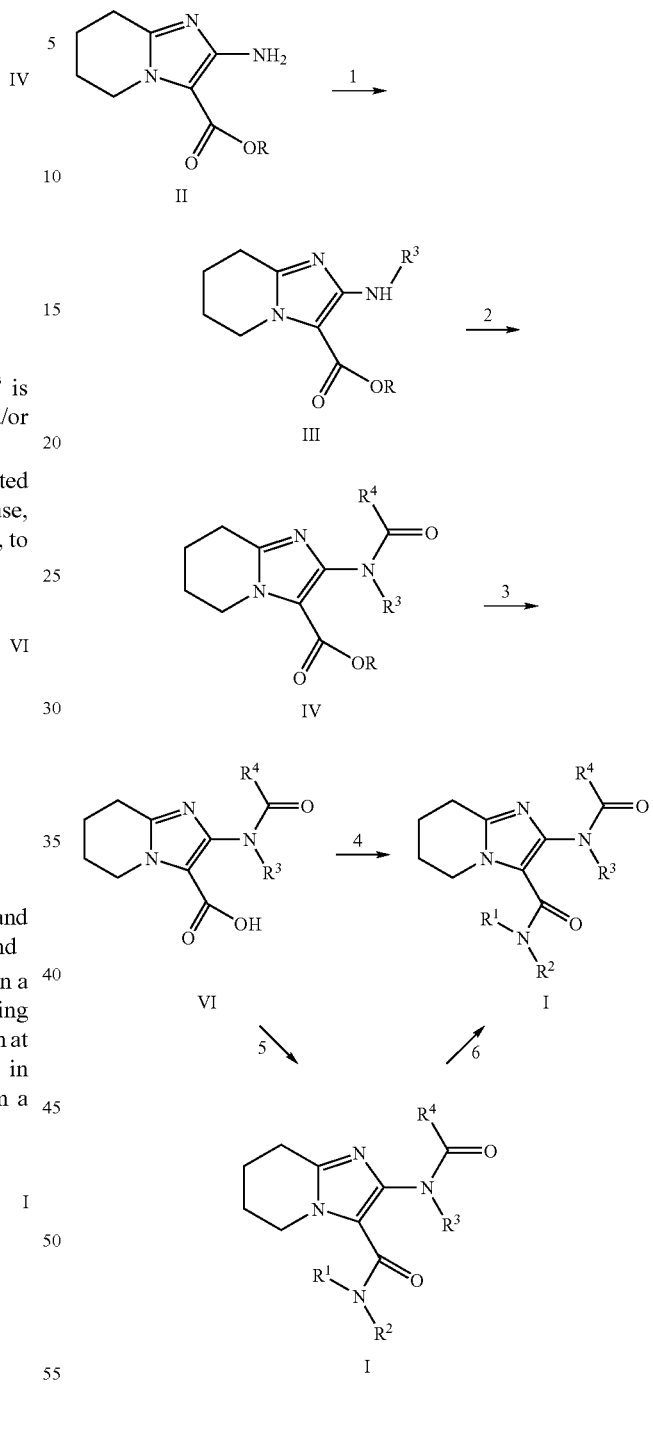

Pattern 1

In stage 1 compounds of the aforementioned general formula II are reacted with aldehydes of the general formula R³—C(=O)—H, in which R³ is as defined hereinbefore with the exception of the hydrogen radical, in a reaction medium, preferably selected from the group consisting of diethylether, tetrahydrofuran, methanol, ethanol, dichloromethane, dichlorethane, chloroform, toluene and corresponding mixtures, with the addition of a reducing agent, preferably selected from the group consisting of sodium borohydride, sodium acetoxyborohydride or sodium cyanoborohydride, optionally in the presence of at least an organic acid, preferably in the presence of acetic acid, at temperatures of preferably −70° C. to 100° C. to form compounds of the general formula III.

In Stage 2 compounds of the aforementioned general formula III are reacted with carboxylic acids of the general formula $R^4$—C(=O)—OH, in which $R^4$ is as defined hereinbefore, in a reaction medium preferably selected from the group consisting of diethylether, tetrahydrofuran, acetonitrile, methanol, ethanol, dimethylformamide, dichloromethane and corresponding compounds, optionally in the presence of at least a coupling reagent preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), N-[(dimethyamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluroniom hexafluorophosphate (HBTU) and 1-hydroxy-7-azabenzotriazole (HOAt), optionally in the presence of at least an inorganic base preferably selected from the group consisting of potassium carbonate and calcium carbonate, or at least an organic base preferably selected from the group consisting of triethylamine, pyridine, dimethylaminopyridine and diisopropylethylamine, preferably at temperatures of −70° C. to 100° C. to form compounds of the general formula IV.

Alternatively, compounds of the general formula III are reacted with carboxylic acid derivatives or carbon dioxide derivatives of the general formula $R^4$—C(=O)—X, in which $R^4$ is as defined hereinbefore and X represents a halogen radical, preferably chlorine or bromine, in a reaction medium preferably selected from the group consisting of diethylether, tetrahydrofuran, acetonitrile, methanol, ethanol, dimethylformamide, dichloromethane and corresponding mixtures, optionally in the presence of at least an organic base preferably selected from the group consisting of triethylamine, dimethylaminopyridine, pyridine and diisopropylamine, or at least an inorganic base at temperatures of preferably −70° C. to 100° C. to form compounds of the general formula IV.

Similarly, compounds of the general formula II may be reacted with carboxylic acids of the general formula $R^4$—C(=O)—OH or compounds of the general formula $R^4$—C(=O)—X as described hereinbefore in stage 2, to form compounds of the general formula IV, in which R and $R^4$ are as defined hereinbefore and $R^3$ is hydrogen.

In Stage 3, compounds of the general formula IV are reacted in a suitable reaction medium, preferably selected from the group consisting of dioxan, tetrahydrofuran, diethylether, methanol, ethanol, isopropanol, water and corresponding mixtures, with the addition of at least an inorganic base, preferably with the addition of at least a metal hydroxide, for example sodium hydroxide, potassium hydroxide or lithium hydroxide, at temperatures of preferably 0° C. to 30° C. to form compounds of the general formula VI. The reaction preferably takes place in a reaction medium consisting of methanol, dioxan and a 4 M sodium hydroxide solution in water with a ratio of 15:4:1 for the corresponding volumes.

In Stage 4 compounds of the aforementioned general formula VI are reacted with amines of the general formula $HNR^1R^2$, in which $R^1$ and $R^2$ are as defined hereinbefore, in a reaction medium preferably selected from the group consisting of diethylether, tetrahydrofuran, acetonitrile, methanol, ethanol, dimethylformamide, dichloromethane and corresponding compounds, optionally in the presence of at least a coupling reagent preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), N-[(dimethylamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluroniom hexafluorophosphate (HBTU) and 1-hydroxy-7-azabenzotriazole (HOAt), optionally in the presence of at least an inorganic base preferably selected from the group consisting of potassium carbonate and calcium carbonate, or an organic base preferably selected from the group consisting of triethylamine, pyridine, dimethylaminopyridine and diisopropylethylamine, preferably at temperatures of −70° C. to 100° C. to form compounds of the general formula I.

In stage 5, compounds of the general formula VI are reacted with amines of the general formula $HNR^1R^2$, in which $R^1$ is as defined hereinbefore and $R^2$ represents hydrogen, using the methods described hereinbefore in Pattern 1, Stage 4, to form compounds of the general formula I, in which $R^1$, $R^3$ and $R^4$ are as defined hereinbefore, $R^3$ is not hydrogen and $R^2$ is hydrogen.

In Stage 6 compounds of the general formula I, in which $R^1$, $R^3$ and $R^4$ are as defined hereinbefore, $R^3$ is not hydrogen and $R^2$ is hydrogen, are reacted with compounds of the general formula $R^2$—X, in which $R^2$ is as defined hereinbefore and is not hydrogen and X represents a halogen radical, preferably chlorine, in a reaction medium preferably selected from the group consisting of dimethylformamide, heptane, hexane, toluene, tetrahydrofuran, diethylether and corresponding mixtures, with the addition of at least a metal hydride, preferably with the addition of a metal hydride salt selected from the group consisting of sodium hydride, potassium hydride and lithium hydride, at temperatures of preferably 0° C. to 40° C. to form compounds of the general formula I, in which $R^1$, $R^2$, $R^3$ and $R^4$ are as defined hereinbefore and $R^2$ and $R^3$ are not hydrogen.

The compounds of the general formula IV are similarly obtained as shown in Pattern 2.

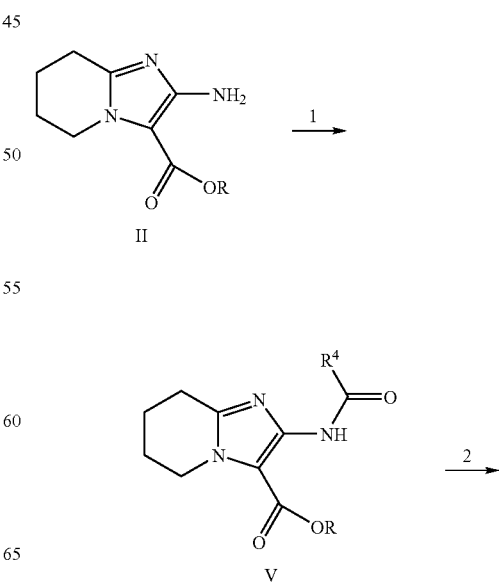

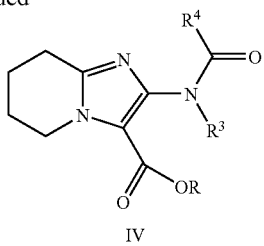

Pattern 2.

In Stage 1, compounds of the aforementioned general formula II are reacted with carboxylic acids of the general formula $R^4$—C(=O)—OH, in which $R^4$ is as defined hereinbefore, or with carboxylic acid derivatives or carbon dioxide derivatives of the general formula $R^4$—C(=O)—X, in which $R^4$ is as defined hereinbefore and X represents a halogen radical, preferably chlorine or bromine, using the same methods as described in Pattern 1, Stage 2 to form compounds of the general formula V.

In Stage 2, compounds of the general formula V are reacted with compounds of the general formula $R^3$—X, in which $R^3$ is as defined hereinbefore and is not hydrogen and X represents a halogen radical, preferably chlorine, using the same methods as described in Pattern 1, stage 6, to form compounds of the general formula IV.

Compounds of the general formula II are obtained as described in Pattern 3.

Pattern 3.

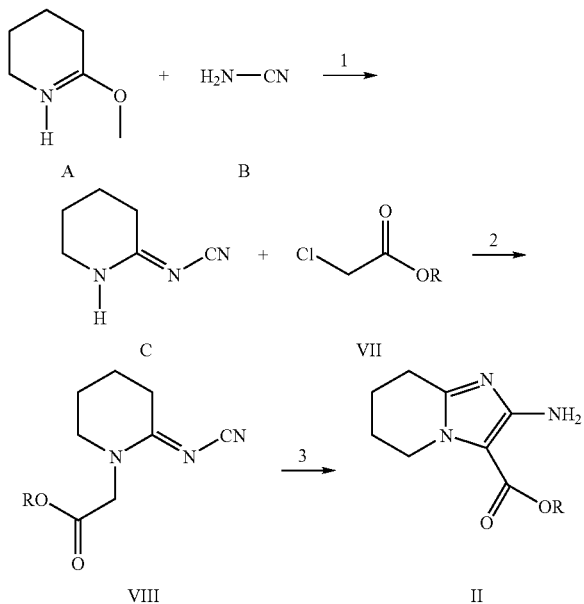

In Stage 1, 6-methoxy-2,3,4-5-tetrahydropyridine (A) is reacted in a reaction medium preferably selected from the group consisting of methanol, ethanol and isopropanol, with cyanamide B preferably at a temperature of from 0° C. to 30° C. to form the desired compound piperidin-2-ylidene-cyanamide (C). 6-methoxy-2,3,4-5-tetrahydropyridine (A) was obtained according to the reference documents "Product class 18: pyridopyridazines"; Sako, M.; Science of Synthesis 2004, 1109-1153; "Synthesis of pyrido[4,3-d]pyrimidin-5(6H)-ones via anionic cycloaddition of methyl-2,4-dimethoxy-6-methyl-5-pyrimidinecarboxylate with imines"; Wada, A. et al.; Chemical and Pharmaceutical Bulletin 1991, 1189-1192, and "Reaction of lactim ethers with 2-(carbethoxymethyl)-piperidines"; Takahata, H. et al. Fukusokan Kagaku Toronkai Koen Yoshishu, 12th (1979), 296-300. The corresponding sections of the reference documents hereby form part of the disclosure.

In Stage 2, the compound C from Stage 1 is reacted, without further purification, with a compound of the general formula VII, in which R represents a linear or branched $C_{1-6}$ alkyl radical, preferably a methyl or ethyl radical, in a reaction medium preferably selected from the group consisting of acetonitrile, dichloromethane, chloroform, dimethylformamide, dimethylacetamide and dimethyl sulphoxide, with the addition of an inorganic base, preferably selected from the group consisting of potassium carbonate, sodium carbonate, lithium carbonate and magnesium carbonate, preferably at a temperature of 50° C. to 150° C. to form a compound of the general formula VIII, in which R is as defined hereinbefore.

In Stage 3 a compound of the general formula VIII is reacted in a reaction medium preferably selected from the group consisting of methanol, ethanol, isopropanol, with the addition of an alkali metal alkoxide salt, preferably selected from the group consisting of sodium methanolate, sodium ethanolate, potassium methanolate and potassium ethanolate, preferably at a temperature of 50° C. to 120° C. to form a compound of the general formula II.

Each of the compounds of the aforementioned formulae $R^3$—C(=O)—H, $R^4$—C(=O)—OH, $R^4$—C(=O)—X, $HNR^1R^2$, $R^2$—X, $R^3$—X, B and VII is commercially available and can also be prepared by conventional methods known to a person skilled in the art.

Each of the reactions described above may be carried out under conventional conditions familiar to a person skilled in the art, for example with regard to pressure or the order of adding components. A person skilled in the art may optionally determine an optimal method by carrying out simple preliminary tests. If desired and/or necessary, the intermediate and end products obtained through the aforementioned reactions may each be purified and/or isolated using conventional methods known to a person skilled in the art. Suitable purification methods include, for example, extraction and chromatography processes such as column chromatography or preparative chromatography. All of the aforementioned steps, and also the purification and/or isolation of intermediate or end products may be carried out, in part or entirely, under an inert gas atmosphere, preferably under a nitrogen atmosphere.

The substituted 5,6,7,8-tetrahydro-imidazo[1,2-a]pyridin-2-ylamine compounds of the aforementioned general formula I, and also the corresponding stereoisomers may be isolated in the form of the free bases thereof, the free acids thereof and also in the form of corresponding salts, in particular physiologically acceptable salts. The free bases of each substituted 5,6,7,8-tetrahydro-imidazo[1,2-a]pyridin-2-ylamine compound of the aforementioned general formula I and the corresponding stereoisomers may be converted into the corresponding salts, preferably physiologically acceptable salts by reaction with an inorganic or organic acid, preferably hydrochloric acid, hydrobromic acid, sulphuric acid, phosphoric acid, methanesulphonic acid, p-toluenesulphonic acid, carbon dioxide, formic acid, acetic acid, oxalic acid, succinic acid, tartaric acid, mandelic acid, fumaric acid, lactic acid, citric acid, glutamic acid or aspartic acid. The free bases of each substituted 5,6,7,8-tetrahydro-imidazo[1,2-a]pyridin-2- ylamine compound of the aforementioned general formula I and the corresponding stereoisomers may also be reacted with the free acid or a salt of a sweetener such as saccharine, cyclamate or acesulfame to form the corresponding physiologically acceptable salts by reaction with the free salts.

Correspondingly, the free acids of the substituted 5,6,7,8-tetrahydro-imidazo[1,2-a]pyridin-2-ylamine compounds of the aforementioned general formula I and the corresponding stereoisomers may be converted into the corresponding physiologically acceptable salts by reaction with a suitable base. Examples include the alkali metal salts, alkaline earth metal salts or ammonium salts $[NH_xR_{4-x}]^+$, in which x=0, 1, 2, 3 or 4 and R represents a linear or branched $C_{1-4}$ alkyl radical.

The 5,6,7,8-tetrahydro-imidazo[1,2-a]pyridin-2-ylamine compounds of the aforementioned general formula I according to the invention and the corresponding stereoisomers may optionally be obtained, like the corresponding acids, the corresponding bases or salts of said compounds, in the form of the solvates thereof, preferably in the form of the hydrates thereof, using conventional methods known to a person skilled in the art.

If, after preparation, the 5,6,7,8-tetrahydro-imidazo[1,2-a]pyridin-2-ylamine compounds of the aforementioned general formula I according to the invention are obtained in the form of a mixture of the stereoisomers thereof, preferably in the form of the racemates thereof or other mixtures of the various enantiomers and/or diastereomers thereof, said compounds may be separated and optionally isolated using conventional methods known to a person skilled in the art. Examples of such methods include chromatographic separation methods, in particular liquid chromatography under normal pressure or elevated pressure, preferably MPLC and HPLC, and also fractional crystallisation. In this way in particular individual enantiomers AND/OR diasteromer salts formed may be separated from one another, for example, by means of HPLC in the chiral stationary phase or by means of crystallisation with chiral acids such as (+)-tartaric acid, (−)-tartaric acid or (+)-10-camphorsulphonic acid.

The substituted 5,6,7,8-tetrahydro-imidazo[1,2-a]pyridin-2-ylamine compounds of the aforementioned general formula I according to the invention and the corresponding stereoisomers, and also the respective acids, bases, salts and solvates are toxicologically acceptable and are therefore suitable as pharmaceutical active ingredients in pharmaceutical compositions.

The present invention accordingly further relates to a pharmaceutical composition comprising at least a 5,6,7,8-tetrahydro-imidazo[1,2-a]pyridin-2-ylamine compound of the aforementioned general formula I according to the invention, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of a corresponding salt or each in the form of a corresponding solvate, and optionally also one or more pharmaceutically acceptable auxiliaries.

Said pharmaceutical compositions according to the invention are particularly suitable for regulating vanilliod receptor 1 (VR1/TRPV1), preferably for inhibiting vanilliod receptor 1 (VR1/TRPV1) and/or regulating batrachotoxin (BTX) receptors, preferably for inhibiting the batrachotoxin (BTX) receptors and/or for regulating opioid receptors, preferably for regulating μ-opioid receptors.

In a similarly preferred manner, the pharmaceutical compositions according to the invention are also suitable for the prophylaxis and/or treatment of disorders or diseases mediated at least in part by vanilloid receptors 1 and/or by batrachotoxin receptors and/or by opioid receptors, in particular by μ-opioid receptors.

Preferably, the pharmaceutical composition according to the invention is thus suitable for the treatment and/or prophylaxis of pain, preferably of pain selected from the group consisting of acute pain, chronic pain and neuropathic pain; for the prophylaxis and/or treatment of one or more diseases selected from the group consisting of migraine; depression; urinary incontinence; coughs; neurodegenerative diseases, preferably selected from the group consisting of Parkinson's disease, Huntington's disease, Alzheimer's disease and multiple sclerosis; eating disorders, preferably selected from the group consisting of bulimia, anorexia, obesity and cachexia; states of anxiety; cognitive dysfunction, preferably memory impairment; cognitive deficiencies (attention deficit syndrome, ADS); epilepsy; diarrhoea and pruritis;

for the prophylaxis and/or treatment of alcohol and/or drug and/or medicine abuse and/or addiction to alcohol and/or drugs and/or medicines, preferably for the prophylaxis and/or reduction of withdrawal symptoms for those with addictions to alcohol and/or drugs and/or medicines; for the prophylaxis and/or reduction of the development of tolerance in relation to medicines, in particular opioid-based medicines; for regulation of food intake; for modulation of movement; for regulation of the cardiovascular system; as a local anaesthetic; for increasing vigilance; for increasing libido; for diuresis and/or antinatriuresis.

In a particularly preferred manner, the pharmaceutical composition according to the invention is thus suitable for the treatment and/or prophylaxis of pain, preferably of pain selected from the group consisting of acute pain, chronic pain and neuropathic pain; for the prophylaxis and/or treatment of one or more diseases selected from the group consisting of migraine; depression; neurodegenerative diseases, preferably selected from the group consisting of Parkinson's disease, Huntington's disease, Alzheimer's disease and multiple sclerosis; states of anxiety; cognitive dysfunction, preferably memory impairment; cognitive deficiencies (attention deficit syndrome, ADS); epilepsy; for the prophylaxis and/or treatment of alcohol and/or drug and/or medicine abuse and/or addiction to alcohol and/or drugs and/or medicines, preferably for the prophylaxis and/or reduction of withdrawal symptoms for those with addictions to alcohol and/or drugs and/or medicines; for the prophylaxis and/or reduction in the development of tolerance in relation to medicines, in particular opioid-based medicines.

In a very particularly preferred manner, the pharmaceutical composition according to the invention is suitable for the treatment and/or prophylaxis of pain, preferably of pain selected from the group consisting of acute pain, chronic pain and neuropathic pain.

The present invention further relates to the use of at least a 5,6,7,8-tetrahydro-imidazo[1,2-a]pyridin-2-ylamine compound of the aforementioned general formula I, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of a corresponding salt or each in the form of a corresponding solvate, and optionally also one or more pharmaceutically acceptable auxiliaries for the preparation of a pharmaceutical composition for regulating vanilliod receptor 1 (VR1/TRPV1), preferably for inhibiting vanilliod receptor 1 (VR1/TRPV1) and/or regulating batrachotoxin (BTX) receptors, preferably for inhibiting the batrachotoxin (BTX) receptors and/or for regulating opioid receptors, preferably for regulating μ-opioid receptors.

The use of at least a substituted 5,6,7,8-tetrahydro-imidazo [1,2-a]pyridin-2-ylamine compound of the aforementioned general formula I, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of a corresponding salt or each in the form of a corresponding solvate, and optionally also one or more pharmaceutically acceptable auxiliaries for the preparation of a pharmaceutical composition for the prophylaxis and/or treatment of disorders or diseases mediated at least in part by vanilloid receptors 1 and/or by batrachotoxin receptors and/or by opioid receptors, is preferred.

The use of at least a substituted 5,6,7,8-tetrahydro-imidazo [1,2-a]pyridin-2-ylamine compound of the aforementioned general formula I, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of a corresponding salt or each in the form of a corresponding solvate, and optionally also one or more pharmaceutically acceptable auxiliaries for the preparation of a pharmaceutical composition for the treatment and/or prophylaxis of pain, preferably of pain selected from the group consisting of acute pain, chronic pain and neuropathic pain; for the prophylaxis and/or treatment of one or more diseases selected from the group consisting of migraine; depression; urinary incontinence; coughs; neurodegenerative diseases, preferably selected from the group consisting of Parkinson's disease, Huntington's disease, Alzheimer's disease and multiple sclerosis; eating disorders, preferably selected from the group consisting of bulimia, anorexia, obesity and cachexia; states of anxiety; cognitive dysfunction, preferably memory impairment; cognitive deficiencies (attention deficit syndrome, ADS); epilepsy; diarrhoea and pruritis; for the prophylaxis and/or treatment of alcohol and/or drug and/or medicine abuse and/or addiction to alcohol and/or drugs and/or medicines, preferably for the prophylaxis and/or reduction of withdrawal symptoms for those with addictions to alcohol and/or drugs and/or medicines; for the prophylaxis and/or reduction in the development of tolerance in relation to medicines, in particular opioid-based medicines; for regulation of food intake; for modulation of movement; for regulation of the cardiovascular system; as a local anaesthetic; for increasing vigilance; for increasing libido; for diuresis and/or antinatriuresis is particularly preferred.

The use of at least a substituted 5,6,7,8-tetrahydro-imidazo [1,2-a]pyridin-2-ylamine compound of the aforementioned general formula I, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of a corresponding salt or each in the form of a corresponding solvate, and optionally also one or more pharmaceutically acceptable auxiliaries for the preparation of a pharmaceutical composition for the treatment and/or prophylaxis of pain, preferably of pain selected from the group consisting of acute pain, chronic pain and neuropathic pain; for the prophylaxis and/or treatment of one or more diseases selected from the group consisting of migraine; depression; neurodegenerative diseases, preferably selected from the group consisting of Parkinson's disease, Huntington's disease, Alzheimer's disease and multiple sclerosis; states of anxiety; cognitive dysfunction, preferably memory impairment; cognitive deficiencies (attention deficit syndrome, ADS); epilepsy; for the prophylaxis and/or treatment of alcohol and/or drug and/or medicine abuse and/or addiction to alcohol and/or drugs and/or medicines, preferably for the prophylaxis and/or reduction of withdrawal symptoms for those with addictions to alcohol and/or drugs and/or medicines; for the prophylaxis and/or reduction in the development of tolerance in relation to medicines, in particular opioid-based medicines, is very particularly preferred.

The use of at least a substituted 5,6,7,8-tetrahydro-imidazo [1,2-a]pyridin-2-ylamine compound of the aforementioned general formula I, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of a corresponding salt or each in the form of a corresponding solvate, and optionally also one or more pharmaceutically acceptable auxiliaries for the preparation of a pharmaceutical composition for the treatment and/or prophylaxis of pain, preferably of pain selected from the group consisting of acute pain, chronic pain and neuropathic pain is more particularly preferred.

The pharmaceutical composition according to the invention is suitable for administration to adults and children, including infants and babies. The pharmaceutical composition according to the invention as a liquid, semisolid or solid dosage form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules may optionally be compressed to form tablets, poured into capsules or suspended in a liquid and may also be administered as such.

In addition to a substituted 5,6,7,8-tetrahydro-imidazo[1,2-a]pyridin-2-ylamine compound of the aforementioned general formula I, each optionally in the form of one of the pure stereoisomers thereof, in particular enantiomers or diastereomers, the racemates thereof or in the form of a mixture of stereoisomers, in particular of enantiomers and/or diastereomers, in any desired mixing ratio, or each in the form of a corresponding salt or each in the form of a corresponding solvate, the pharmaceutical composition according to the invention also comprises, in a conventional manner, further physiologically acceptable pharmaceutically auxiliaries which may be selected, for example, from the group consisting of carrier materials, fillers, solvents, dilutents, surface-active agents, dyes, preservatives, blasting agents, lubricants, flavourings and binders.

The choice of physiologically acceptable auxiliares and the amounts thereof to be used depends on whether the pharmaceutical composition is to be administered orally, subcutaneously, parenterally, intravenously, intraperitoneally, intradermally, intramuscularly, intranasally, buccally, rectally or topically, for example to infections of the skin, the mucous membranes or the eyes. Preparations in the form of tablets, dragées, capsules, granules, pellets, drops, juices and syrups are suitable for oral administration; solutions, suspensions, easily reconstitutable dry preparations and sprays are suitable for parenteral, topical and inhalative administration. The substituted 5,6,7,8-tetrahydro-imidazo[1,2-a]pyridin-2-ylamine compounds according to the invention used in the pharmaceutical compositions according to the invention are suitable percutaneous application preparations when in a controlled release form in a dissolved form or in a plaster, optionally with the addition of agents to promote skin penetration. Forms of preparation which can be administered orally or percutaneously may also release the respective substituted 5,6,7,8-tetrahydro-imidazo[1,2-a]pyridin-2-ylamine compounds according to the invention in a delayed manner.

The pharmaceutical compositions according to the invention are prepared using conventional resources, devices, methods and processes known from the prior art, such as those described in "Remington's Pharmaceutical Sciences", edited by A. R. Gennaro, 17th edition, Mack Publishing Company, Easton, Pa., 1985, in particular in section 8, chapters 76 to 93. The corresponding description is hereby introduced as a reference and is deemed to be part of the disclosure. The amount of the respective substituted 5,6,7,8-tetrahydro-imidazo[1,2-a]pyridin-2-ylamine compounds of the general formula I according to the invention to be administered to the patient may vary and is dependent, for example, on the weight or age of the patient and on the method of administration, the indication and the severity of the disease. Conventionally, 0.001 to 100 mg/kg, preferably 0.05 to 75 mg/kg, particularly preferably 0.05 to 50 mg/kg of the body weight of the patient of at least one such compound according to the invention are applied.

Pharmacological Methods:

I. Functional Analysis on the Vanilloid Receptor 1 (VR1/TRPV1 Receptor)

The agonistic or antagonistic effect of the substances to be tested on the vanilloid receptor 1 (VR1/TRPV1) of rats may be determined using the following assay. In this assay, the $Ca^{2+}$ influx through the receptor channel is quantified by using a $Ca^{2+}$-sensitive dye (Fluo-4, Molecular Probes Europe BV, Leiden, The Netherlands) in the fluorescent imaging plate reader (FLIPR, Molecular Devices, Sunnyvale, USA).

Method:
Complete medium: 50 mL HAMS F12 nutrient mixture (Gibco Invitrogen GmbH, Karlsruhe, Germany) with
10% by volume of FCS (foetal calf serum, Gibco Invitrogen GmbH, Karlsruhe, Germany, heat-activated);
2 mM L-glutamine (Sigma, Munich, Germany);
1% by weight of AA solution (antibiotic-antimycotic solution, PAA, Pasching, Austria)
and 25 ng/ml of NGF medium (2.5 S Gibco Invitrogen GmbH, Karlsruhe, Germany)
cell culture plate: poly-D-lysine-coated, 96-well black plates with a clear base (BD Biosciences, Heidelberg, Germany) are additionally coated with laminin (Gibco Invitrogen GmbH, Karlsruhe, Germany), the laminin being diluted with PBS (Ca/Mg-free PBS, Gibco Invitrogen, GmbH, Karlsruhe, Germany) to a concentration of 100 µg/mL. Aliquots with a laminin concentration of 100 µg/mL are extracted and stored at −20° C. The aliquots are thinned with PBS in a ratio of 1:10 to 10 µg/mL laminin and 50 µL of the solution respectively were transferred to a recess in the cell culture plate using a pipette. The cell culture plates are incubated for at least two hours at 37° C., the remaining solution is suction-filtered and the recesses are each washed twice with PBS. The coated cell culture plates are stored with the supernatant PBS, which is only removed immediately before adding the cells.

Preparation of the Cells:

The spinal column is removed from decapitated rats and placed immediately in a cold, i.e. in an ice bath, HBSS buffer (Hank's buffered saline solution, Gibco Invitrogen GmbH, Karlsruhe, Germany) mixed with 1% by volume (volume percent) of an AA solution (antibiotic-antimycotic solution, PAA, Pasching, Austria). The spinal column is longitudinally transected and removed, with fasciae, from the spinal canal. The dorsal root ganglia (DRGs) are subsequently removed and again stored in a cold HBSS buffer mixed with 1% by volume of an AA solution. The DRGs, from which any remaining blood or spinal nerves have been completely removed, are transferred into 500 µL of cold type II collagenase (PAA, Pasching, Austria) and incubated at 37° C. for 35 minutes. After adding 2.5% by volume of trypsin (PAA, Pasching, Austria), it is incubated for a further 10 minutes at 37° C. After incubation is complete, the enzyme solution is carefully removed using a pipette and the remaining DRGs are mixed with 500 µL of the complete medium.

The DRGs are each suspended a number of times, drawn by means of a syringe through cannulae No. 1, No. 12 and No. 16 and transferred into 50 mL Falcon tubes, which are made up to 15 ml with complete medium. The contents of each Falcon tube are each filtered through a 70 µm Falcon filter element and centrifuged for 10 minutes at 1200 rpm and at room temperature. The resulting pellets are each added to 250 µL of complete medium and the cell count is determined.

The number of cells in the suspension is adjusted to $3 \times 10^5$ per mL and each 150 µL of said suspension is added to a recess in the cell culture plate coated as described hereinbefore. The plates are left in the incubator for two to three days at 37° C., at 5% by volume of $CO_2$ and at 95% atmospheric moisture.

The cells are then loaded with 2 µM Fluo-4 and 0.01% by volume of Pluronic F127 (Molecular Probes Europe BV, Leiden, The Netherlands) in HBSS Buffer (Hank's buffered saline solution, Gibco Invitrogen GmbH, Karlsruhe, Germany) for 30 minutes at 37° C., washed with HBSS buffer three times and, after further incubation for 15 minutes at room temperature, are used for $Ca^{2+}$ measurement in the FLIPR assay. In this test, the fluorescence caused by $Ca^{2+}$ is measured before and after the addition of substances ($\lambda ex=488$ nm, $\lambda em=540$ nm). It is quantified by measuring the highest fluorescence intensity (FC, fluorescence counts) over time.

FLIPR Assay:

The FLIPR protocol consists of adding two substances. The compounds to be tested (10 µM) are initially added by pipette to the cells and the $Ca^{2+}$ influx is compared to the control (capsaicin 10 µM). This provides the measurement in % of activation with regard to the $Ca^{2+}$ signal after the addition of 10 µM Capsaicin (CP). After 5 minutes' incubation, 100 nM of capsaicin is applied and the $Ca^{2+}$ influx is also measured.

Desensitising agonists and antagonists lead to a suppression of the $Ca^{2+}$ influx. The % of inhibition is calculated in comparison to the maximum possible inhibition with 10 µM capsaicin.

Three measurements (n=3) are carried out and repeated in at least three independent experiments (N=4).

II. Method for Determining the Affinity to the Batrachotoxin (BTX) Binding Site of the Sodium Channel:

The binding site 2 of the sodium channel is what is known as the batrachotoxin (BTX) binding site. [$^3$H]-batrachotoxinin A20 α-benzoate (10 nM in the batch) was used as the ligand. The ion channel particles (synaptosomes) are enriched from the rats' cerebral cortex, as described in the paper by Gray and Whittaker, 1962, J. Anat. 76, 79-88. The corresponding description is hereby introduced as a reference and is deemed to be part of the present disclosure. The radioactivity measured in the presence of veratridin ($3 \times 10^{-4}$ M in the batch) is defined as the non-specific bond.

The assay was conducted under conditions corresponding to those described in the paper by Pauwels, Leysen and Laduron, Eur. J. Pharmacol. 124, 291-298. The corresponding description is hereby introduced as a reference and is deemed to be part of the present disclosure.

In a departure from said specifications, the total batch is reduced to 250 µl so that the assay can be conducted on 96 well microtitre plates. The incubation time in said microtitre plates is 2 hours at room temperature (approximately 20-25° C.).

The following characteristics were determined for the $K_D$ value of the binding site.

$K_D$: 24.63±1.56 nM.

III. Method for Determining the Affinity to the Human µ-Opioid Receptor

The receptor affinity to the human µ-opioid receptor is determined in a homogeneous batch in microtitre plates. In this case, dilution series of the respective substituted 5,6,7,8-tetrahydro-imidazo[1,2-a]pyridin-2-ylamine compound of the general formula I to be tested are incubated with a receptor membrane preparation (15-40 µg of protein per 250 µl of the incubation batch) of CHO-K1 cells which express the human µ-opioid receptor (µ-opiate receptor) (RB-HOM receptor membrane preparation from NEN, Zaventem, Belgium) in the presence of 1 nmol/l of the radioactive ligands [$^3$H]-naloxone (NET719, NEN, Zaventem, Belgium) and also 1 mg of WGA SPA beads (wheat germ agglutinin SPA beads from Amersham Pharmacia, Freiburg, Germany) in a total volume of 250 µl at room temperature for 90 minutes. 50 mmol/l tris-HCl are used as an incubation buffer with 0.05% by weight of sodium azide and 0.06% by weight of bovine serum albumin. 25 µmol/l naloxone are also added to determine the non-specific bond. At the end of the 90 minute incubation period, the microtitre plates are centrifuged off for 20 minutes at 1000 g and the radioactivity is measured with a β-counter (Microbeta-Trilux, PerkinElmer Wallac, Freiburg, Germany. The percentage of displacement of the radioactive ligand from its bond to the human µ-opiate receptor at a concentration of 1 µmol/l of the compound to be tested is determined and indicated as a % inhibition of the specific bond.

The invention is explained below with reference to Examples. These explanations are given merely by way of example and do not restrict the general concept of the invention.

EXAMPLES

The yields of the compounds produced are not optimised. All temperatures are uncorrected.

ABBREVIATIONS aq. aqueous
eq. equivalent amount of substance
BOP 1-benzotriazolyloxy-tris-(dimethylamino)-phosphonium hexafluorophosphate
DCC dicyclohexylcarbodiimide
DCE dichloroethane
DCM dichloromethane
DIPEA disopropylethylamine
DMF dimethylformamide
EDCI N'-(3-dimethylaminopropyl)-N-ethylcarbodiimide
EtOAc ethylacetate
sat. saturated
HATU N-[(dimethyamino)-1H-1,2,3-triazolo[4,5-b]pyridino-1-ylmethylene]-N-methylmethanaminium hexafluorophosphate N-oxide
HBTU O-(benzotriazol-1-yl)-N,N,N',N'-tetramethyluronium hexafluorophosphate
HOAt 1-hydroxy-7-azabenzotriazole
HPTLC high performance thin layer chromatography
MeOH methanol
NMR nuclear resonance spectroscopy
RT room temperature The chemicals and solvents used were acquired commercially from conventional suppliers (Acros, Avocado, Aldrich, Bachem, Fluka, Lancaster, Maybridge, Merck, Sigma, TCI etc.) or synthesised using methods known to a person skilled in the art.

Silica gel 60 (0.040-0.063 mm) from E. Merck, Darmstadt was used as the stationary phase for column chromatography.

Thin-layer chromatography was performed with pre-coated silica gel 60 F 254 HPTLC plates from E. Merck, Darmstadt.

The mixing ratios of solvents, mobile solvents or for chromatographic analyses are always given in the form volume:volume.

Analysis was carried out using mass spectroscopy and NMR.

General Instructions for the Preparation of Exemplary Substituted 5,6,7,8-tetrahydro-imidazo[1,2-a]pyridin-2-ylamine Compounds

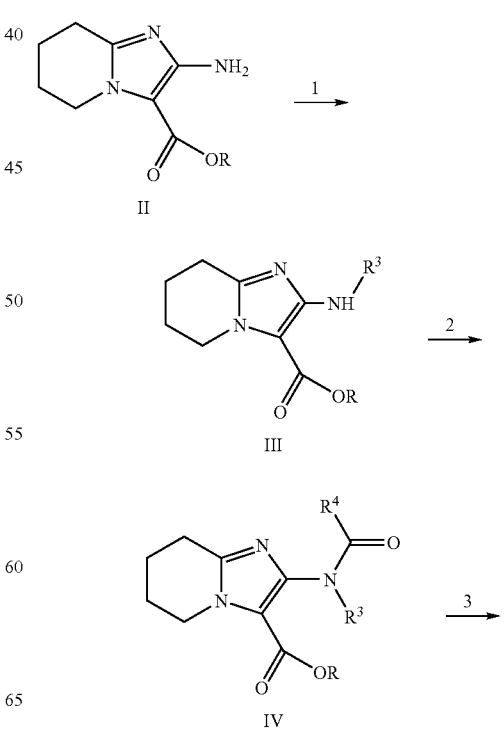

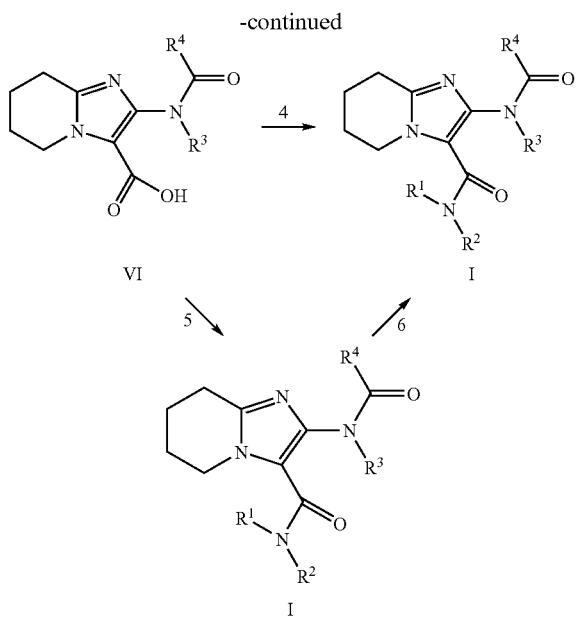

General Synthesis Pattern 1:

In Stage 1, compounds of the general formula II were reacted with aldehydes of the general formula $R^3$—C(=O)—H in organic solvents or solvent mixtures of, for example, diethylether, tetrahydrofuran, methanol, ethanol, dichloromethane, dichlorethane, chloroform and toluene, with the addition of a reducing agent, for example with the addition of sodium borohydride, sodium acetoxy borohydride or sodium cyanoborohydride, optionally with the addition of an organic acid, preferably with the addition of acetic acid, at temperatures of from −70° C. to 100° C. to form compounds of the general formula III.

In stage 2, compounds of the general formula III were reacted with carboxylic acids of the general formula $R^4$—C(=O)—OH in organic solvents or solvent mixtures of, for example, diethylether, tetrahydrofuran, acetonitrile, methanol, ethanol, dimethylformamide and dichloromethane, optionally with the addition of a coupling reagent, for example BOP, DCC, EDCI, HATU, HBTU or HOAt, optionally with the addition of at least an inorganic base, preferably with the addition of potassium carbonate or calcium carbonate, or an organic base, preferably with the addition of triethylamine, pyridine, dimethylaminopyridine or diisopropylethylamine, at temperatures of −70° C. to 100° C. to form compounds of the general formula IV.

Alternatively, compounds of the general formula III were reacted with carboxylic acid derivatives or carbonic acid derivatives of the general formula $R^4$—C(=O)—X, in which X represents a halogen radical, in organic solvents or solvent mixtures of, for example, diethylether, tetrahydrofuran, acetonitrile, methanol, ethanol, dimethylformamide and dichloromethane, with or without the addition of an organic base, for example with the addition of triethylamine, dimethylaminopyridine, pyridine or diisopropylamine at temperatures of from −70° C. to 100° C. to form compounds of the general formula IV.

In Stage 3, compounds of the general formula IV were reacted in organic solvents or solvent mixtures of, for example, dioxane, tetrahydrofuran, diethylether, methanol, ethanol, isopropanol and water, with the addition of an inorganic base, for example with the addition of sodium hydroxide, potassium hydroxide or lithium oxide, at temperatures of from 0° C. to 30° C. to form compounds of the general formula VI. The reaction preferably took place in a solvent mixture consisting of methanol, dioxane and a 4 M sodium hydroxide solution in water with a ratio of the corresponding volumes of 15:4:1 ("Tesser's base").

In stage 4, compounds of the general formula I were reacted with amines of the general formula $HNR^1R^2$ in organic solvents or solvent mixtures of, for example, diethylether, tetrahydrofuran, acetonitrile, methanol, ethanol, dimethylformamide and dichloromethane, optionally with the addition of at least a coupling reagent, for example with the addition of BOP, DCC, EDCI, HATU, HBTU or HOAt, optionally with the addition of at least an inorganic base, preferably with the addition of potassium carbonate or calcium carbonate, or an organic base, preferably with the addition of triethylamine, pyridine, dimethylaminopyridine or diisopropylethylamine, at temperatures of from −70° C. to 100° C. to form compounds of the general formula I.

In stage 5, compounds of the general formula VI cited hereinbefore were reacted with amines of the general formula $HNR^1R^2$, in which $R^2$ represents hydrogen, to compounds of the general formula I using methods as described in General Synthesis Pattern 1, Stage 4.

In Stage 6, compounds of the general formula Ia were reacted with compounds of the general formula $R^2$—X, in which X represents a halogen radical, in organic solvents or solvent mixtures, for example of dimethylformamide, heptane, hexane, toluene, tetrahydrofuran and diethylether, with the addition of a metal hydride salt, for example with the addition of sodium hydride, potassium hydride or lithium hydride, at temperatures of from 0° C. to 40° C. to form compounds of the general formula I.

General Synthesis Pattern 2:

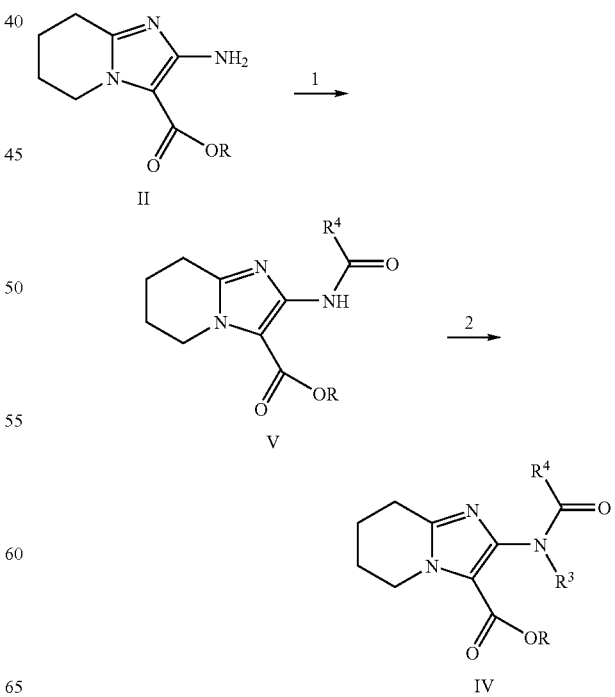

The compounds of general formula II are reacted using the same methods described in General Synthesis Pattern 1, Stage 2, to form compounds of the general formula V.

The compounds of general formula V are reacted using the same methods described in General Synthesis Pattern 1, Stage 6, to form compounds of the general formula IV.

General Synthesis Pattern 3:

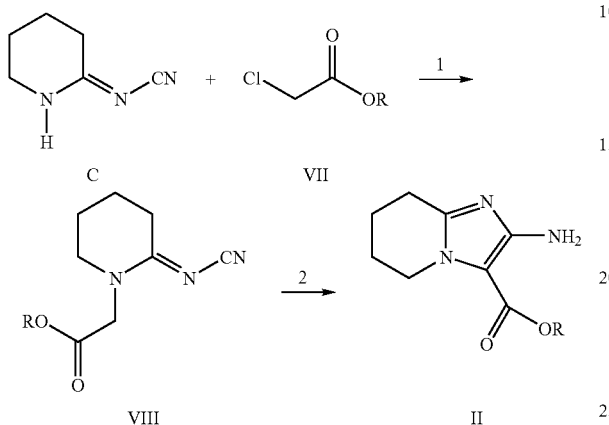

In Stage 1, piperidin-2-ylidene-cyanamide (C) was reacted with a compound of the general formula VII, in which R represents a linear or branched $C_{1-6}$ alkyl radical, in an organic solvents or solvent mixtures, for example of acetonitrile, dichloromethane, chloroform, dimethylformamide, dimethylacetamide and dimethylsulphoxide, with the addition of an inorganic base, for example with the addition of potassium carbonate, sodium carbonate, lithium carbonate or magnesium carbonate, at a temperature of from 50° C. to 150° C. to form a compound of the general formula VIII.

In Stage 2, a compound of the general formula VIII was reacted in organic solvents or solvent mixtures, preferably of methanol, ethanol and isopropanol, with the addition of an alkali metal alcoholate salt of, for example, sodium methanolate, sodium ethanolate, potassium methanolate and potassium ethanolate, at a temperature of from 50° C. to 120° C., to form a compound of the general formula II.

In the following, the instructions described above for the preparation of substituted 5,6,7,8-tetrahydro-imidazo[1,2-a]pyridin-2-ylamine compounds will be explained in more detail with reference to example compounds:

a) Synthesis of piperidin-2-ylidene-cyanamide

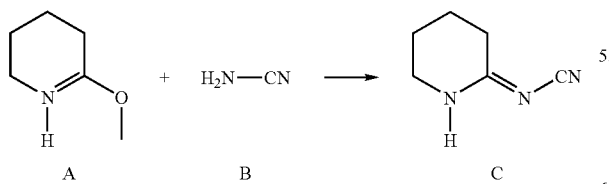

6-methoxy-2,3,4-5-tetrahydropyridine (A) (9.01 g, 79.6 mmol) was dissolved in a solution of MeOH (90 mL) and cyanamide (B) (3.35 g, 79.6 mmol, 1 eq.) was then slowly added thereto. After 5 minutes a white precipitate was observed. The resulting suspension was stirred for a further 72 hours at room temperature and the solvent was removed under vacuum. Piperidin-2-yliden-cyanamide (C) was obtained in the form of white powder, which was then directly used in a further reaction.

b) Synthesis of (2-cyanoimino-piperidin-1-yl)-acetic acid ethyl ester

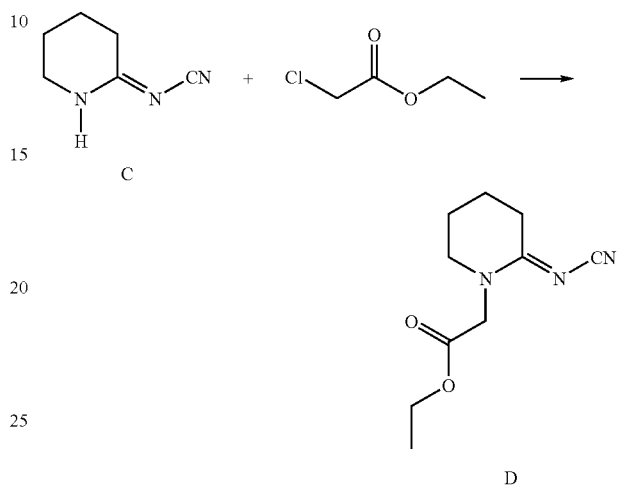

Piperidin-2-ylidene-cyanamide (C) (9.67 g, 78.5 mmol) was dissolved in acetonitrile (150 mL) under a low heat. Potassium carbonate (13.0 g, 94.2 mmol, 1.2 eq.) and Ethyl chloroacetate (11.7 mL, 109.9 mmol, 1.4 eq.) were then added thereto and the resulting suspension was heated for 16 hours at 85° C. A further amount of ethyl chloroacetate (1.67 mL, 15.7 mmol, 0.2 eq.) was then added. The reaction mixture was heated under reflux for 6 hours. The cooled suspension was then filtered and the solid residue was washed with DCM. The filtrate was reduced under vacuum and, after column chromatographic purification (SiO$_2$, heptane/EtOAc 2:3), 16.16 g (98%) of the desired product (2-cyanoimino-piperidin-1-yl)-acetic acid ethyl ester (D) was obtained.

c) Synthesis of 2-amino-5,6,7,8-tetrahydro-imidazo[1,2-a]-pyridine-3-carboxylic-acid ethyl ester

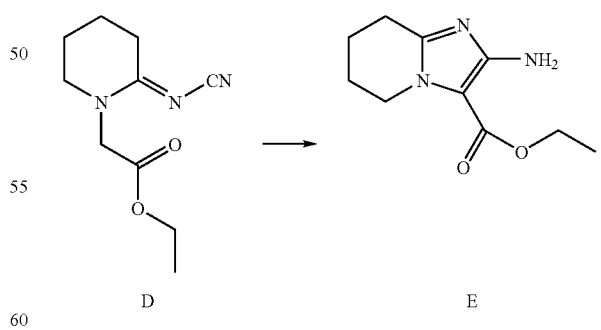

Compound D (16.05 g, 76.7 mmol) was added to a solution of sodium ethanolate (5.20 g, 76.7 mmol, 1.0 eq.) in ethanol (500 mL) and the resulting reaction mixture was heated for 30 minutes under reflux. The solvent was removed under vacuum and the untreated product was purified by means of column chromatography (hydromatrix as the adsorbent, SiO$_2$, DCM/3% MeOH→DCM/5% MeOH). 9.27 g of the desired product E were obtained. The columns were washed with methanol, the solvent was removed under vacuum and the residue was recrystallised by heptane in order to obtain a further 3.26 g of the desired product 2-amino-5,6,7,8-tetrahydro-imidazo[1,2-a]-pyridine-3-carboxylic-acid ethyl ester (E). In total, 12.53 g (78%) of the desired product 2-amino-5,6,7,8-tetrahydro-imidazo[1,2-a]-pyridine-3-carboxylic-acid ethyl ester (E) were obtained.

d) Synthesis of 2-butylamino-5,6,7,8-tetrahydro-imidazo[1,2-a]pyridine-3-carboxylic acid ethyl ester

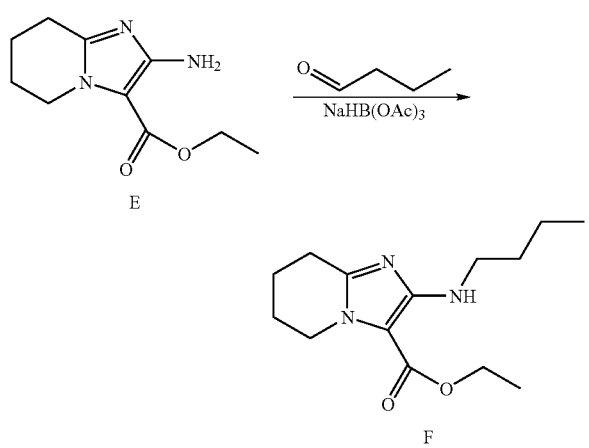

Compound E was dissolved in DCE (150 mL) and n-butylaldehyde (49.7 mmol, 4.4 mL, 1.5 eq.) was added thereto. Sodium triacetoxyborohydride (11.93 g, 56.3 mmol, 1.7 eq.) was then gradually added and the reaction mixture was stirred for four hours at room temperature. The reaction mixture was diluted with DCM (500 ml) and washed with saturated aqueous NaHCO$_3$ solution (500 mL). The aqueous phases were extracted with DCM (100 mL) and the combined organic phases were washed with saturated aqueous NaCl solution (500 mL), dried over sodium sulphate and the solvent was removed under vacuum. The untreated product was purified by means of column chromatography (SiO$_2$, heptane/EtOAc 4:1→3:1) and 5.7 g (65%) of the desired product 2-butylamino-5,6,7,8-tetrahydro-imidazo[1,2-a]pyridine-3-carboxylic acid ethyl ester (F) were obtained.

e) Synthesis of Example Compounds 43, 91 and 133

1) Synthesis of compound 2-[butyl-(3-chlorobenzoyl)-amino]-5,6,7,8-tetrahydro-imidazo[1,2-a]pyridine-3-carboxylic acid ethyl ester

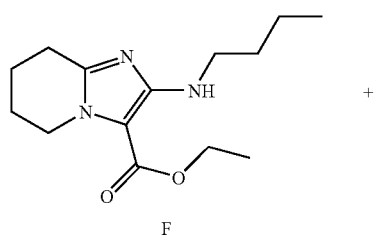

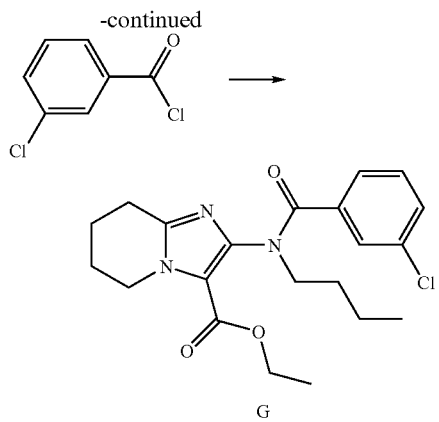

Compound F (3.1 g, 11.7 mmol) and triethylamine (2.46 ml, 17.5 mmol, 1.5 eq.) were dissolved in DCM (70 mL) and the reaction mixture was cooled in an ice bath. 3-chlorobenzyolchloride (1.65 mL, 12.85 mmol, 1.1 eq.) was then added dropwise thereto. After 90 minutes the reaction mixture was diluted with DCM (130 mL) and then washed several times with 0.5 M KHSO$_4$ in water (200 mL), saturated aqueous NaHCO$_3$ solution (200 mL) and saturated aqueous NaCl solution (200 mL). The organic phase was dried over sodium sulphate and the solvent was removed under vacuum. The untreated product 2-[butyl-(3-chlorobenzoyl)-amino]-5,6,7,8-tetrahydro-imidazo[1,2-a]pyridine-3-carboxylic acid ethyl ester was purified by means of column chromatography (SiO$_2$, DCM→DCM/5% MeOH) and used directly in the next stage.

2) Synthesis of 2-[butyl-(3-chloro-benzoyl)-amino]-5,6,7,8-tetrahydro-imidazo[1,2-a]pyridine-3-carboxylic acid

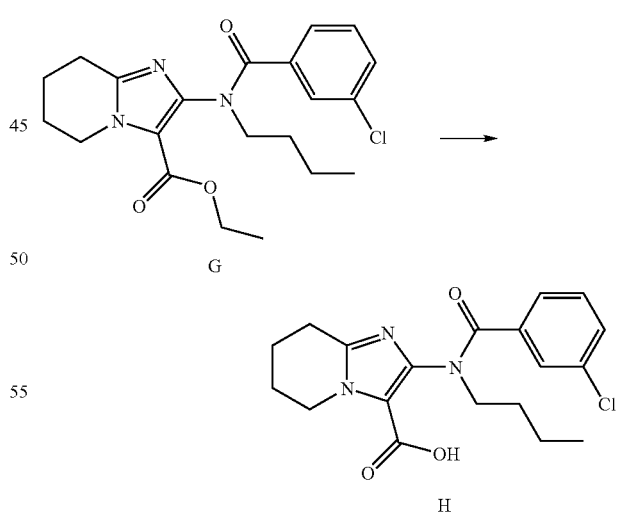

2-[butyl-(3-chloro-benzoyl)-amino]-5,6,7,8-tetrahydro-imidazo[1,2-a]pyridine-3-carboxylic acid ethyl ester (11.7 mmol) was dissolved in a solution of 190 mL MeOH/dioxan/4 M NaOH in water in a ratio of 15/4/1 and the solution was stirred over night at room temperature. The solvent was removed under vacuum, EtOAc (700 mL) was added thereto and the organic phase was washed with 0.5 M KHSO$_4$ in water (700 mL). The aqueous phase was extracted with EtOAc (300 mL) and the combined organic phases were washed with saturated aqueous NaCl solution (700 mL) and dried over sodium sulphate, and the solvent was removed under vacuum. 4.13 g (94% over two stages) of the desired product 2-[butyl-(3-chloro-benzoyl)-amino]-5,6,7,8-tetrahydro-imidazo[1,2-a]pyridine-3-carboxylic acid were obtained.

3) Synthesis of Example Compound 43

2-[butyl-(3-chloro-benzoyl)-amino]-5,6,7,8-tetrahydro-imidazo[1,2-a]pyridine-3-carboxylic acid 2-ethoxy-benzyl amide

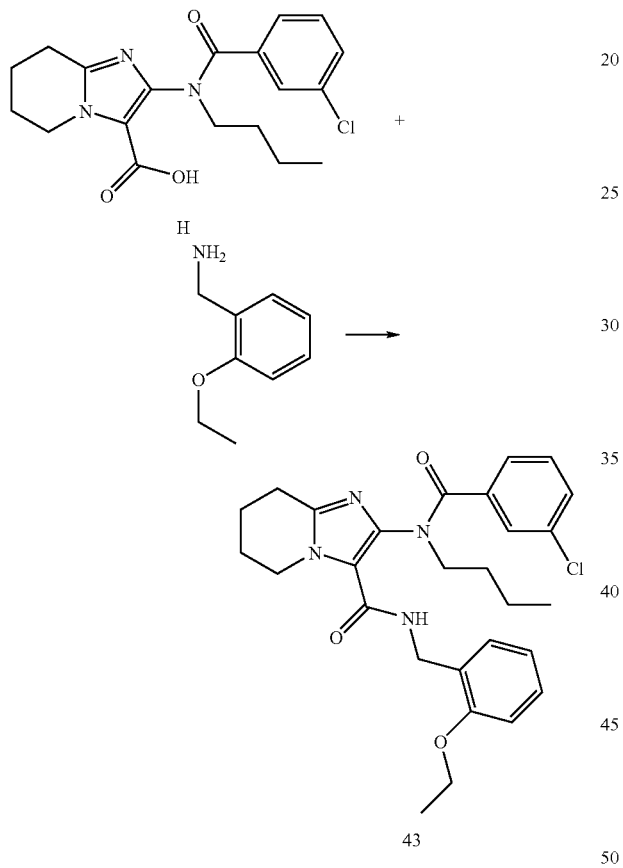

43

2-[butyl-(3-chloro-benzoyl)-amino]-5,6,7,8-tetrahydro-imidazo[1,2-a]pyridine-3-carboxylic acid (130 mg, 0.45 mmol), EDCI (72.9 mg, 0.38 mmol, 1.0 eq.) and HOAt (4.7 mg, 0.035 mmol, 0.1 eq.) were dissolved in DCM (3.5 mL). ortho-phenetidine (51.5 µL, 0.35 mmol) was added thereto and the solution was stirred for 16 hours at room temperature. The solvent was removed under vacuum, EtOAc (30 mL) was added thereto and the organic phase was washed a plurality of times with a 0.5 M solution of KHSO$_4$ in water (30 mL) and saturated aqueous NaHCO$_3$ solution (35 mL). The aqueous phases were shaken out a plurality of times with ethyl acetate. The combined organic phases were washed with saturated aqueous NaCl solution (40 mL) and dried over sodium sulphate, and the solvent was removed under vacuum. The untreated product was purified by column chromatography (SiO$_2$, DCM→DCM/MeOH 98/2). 130 mg (73%) of the desired product 2-[butyl-(3-chloro-benzoyl)-amino]-5,6,7,8-tetrahydro-imidazo[1,2-a]pyridine-3-carboxylic acid were obtained.

MS: [M$^+$] 509.6

4) Synthesis of Example Compound 91

2-({2-[butyl-(3-chloro-benzoyl)-amino]-5,6,7,8-tetrahydro-imidazo[1,2-a]pyridine-3-carbonyl}-amino)-3-(S)-methyl-benzyl butyrate

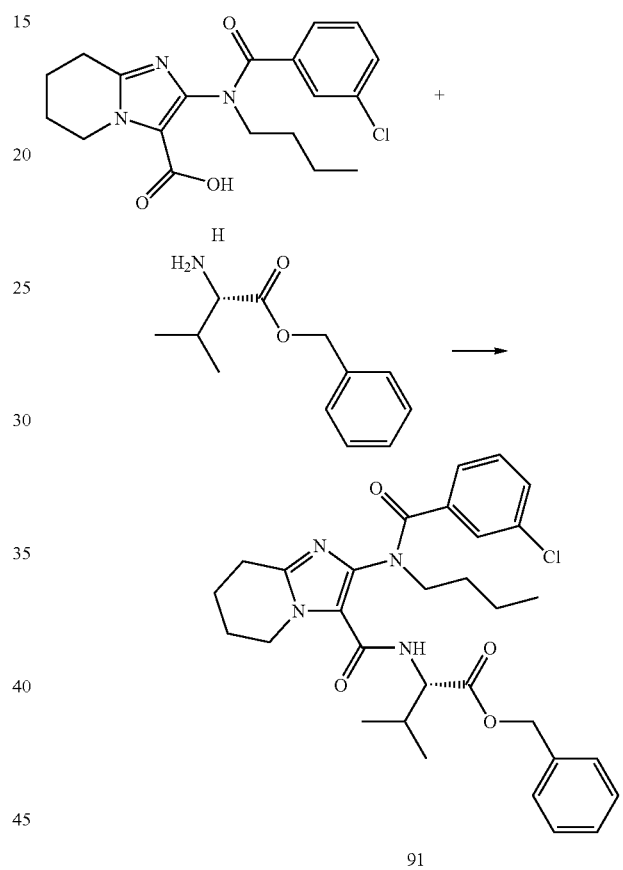

91

2-[butyl-(3-chloro-benzoyl)-amino]-5,6,7,8-tetrahydro-imidazo[1,2-a]pyridine-3-carboxylic acid (0.50 g, 1.33 mmol), L-valinebenzylesterhydrochloride (324 mg, 1.33 mmol), DIPEA (172 mg, 1.33 mmol) and HOAt (18 mg, 0.13 mmol) were dissolved in 10 mL DCM. The solution was cooled to 0° C. and EDCI (280 mg, 1.46 mmol) was added thereto. The solution was then stirred for 1 hour at 0° C. and stirred over night at room temperature. DCM (50 mL) and saturated aqueous NaCl solution (50 mL) were added thereto and the aqueous phase was extracted with DCM (50 mL). The combined organic phases were dried over sodium sulphate and the solvent was removed under vacuum. The untreated product was purified by column chromatography (SiO$_2$, DCM/MeOH 98/2). 473 mg (63%) of the desired product 2-({2-[butyl-(3-chloro-benzoyl)-amino]-5,6,7,8-tetrahydroimidazo[1,2-a]pyridine-3-carbonyl}-amino)-3-(S)-methyl-benzyl butyrate were obtained. -

5) Synthesis of Example Compound 132

2-[butyl-(3-chloro-benzoyl)-amino]-5,6,7,8-tetrahydro-imidazo[1,2-a]pyridine-3-carboxylic acid (1-R-phenyl-propyl)-amide

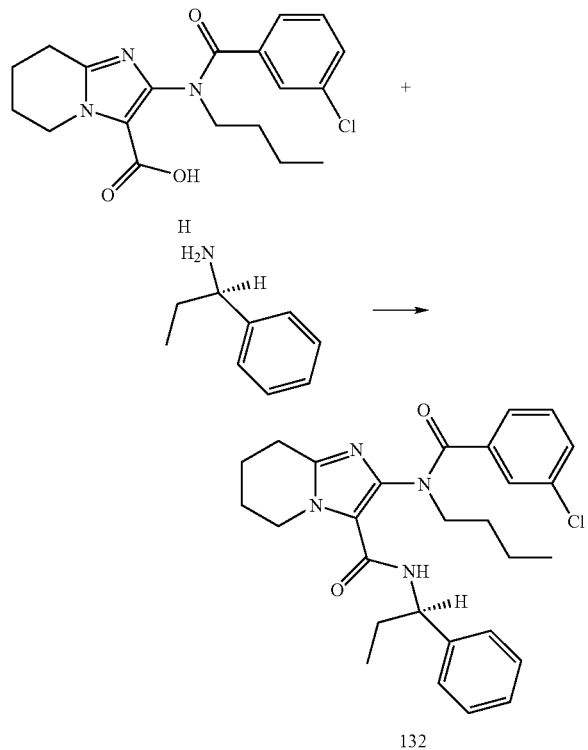

132

2-[butyl-(3-chloro-benzoyl)-amino]-5,6,7,8-tetrahydro-imidazo[1,2-a]pyridine-3-carboxylic acid (0.50 g, 1.33 mmol), R-(+)-1-phenylpropylamine (180 mg, 1.33 mmol) and HOAt (18 mg, 0.13 mmol) were dissolved in 5 mL DCM. The solution was cooled to 0° C. and EDCI (280 mg, 1.46 mmol) was added thereto. The reaction mixture was stirred for 1 hour at 0° C. and then over night at room temperature. DCM (50 mL) and saturated aqueous NaCl solution (50 mL) were added thereto and the aqueous phase was extracted with 50 mL DCM. The combined organic phases were dried over sodium sulphate and the solvent was removed under vacuum. The untreated product was purified by column chromatography (SiO$_2$, DCM/MeOH 98/2) and 492 mg (75%) of the desired product 2-[butyl-(3-chlor-benzoyl)-amino]-5,6,7,8-tetrahydro-imidazo[1,2-a]pyridine-3-carboxylic acid (1-(R)-phenyl-propyl)-amide were obtained.

f) Synthesis of Example Compounds 16, 93 and 180

1) Synthesis of 2-[butyl-(3,4-difluoro-benzoyl)-amino]-5,6,7,8-tetrahydro-imidazo[1,2-a]pyridine-3-carboxylic acid ethyl ester

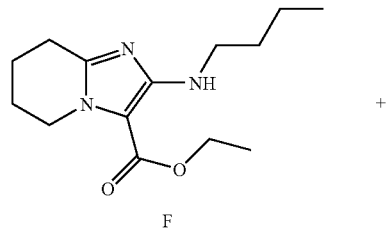

F

-continued

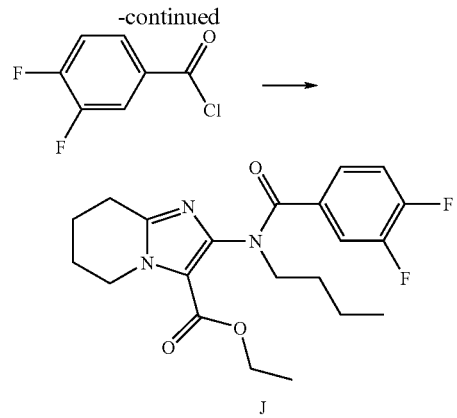

J

Compound F (3.2 g, 12.1 mmol) and triethylamine (2.54 mL, 18.1 mmol, 1.5 eq.) were dissolved in DCM (70 mL) and the solution was cooled to 0° C. 3,4-difluorobenzoylchloride (1.66 mL, 13.3 mmol, 1.1 eq.) was added dropwise. After 90 minutes the reaction mixture was diluted with DCM (130 mL) and washed with 0.5 M KHSO$_4$ in water (200 mL), saturated aqueous NaHCO$_3$ solution (200 mL) and saturated aqueous NaCl solution (200 mL). The combined organic phases were dried over sodium sulphate and the solvent was removed under vacuum and the untreated product 2-[butyl-(3,4-difluoro-benzoyl)-amino]-5,6,7,8-tetrahydro-imidazo[1,2-a]pyridine-3-carboxylic acid ethyl ester was used directly in the next stage.

2) Synthesis of 2-[butyl-(3,4-difluoro-benzoyl)-amino]-5,6,7,8-tetrahydro-imidazo[1,2-a]pyridine-3-carboxylic acid

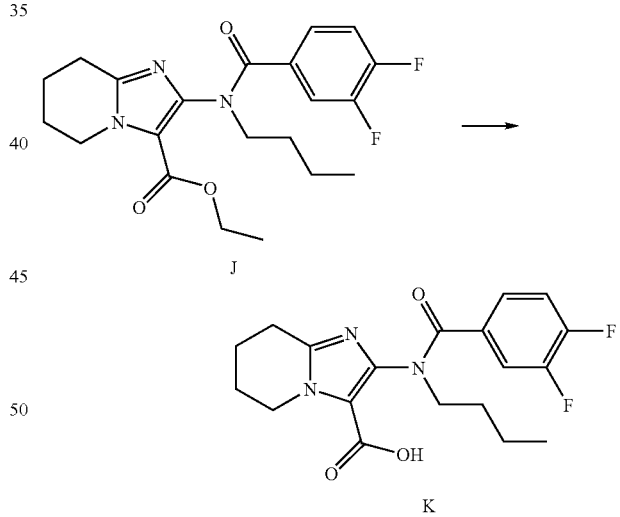

K

Compound J (12.1 mmol) was dissolved in a solution of 200 mL MeOH/dioxan/4 M NaOH in water in a ratio of 15/4/1 and the solution was stirred over night at room temperature. The solvent was removed under vacuum, EtOAc (700 mL) was added thereto and the organic phase was washed with 0.5 M KHSO$_4$ in water (700 mL). The aqueous phase was extracted with EtOAc (300 mL) and the combined organic phases were washed with saturated aqueous NaCl solution (700 mL) and dried over sodium sulphate, and the solvent was removed under vacuum. 4.38 g (96% over two stages) of the desired product 2-[butyl-(3,4-difluoro-benzoyl)-amino]-5,6,7,8-tetrahydro-imidazo[1,2-a]pyridine-3-carboxylic acid were obtained.

3) Synthesis of Example Compound 16

2-[butyl-(3,4-difluoro-benzoyl)-amino]-5,6,7,8-tetrahydro-imidazo[1,2-a]pyridine-3-carboxylic acid (4-methyl-cyclohexyl)-amide

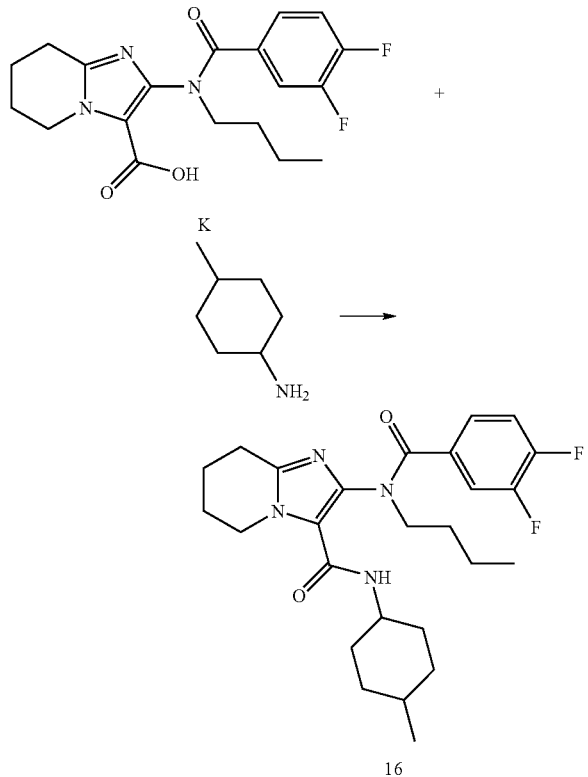

16

Compound K (0.50 g, 1.33 mmol), 4-methyl-cyclohexylamine (149 mg, 1.33 mmol, mixture of cis- and trans-isomers), DIPEA (172 mg, 1.33 mmol) and HOAt (18 mg, 0.13 mmol) were dissolved in 10 mL DCM. The solution was cooled to 0° C. and EDCI (280 mg, 1.46 mmol) was added thereto. The solution was then stirred for 1 hour at 0° C. and over night at room temperature. DCM (50 mL) and saturated aqueous NaCl solution (50 mL) were added thereto and the aqueous phase was extracted with DCM (50 mL). The combined organic phases were dried over sodium sulphate and the solvent was removed under vacuum. The untreated product was purified by column chromatography (SiO$_2$, DCM/MeOH 98/2). 418 mg (67%) of the desired product 2-[butyl-(3,4-difluoro-benzoyl)-amino]-5,6,7,8-tetrahydro-imidazo[1,2-a]pyridine-3-carboxylic acid (4-methyl-cyclohexyl)-amide were obtained.

4) Synthesis of Example Compound 93

2-[butyl-(3,4-difluoro-benzoyl)-amino]-5,6,7,8-tetrahydro-imidazo[1,2-a]pyridine-3-carboxylic acid (2-methyl-cyclohexyl)-amide

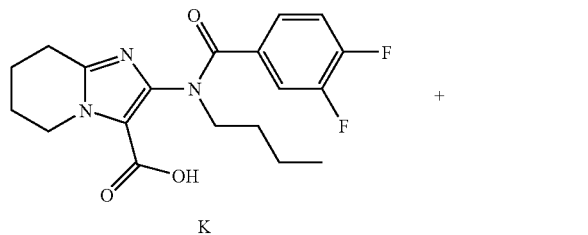

K

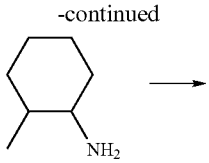

-continued

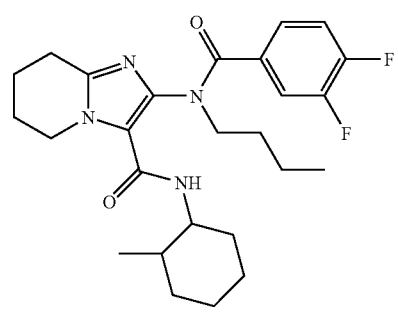

93

Compound K (0.50 g, 1.33 mmol), 2-methyl-cyclohexylamine (149 mg, 1.33 mmol, mixture of cis- and trans-isomers), DIPEA (172 mg, 1.33 mmol) and HOAt (18 mg, 0.13 mmol) were dissolved in 10 mL DCM. The solution was cooled to 0° C. and EDCI (280 mg, 1.46 mmol) was added thereto. The solution was then stirred for 1 hour at 0° C. and over night at room temperature. DCM (50 mL) and saturated aqueous NaCl solution (50 mL) were added thereto and the aqueous phase was extracted with DCM (50 mL). The combined organic phases were dried over sodium sulphate and the solvent was removed under vacuum. The untreated product was purified by column chromatography (SiO$_2$, DCM/MeOH 98/2). 272 mg (43%) of the desired product 2-[butyl-(3,4-difluoro-benzoyl)-amino]-5,6,7,8-tetrahydro-imidazo[1,2-a]pyridine-3-carboxylic acid (2-methyl-cyclohexyl)-amide were obtained.

5) Synthesis of Example Compound 180

2-[(3-chloro-benzoyl)-methyl-amino]-5,6,7,8-tetrahydro-imidazo[1,2-a]pyridine-3-carboxylic acid (3,3-diphenyl-propyl)-amide

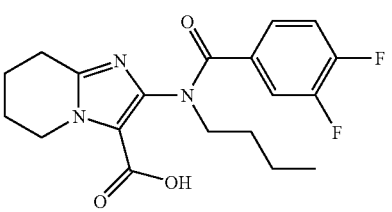

K

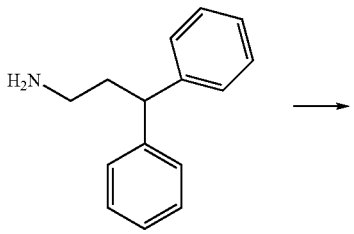

-continued

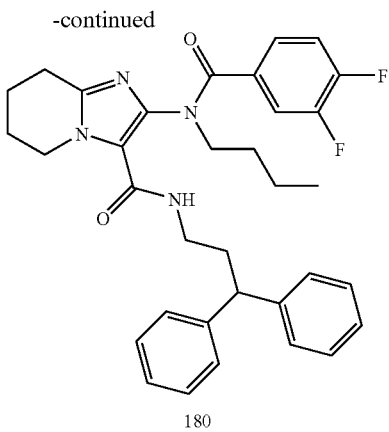

180

Compound K (0.50 g, 1.32 mmol),3,3-diphenylpropylamine (279 mg, 1.32 mmol) and HOAt (18 mg, 0.13 mmol) were dissolved in 10 mL DCM. The solution was cooled to 0° C. and EDCI (278 mg, 1.45 mmol) was added thereto. The reaction mixture was stirred for 1 hour at 0° C. and over night at room temperature. DCM (50 mL) and saturated aqueous NaCl solution (50 mL) were added thereto and the aqueous phase was extracted with DCM (50 mL). The combined organic phases were dried over sodium sulphate and the solvent was removed under vacuum. The untreated product was purified by column chromatography (SiO$_2$, DCM/MeOH 98/2). 507 mg (67%) of the desired product 2-[(3-chloro-benzoyl)-methyl-amino]-5,6,7,8-tetrahydro-imidazo[1,2-a]pyridine-3-carboxylic acid (3,3-diphenyl-propyl)-amide were obtained.

g) Synthesis of Example Compound 121

1) Synthesis of 2-(3-chlorobenzoylamino)-5,6,78-tetrahydro-imidazo[1,2-a]-pyridine-3-carboxylic acid ethyl ester

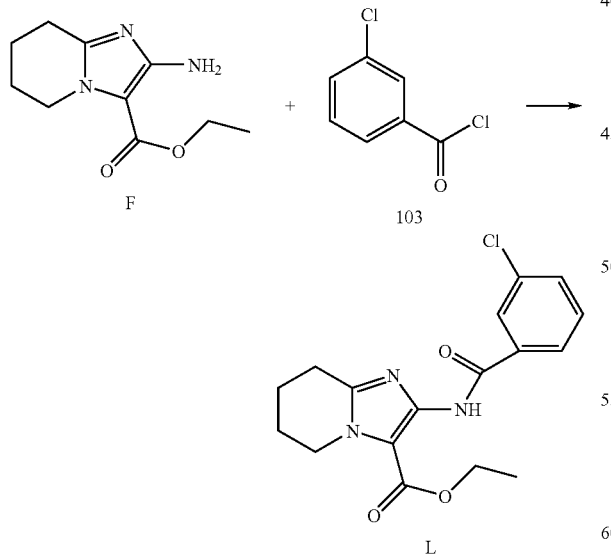

Compound F; (521 mg, 2.5 mmol) was dissolved in dioxan (10 mL), and 3-chlorobenzoylchloride (320 µL, 2.5 mmol) was then added dropwise thereto. The reaction mixture was stirred over night at room temperature and additional amounts of the acid chloride (16 µL, 0.12 mmol) were added thereto. After one hour, the reaction mixture was diluted with EtOAc (250 mL) and then washed in succession with saturated aqueous NaHCO$_3$ solution (250 mL) and 0.5 M KHSO$_4$ in water (250 mL). The aqueous phases were washed with EtOAc (50 mL), and the combined organic phases were in turn washed with saturated aqueous NaCl solution (250 mL) and dried over sodium sulphate, and the solvent was removed under vacuum. 481.6 mg (55%) of the desired product 2-(3-chlorobenzoylamino)-5,6,7,8-tetrahydro-imidazo[1,2-a]pyridine-3-carboxylic acid ethyl ester (L) were obtained.

2) Synthesis of 2-[(3-chloro-benzoyl)-methyl-amino]-5,6,7,8-tetrahydro-imidazo[1,2-a]pyridine-3-carboxylic acid ethyl ester and 2-[(3-chloro-benzoyl)-methyl-amino]-5,6,7,8-tetrahydro-imidazo[1,2-a]pyridine-3-carboxylic acid methyl ester

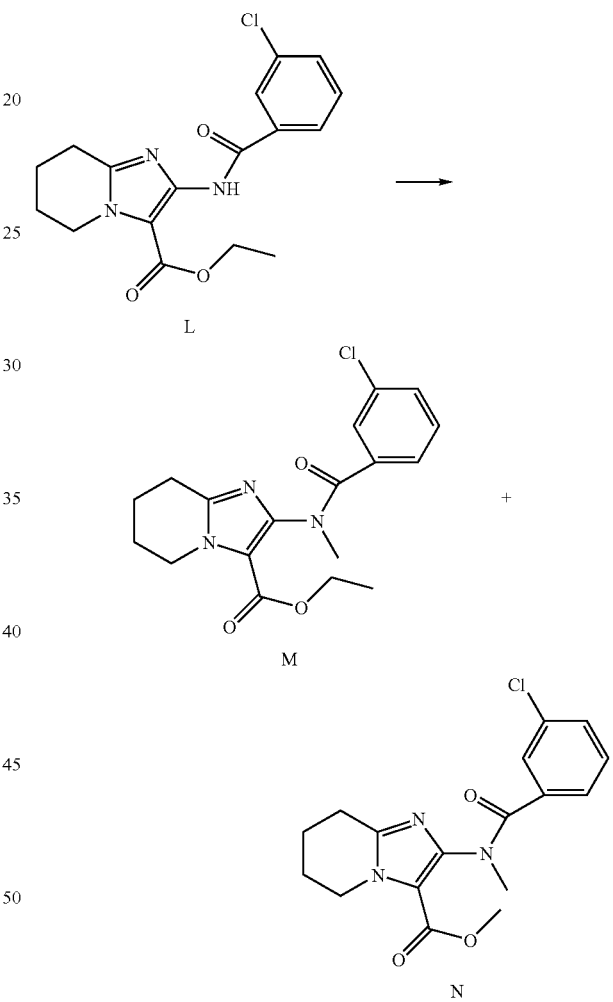

Sodium hydride (60% suspension in paraffin oil, 148.9 mg, 3.7 mmol, 3.7 eq.) was washed twice with heptane and taken up in DMF. A solution of compound L (350 mg, 1.0 mmol) in DMF was added dropwise thereto. After 25 minutes at room temperature, a solution of methyl iodide in DMF (1.6 M, 1.9 mL, 3 mmol, 3 eq.) was slowly added dropwise thereto and the reaction mixture was stirred over night at room temperature. Further methyl iodide (62 µL, 1.0 mmol, 1 eq.) was added thereto and the mixture was again stirred over night. The reaction mixture was diluted with EtOAc (300 mL) and poured into 0.5 M KHSO$_4$ in water (300 mL). The phases were separated and the aqueous phase was extracted with EtOAc (300 mL). The combined organic phases were washed with saturated aqueous NaCl solution (70 mL) and dried over sodium sulphate, and the solvent was removed under vacuum. 0.294 g of a mixture of 2-[(3-chloro-benzoyl)-methyl-amino]-5,6,7,8-tetrahydro-imidazo[1,2-a]pyridine-3-carboxylic acid ethyl ester and 2-[(3-chloro-benzoyl)-methyl-amino]-5,6,7,8-tetrahydro-imidazo[1,2-a]pyridine-3-carboxylic acid methyl ester was obtained and used directly in the next stage.

3) Synthesis of 2-[(3-chloro-benzoyl)-methyl-amino]-5,6,7,8-tetrahydro-imidazo[1,2-a]pyridine-3-carboxylic acid

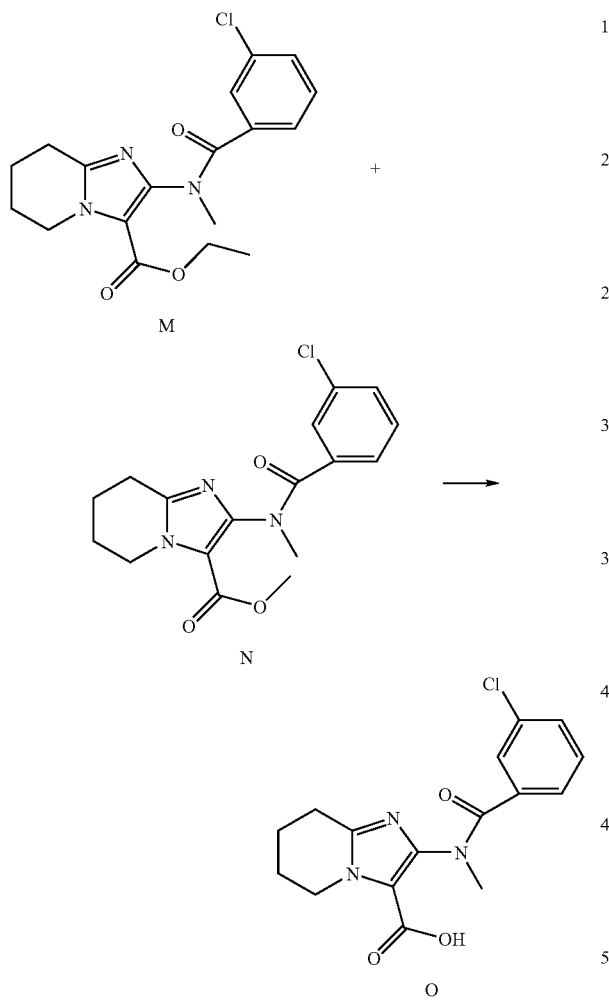

2-[(3-chloro-benzoyl)-methyl-amino]-5,6,7,8-tetrahydro-imidazo[1,2-a]pyridine-3-carboxylic acid ethyl ester and 2-[(3-chloro-benzoyl)-methyl-amino]-5,6,7,8-tetrahydro-imidazo[1,2-a]pyridine-3-carboxylic acid methyl ester (1.0 mmol together) were dissolved in a solution of 16 mL MeOH/dioxan/4 M NaOH in water in a ratio of 15/4/1, and the solution was stirred over night at room temperature. Further NaOH in water (1.5 mL, 6 mmol) was added thereto. After 45 minutes the solvent was removed under vacuum, EtOAc (60 mL) was added thereto and the organic phase was washed with 0.5 M KHSO$_4$ in water (50 mL). The aqueous phase was extracted with EtOAc (60 mL), the combined organic phases were washed with saturated aqueous NaCl solution (80 mL) and dried over sodium sulphate, and the solvent was removed under vacuum. 234 g (70% over two stages) of the desired product 2-(3-chloro-benzoyl)-methyl-amino]-5,6,7,8-tetrahydro-imidazo[1,2-a]pyridine-3-carboxylic acid were obtained.

4) Synthesis of Example Compound 121

2-[(3-chloro-benzoyl)-methyl-amino]-5,6,7,8-tetrahydro-imidazo[1,2-a]pyridine-3-carboxylic acid (benzo[1,3]dioxol-5-ylmethyl)-amide

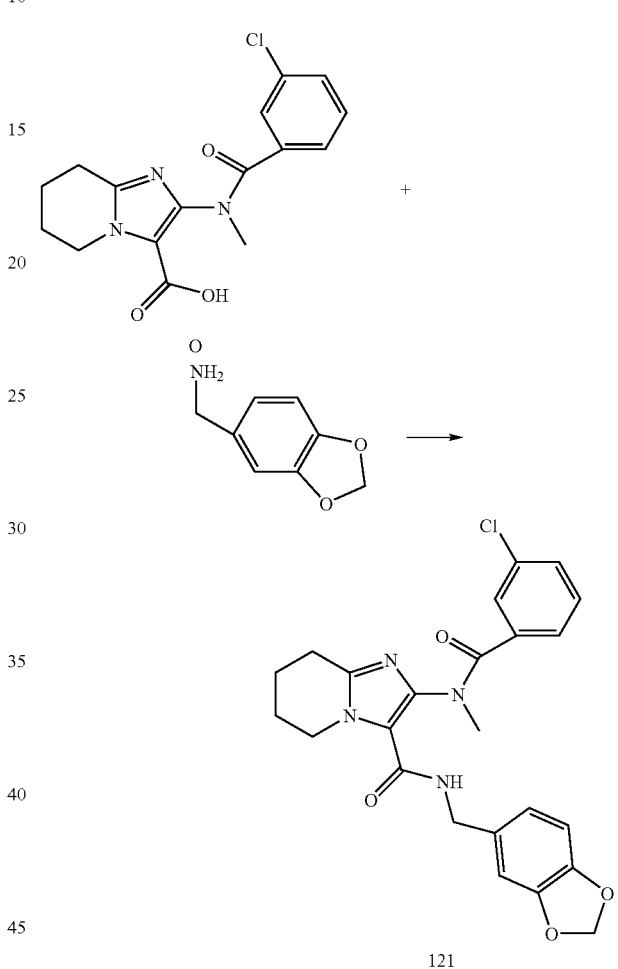

2-[(3-chloro-benzoyl)-methyl-amino]-5,6,7,8-tetrahydro-imidazo[1,2-a]pyridine-3-carboxylic acid (232 mg, 0.70 mmol), EDCI (146.6 mg, 0.76 mmol, 1.1 eq.) and HOAt (9.5 mg, 0.07 mmol, 0.1 eq.) were dissolved in DCM (10 mL). Piperonylamine (96 µL, 0.77 mmol, 1.1 eq.) was then added thereto. The reaction mixture was stirred over night and the solvent was then removed. EtOAc (70 mL) was added thereto and the reaction mixture was washed in succession with 0.5 M KHSO$_4$ in water (70 mL) and saturated aqueous NaHCO$_3$ solution (70 mL). The aqueous phases were extracted with EtOAc (30 mL). The combined organic phases were washed with saturated aqueous NaCl solution (70 mL), dried over sodium sulphate, and the solvent was removed under vacuum. The untreated product was purified by column chromatography (SiO$_2$, DCM→DCM/2% MeOH). 116.8 mg (36%) of the desired product 2-[(3-chloro-benzoyl)-methyl-amino]-5,6,7,8-tetrahydro-imidazo[1,2-a]pyridine-3-carboxylic acid (benzo[1,3]dioxol-5-ylmethyl)-amide were obtained.

MS: [M+H$^+$]467.6

The production, not described in detail hereinbefore, of the remaining compounds according to the following examples was also carried out in a manner similar to the foregoing directions for production, the educts used in each case being known to the person skilled in the art.

| Example | Name |
|---|---|
| 1 | 2-[(3-chloro-benzoyl)-methyl-amino]-5,6,7,8-tetrahydro-imidazo[1,2-a]pyridine-3-carboxylic acid (2-thiophen-2-yl-ethyl)-amide |
| 2 | 2-[butyl-(3-chloro-benzoyl)-amino]-5,6,7,8-tetrahydro-imidazo[1,2-a]pyridine-3-carboxylic acid [2-(2,5-dimethoxy-phenyl)-ethyl]-amide |
| 3 | N-{3-[4-(2-ethyl-phenyl)-piperazine-1-carbonyl]-5,6,7,8-tetrahydro-imidazo[1,2-a]pyridin-2-yl}-N-methyl-benzamide |
| 4 | 2-(methyl-phenylacetyl-amino)-5,6,7,8-tetrahydro-imidazo[1,2-a]pyridine-3-carboxylic acid [3-(2-methyl-piperidin-1-yl)-propyl]-amide |
| 5 | 2-[(3-chloro-benzoyl)-methyl-amino]-5,6,7,8-tetrahydro-imidazo[1,2-a]pyridine-3-carboxylic acid (2-phenyl-propyl)-amide |
| 6 | 2-[(3-chloro-benzoyl)-methyl-amino]-5,6,7,8-tetrahydro-imidazo[1,2-a]pyridine-3-carboxylic acid (2-pyrrolidin-1-yl-ethyl)-amide |
| 7 | 2-[methyl-(naphthalene-1-carbonyl)-amino]-5,6,7,8-tetrahydro-imidazo[1,2-a]pyridine-3-carboxylic acid ethyl-pyridin-4-ylmethyl-amide |
| 8 | 2-(benzoyl-methyl-amino)-5,6,7,8-tetrahydro-imidazo[1,2-a]pyridine-3-carboxylic acid (2-thiophen-2-yl-ethyl)-amide |
| 9 | 2-[butyl-(3-chloro-benzoyl)-amino]-5,6,7,8-tetrahydro-imidazo[1,2-a]pyridine-3-carboxylic acid (3-imidazol-1-yl-propyl)-amide |
| 10 | 3-chloro-N-{3-[4-(3-chlorophenyl)-piperazine-1-carbonyl]-5,6,7,8-tetrahydro-imidazo[1,2-a]pyridin-2-yl}-N-methyl-benzamide |
| 11 | 3-chloro-N-methyl-N-[3-(4-phenyl-piperazine-1-carbonyl)-5,6,7,8-tetrahydro-imidazo[1,2-a]pyridin-2-yl]-benzamide |
| 12 | 2-[butyl-(3,4-difluoro-benzoyl)-amino]-5,6,7,8-tetrahydro-imidazo[1,2-a]pyridine-3-carboxylic acid indan-1-ylamide |
| 13 | N-butyl-3-chloro-N-{3-[4-(2-morpholin-4-yl-ethyl)-piperazine-1-carbonyl]-5,6,7,8-tetrahydro-imidazo[1,2-a]pyridin-2-yl}-benzamide |
| 14 | 3-chloro-N-methyl-N-{3-[4-(3-trifluoromethyl-phenyl)-piperazine-1-carbonyl]-5,6,7,8-tetrahydro-imidazo[1,2-a]pyridin-2-yl}-benzamide |
| 15 | 2-[Methyl-(naphthalene-1-carbonyl)-amino]-5,6,7,8-tetrahydro-imidazo[1,2-a]pyridine-3-carboxylic acid 3,5-bis-trifluoromethyl-benzylamide |
| 16 | 2-[butyl-(3,4-difluoro-benzoyl)-amino]-5,6,7,8-tetrahydro-imidazo[1,2-a]pyridine-3-carboxylic acid (4-methyl-cyclohexyl)-amide |
| 17 | 2-(benzoyl-methyl-amino)-5,6,7,8-tetrahydro-imidazo[1,2-a]pyridine-3-carboxylic acid 3-methoxy-benzylamide |
| 18 | 2-[methyl-(naphthalene-1-carbonyl)-amino]-5,6,7,8-tetrahydro-imidazo[1,2-a]pyridine-3-carboxylic acid (1-p-tolyl-ethyl)-amide |
| 19 | 2-[butyl-(3-chloro-benzoyl)-amino]-5,6,7,8-tetrahydro-imidazo[1,2-a]pyridine-3-carboxylic acid (1,2-dimethyl-propyl)-amide |
| 20 | 2-(benzoyl-methyl-amino)-5,6,7,8-tetrahydro-imidazo[1,2-a]pyridine-3-carboxylic acid (4-methyl-cyclohexyl)-amide |
| 21 | 2-(benzoyl-methyl-amino)-5,6,7,8-tetrahydro-imidazo[1,2-a]pyridine-3-carboxylic acid (2-phenyl-propyl)-amide |
| 22 | 4-[2-(benzoyl-methyl-amino)-5,6,7,8-tetrahydro-imidazo[1,2-a]pyridine-3-carbonyl]-piperazine-1-carboxylic acid ethyl ester |
| 23 | 3-chloro-N-methyl-N-(3-{4-[(methyl-phenyl-carbamoyl)-methyl]-piperazine-1-carbonyl}-5,6,7,8-tetrahydro-imidazo[1,2-a]pyridin-2-yl)-benzamide |
| 24 | 3-chloro-N-{3-[4-(furan-2-carbonyl)-piperazine-1-carbonyl]-5,6,7,8-tetrahydro-imidazo[1,2-a]pyridin-2-yl}-N-methyl-benzamide |
| 25 | N-methyl-N-[3-(4-p-tolyl-piperazine-1-carbonyl)-5,6,7,8-tetrahydro-imidazo[1,2-a]pyridin-2-yl]-benzamide |
| 26 | N-butyl-3-chloro-N-{3-[4-(3-phenyl-propyl)-piperazine-1-carbonyl]-5,6,7,8-tetrahydro-imidazo[1,2-a]pyridin-2-yl}-benzamide |
| 27 | 2-[(3-chloro-benzoyl)-methyl-amino]-5,6,7,8-tetrahydro-imidazo[1,2-a]pyridine-3-carboxylic acid (2,6,6-trimethyl-bicyclo[3.1.1]hept-3-yl)-amide |
| 28 | 2-[butyl-(3,4-difluoro-benzoyl)-amino]-5,6,7,8-tetrahydro-imidazo[1,2-a]pyridine-3-carboxylic acid (3-phenyl-propyl)-amide |
| 29 | naphthalene-1-carboxylic acid {3-[4-(4-methoxy-phenyl)-piperazine-1-carbonyl]-5,6,7,8-tetrahydro-imidazo[1,2-a]pyridin-2-yl}-methyl-amide |
| 30 | 2-[methyl-(naphthalene-1-carbonyl)-amino]-5,6,7,8-tetrahydro-imidazo[1,2-a]pyridine-3-carboxylic acid [1-(4-trifluoromethyl-benzyl)-pyrrolidin-3-yl]-amide |
| 31 | 2-[(3-chloro-benzoyl)-methyl-amino]-5,6,7,8-tetrahydro-imidazo[1,2-a]pyridine-3-carboxylic acid (4-ethyl-phenyl)-amide |

-continued

| Example | Name |
|---|---|
| 32 | 2-[methyl-(naphthalene-1-carbonyl)-amino]-5,6,7,8-tetrahydro-imidazo[1,2-a]pyridine-3-carboxylic acid (3-methoxy-benzyl)-(tetrahydro-furan-2-ylmethyl)-amide |
| 33 | 2-[methyl-(naphthalene-1-carbonyl)-amino]-5,6,7,8-tetrahydro-imidazo[1,2-a]pyridine-3-carboxylic acid 2,3-dichlor-benzylamide |
| 34 | 2-[butyl-(3,4-difluoro-benzoyl)-amino]-5,6,7,8-tetrahydro-imidazo[1,2-a]pyridine-3-carboxylic acid (1-benzofuran-2-ylmethyl-pyrrolidin-3-yl)-methyl-amide |
| 35 | 3-chloro-N-{3-[4-(4-chloro-phenyl)-piperazine-1-carbonyl]-5,6,7,8-tetrahydro-imidazo[1,2-a]pyridin-2-yl}-N-methyl-benzamide |
| 36 | 2-({2-[(3-chloro-benzoyl)-methyl-amino]-5,6,7,8-tetrahydro-imidazo[1,2-a]pyridine-3-carbonyl}-amino)-3-(1H-indol-3-yl)-propanoic acid methyl ester |
| 37 | N-butyl-3-chloro-N-[3-(4-phenylacetyl-piperazine-1-carbonyl)-5,6,7,8-tetrahydro-imidazo[1,2-a]pyridin-2-yl]-benzamide |
| 38 | 2-({2-[(3-chloro-benzoyl)-methyl-amino]-5,6,7,8-tetrahydro-imidazo[1,2-a]pyridine-3-carbonyl}-amino)-3-methyl-pentanoic acid tert-butyl ester |
| 39 | 2-[butyl-(3-chloro-benzoyl)-amino]-5,6,7,8-tetrahydro-imidazo[1,2-a]pyridine-3-carboxylic acid (1-naphthalen-1-yl-ethyl)-amide |
| 40 | 2-[methyl-(naphthalene-1-carbonyl)-amino]-5,6,7,8-tetrahydro-imidazo[1,2-a]pyridine-3-carboxylic acid allyl methyl-amide |
| 41 | N-butyl-N-[3-(3,6-dihydro-2H-pyridine-1-carbonyl)-5,6,7,8-tetrahydro-imidazo[1,2-a]pyridin-2-yl]-3,4-difluoro-benzamide |
| 42 | 2-({2-[(3-chloro-benzoyl)-methyl-amino]-5,6,7,8-tetrahydro-imidazo[1,2-a]pyridine-3-carbonyl}-amino)-4-methyl-pentanoic acid benzyl ester |
| 43 | 2-[butyl-(3-chloro-benzoyl)-amino]-5,6,7,8-tetrahydro-imidazo[1,2-a]pyridine-3-carboxylic acid 2-ethoxy-benzylamide |
| 44 | N-butyl-3-chloro-N-{3-[4-(5-methyl-pyrazine-2-carbonyl)-piperazine-1-carbonyl]-5,6,7,8-tetrahydro-imidazo[1,2-a]pyridin-2-yl}-benzamide |
| 45 | N-[3-(4-benzo[1,3]dioxol-5-ylmethyl-piperazine-1-carbonyl)-5,6,7,8-tetrahydro-imidazo[1,2-a]pyridin-2-yl]-3-chloro-N-methyl-benzamide |
| 46 | 2-[methyl-(naphthalene-1-carbonyl)-amino]-5,6,7,8-tetrahydro-imidazo[1,2-a]pyridine-3-carboxylic acid (2,2-diphenyl-ethyl)-amide |
| 47 | 2-[butyl-(3-chloro-benzoyl)-amino]-5,6,7,8-tetrahydro-imidazo[1,2-a]pyridine-3-carboxylic acid 2,4-difluoro-benzylamide |
| 48 | N-butyl-3-chloro-N-{3-[4-(2-fluoro-phenyl)-piperazine-1-carbonyl]-5,6,7,8-tetrahydro-imidazo[1,2-a]pyridin-2-yl}-benzamide |
| 49 | 2-[methyl-(naphthalene-1-carbonyl)-amino]-5,6,7,8-tetrahydro-imidazo[1,2-a]pyridine-3-carboxylic acid (2-p-tolyl-ethyl)-amide |
| 50 | 2-[methyl-(naphthalene-1-carbonyl)-amino]-5,6,7,8-tetrahydro-imidazo[1,2-a]pyridine-3-carboxylic acid (pyridin-2-ylmethyl)-amide |
| 51 | 2-[butyl-(3-chloro-benzoyl)-amino]-5,6,7,8-tetrahydro-imidazo[1,2-a]pyridine-3-carboxylic acid 2-trifluoromethyl-benzylamide |
| 52 | 2-[butyl-(3-chloro-benzoyl)-amino]-5,6,7,8-tetrahydro-imidazo[1,2-a]pyridine-3-carboxylic acid indan-1-ylamide |
| 53 | 3-chloro-N-methyl-N-[3-(4-quinolin-2-ylmethyl-piperazine-1-carbonyl)-5,6,7,8-tetrahydro-imidazo[1,2-a]pyridin-2-yl]-benzamide |
| 54 | N-butyl-3,4-difluoro-N-[3-(4-methyl-piperazine-1-carbonyl)-5,6,7,8-tetrahydro-imidazo[1,2-a]pyridin-2-yl]-benzamide |
| 55 | 2-[(3-chloro-benzoyl)-methyl-amino]-5,6,7,8-tetrahydro-imidazo[1,2-a]pyridine-3-carboxylic acid 2,4-difluoro-benzylamide |
| 56 | N-[3-(4-benzhydryl-piperazine-1-carbonyl)-5,6,7,8-tetrahydro-imidazo[1,2-a]pyridin-2-yl]-N-butyl-3,4-difluoro-benzamide |
| 57 | 4-methyl-2-({2-[methyl-(naphthalene-1-carbonyl)-amino]-5,6,7,8-tetrahydro-imidazo[1,2-a]pyridine-3-carbonyl}-amino)-pentanoic acid benzyl ester |
| 58 | 2-[butyl-(3-chloro-benzoyl)-amino]-5,6,7,8-tetrahydro-imidazo[1,2-a]pyridine-3-carboxylic acid (2-pyrrolidin-1-yl-ethyl)-amide |
| 59 | 2-[(3-chloro-benzoyl)-methyl-amino]-5,6,7,8-tetrahydro-imidazo[1,2-a]pyridine-3-carboxylic acid [1-(2-benzyloxy-benzyl)-pyrrolidin-3-yl]-amide |
| 60 | 2-[butyl-(3,4-difluoro-benzoyl)-amino]-5,6,7,8-tetrahydro-imidazo[1,2-a]pyridine-3-carboxylic acid (pyridin-3-ylmethyl)-amide |
| 61 | 3-chloro-N-{3-[4-(4-fluorophenyl)-3,6-dihydro-2H-pyridine-1-carbonyl]-5,6,7,8-tetrahydro-imidazo[1,2-a]pyridin-2-yl}-N-methyl-benzamide |
| 62 | 2-[(3-chloro-benzoyl)-methyl-amino]-5,6,7,8-tetrahydro-imidazo[1,2-a]pyridine-3-carboxylic acid cyclohexylamide |
| 63 | N-[3-(4-cycloheptyl-piperazine-1-carbonyl)-5,6,7,8-tetrahydro-imidazo[1,2-a]pyridin-2-yl]-N-methyl-benzamide |
| 64 | naphthalene-1-carboxylic acid methyl-[3-(4-thiophen-3-ylmethyl-piperazine-1-carbonyl)-5,6,7,8-tetrahydro-imidazo[1,2-a]pyridin-2-yl]-amide |
| 65 | 2-[butyl-(3-chloro-benzoyl)-amino]-5,6,7,8-tetrahydro-imidazo[1,2-a]pyridine-3-carboxylic acid 2,4-dimethoxy-benzylamide |

-continued

| Example | Name |
|---|---|
| 66 | 1-[2-(benzoyl-methyl-amino)-5,6,7,8-tetrahydro-imidazo[1,2-a]pyridine-3-carbonyl]-piperidine-4-carboxylic acid ethyl ester |
| 67 | 2-[(3-chloro-benzoyl)-methyl-amino]-5,6,7,8-tetrahydro-imidazo[1,2-a]pyridine-3-carboxylic acid (2-benzyloxy-cyclohexyl)-amide |
| 68 | 2-[methyl-(naphthalene-1-carbonyl)-amino]-5,6,7,8-tetrahydro-imidazo[1,2-a]pyridine-3-carboxylic acid [2-(4-phenoxy-phenyl)-ethyl]-amide |
| 69 | 2-[butyl-(3-chloro-benzoyl)-amino]-5,6,7,8-tetrahydro-imidazo[1,2-a]pyridine-3-carboxylic acid [2-(7-methyl-1H-indol-3-yl)-ethyl]-amide |
| 70 | naphthalene-1-carboxylic acid methyl-[3-(4-phenyl-piperazine-1-carbonyl)-5,6,7,8-tetrahydro-imidazo[1,2-a]pyridin-2-yl]-amide |
| 71 | 2-[(3-chloro-benzoyl)-methyl-amino]-5,6,7,8-tetrahydro-imidazo[1,2-a]pyridine-3-carboxylic acid [2-(3-trifluoromethyl-phenyl)-ethyl]-amide |
| 72 | N-butyl-3-chloro-N-[3-(4-pyridin-2-yl-piperazine-1-carbonyl)-5,6,7,8-tetrahydro-imidazo[1,2-a]pyridin-2-yl]-benzamide |
| 73 | 2-[methyl-(naphthalene-1-carbonyl)-amino]-5,6,7,8-tetrahydro-imidazo[1,2-a]pyridine-3-carboxylic acid 3-methoxy-benzylamide |
| 74 | 2-[butyl-(3,4-difluoro-benzoyl)-amino]-5,6,7,8-tetrahydro-imidazo[1,2-a]pyridine-3-carboxylic acid 2,4-difluoro-benzylamide |
| 75 | 3-chloro-N-methyl-N-[3-(4-pyridin-2-yl-piperazine-1-carbonyl)-5,6,7,8-tetrahydro-imidazo[1,2-a]pyridin-2-yl]-benzamide |
| 76 | 2-[methyl-(naphthalene-1-carbonyl)-amino]-5,6,7,8-tetrahydro-imidazo[1,2-a]pyridine-3-carboxylic acid (1-biphenyl-4-ylmethyl-pyrrolidin-3-yl)-methyl-amide |
| 77 | 2-[butyl-(3-chloro-benzoyl)-amino]-5,6,7,8-tetrahydro-imidazo[1,2-a]pyridine-3-carboxylic acid (2,3-dihydro-benzo[1,4]dioxin-2-ylmethyl)-amide |
| 78 | 2-[butyl-(3-chloro-benzoyl)-amino]-5,6,7,8-tetrahydro-imidazo[1,2-a]pyridine-3-carboxylic acid [2-(1H-indol-3-yl)-ethyl]-methyl-amide |
| 79 | N-butyl-3-chloro-N-{3-[4-(3-trifluoromethyl-phenyl)-piperazine-1-carbonyl]-5,6,7,8-tetrahydro-imidazo[1,2-a]pyridin-2-yl}-benzamide |
| 80 | 2-(benzoyl-methyl-amino)-5,6,7,8-tetrahydro-imidazo[1,2-a]pyridine-3-carboxylic acid [2-(1H-indol-3-yl)-ethyl]-methyl-amide |
| 81 | 3-chloro-N-{3-[4-hydroxy-4-(3-trifluoromethyl-phenyl)-piperidine-1-carbonyl]-5,6,7,8-tetrahydro-imidazo[1,2-a]pyridin-2-yl}-N-methyl-benzamide |
| 82 | 2-[butyl-(3,4-difluoro-benzoyl)-amino]-5,6,7,8-tetrahydro-imidazo[1,2-a]pyridine-3-carboxylic acid (1-methoxymethyl-2-phenyl-ethyl)-amide |
| 83 | 2-[(3-chloro-benzoyl)-methyl-amino]-5,6,7,8-tetrahydro-imidazo[1,2-a]pyridine-3-carboxylic acid [1-(2,6-dichlor-benzyl)-pyrrolidin-3-yl]-amide |
| 84 | 2-[(3-chloro-benzoyl)-methyl-amino]-5,6,7,8-tetrahydro-imidazo[1,2-a]pyridin-3-carboxylic acid [1-(2-bromo-4,5-dimethoxy-benzyl)-pyrrolidin-3-yl]-amide |
| 85 | 2-(benzoyl-methyl-amino)-5,6,7,8-tetrahydro-imidazo[1,2-a]pyridine-3-carboxylic acid benzo[1,3]dioxol-5-ylamide |
| 86 | 2-[butyl-(3-chloro-benzoyl)-amino]-5,6,7,8-tetrahydro-imidazo[1,2-a]pyridine-3-carboxylic acid (1-methoxymethyl-2-phenyl-ethyl)-amide |
| 87 | 2-[butyl-(3-chloro-benzoyl)-amino]-5,6,7,8-tetrahydro-imidazo[1,2-a]pyridine-3-carboxylic acid [1-(2,6-dichloro-benzyl)-pyrrolidin-3-yl]-methyl-amide |
| 88 | 2-[butyl-(3,4-difluoro-benzoyl)-amino]-5,6,7,8-tetrahydro-imidazo[1,2-a]pyridine-3-carboxylic acid 2-trifluoromethoxy-benzylamide |
| 89 | N-butyl-3,4-difluoro-N-{3-[4-(isopropylcarbamoyl-methyl)-piperazine-1-carbonyl]-5,6,7,8-tetrahydro-imidazo[1,2-a]pyridin-2-yl}-benzamide |
| 90 | 2-[(3-chloro-benzoyl)-methyl-amino]-5,6,7,8-tetrahydro-imidazo[1,2-a]pyridine-3-carboxylic acid (1-methyl-3-phenyl-propyl)-amide |
| 91 | 2-({2-[butyl-(3-chloro-benzoyl)-amino]-5,6,7,8-tetrahydro-imidazo[1,2-a]pyridine-3-carbonyl}-amino)-3-methyl-benzyl butyrate |
| 92 | 2-[(3-chloro-benzoyl)-methyl-amino]-5,6,7,8-tetrahydro-imidazo[1,2-a]pyridine-3-carboxylic acid (thiophen-2-ylmethyl)-amide |
| 93 | 2-[butyl-(3,4-difluoro-benzoyl)-amino]-5,6,7,8-tetrahydro-imidazo[1,2-a]pyridine-3-carboxylic acid (2-methyl-cyclohexyl)-amide |
| 94 | 2-(benzoyl-methyl-amino)-5,6,7,8-tetrahydro-imidazo[1,2-a]pyridine-3-carboxylic acid benzyl-methyl-amide |
| 95 | 2-[butyl-(3-chloro-benzoyl)-amino]-5,6,7,8-tetrahydro-imidazo[1,2-a]pyridine-3-carboxylic acid [2-(2,6-dichlor-benzylsulphanyl)-ethyl]-amide |
| 96 | 2-[butyl-(3,4-difluoro-benzoyl)-amino]-5,6,7,8-tetrahydro-imidazo[1,2-a]pyridine-3-carboxylic acid (2,3-dihydro-benzo[1,4]dioxin-2-ylmethyl)-amide |
| 97 | 2-[(3-chloro-benzoyl)-methyl-amino]-5,6,7,8-tetrahydro-imidazo[1,2-a]pyridine-3-carboxylic acid 4-trifluoromethyl-benzylamide |
| 98 | N-[3-(4-benzyl-piperidine-1-carbonyl)-5,6,7,8-tetrahydro-imidazo[1,2-a]pyridin-2-yl]-N-methyl-benzamide |

-continued

| Example | Name |
|---|---|
| 99 | 2-[methyl-(naphthalene-1-carbonyl)-amino]-5,6,7,8-tetrahydro-imidazo[1,2-a]pyridine-3-carboxylic acid 2-trifluoromethoxy-benzylamide |
| 100 | 3-chloro-N-{3-[4-(2,5-dimethyl-phenyl)-piperazine-1-carbonyl]-5,6,7,8-tetrahydro-imidazo[1,2-a]pyridin-2-yl}-N-methyl-benzamide |
| 101 | 2-(benzoyl-methyl-amino)-5,6,7,8-tetrahydro-imidazo[1,2-a]pyridine-3-carboxylic acid [1-(2,6-dichloro-benzyl)-pyrrolidin-3-yl]-amide |
| 102 | 2-[butyl-(3,4-difluoro-benzoyl)-amino]-5,6,7,8-tetrahydro-imidazo[1,2-a]pyridine-3-carboxylic acid 2-chloro-6-methyl-benzylamide |
| 103 | N-butyl-3-chloro-N-[3-(3,5-dimethyl-piperidine-1-carbonyl)-5,6,7,8-tetrahydro-imidazo[1,2-a]pyridin-2-yl]-benzamide |
| 104 | 2-({2-[(3-chloro-benzoyl)-methyl-amino]-5,6,7,8-tetrahydro-imidazo[1,2-a]pyridine-3-carbonyl}-amino)-3,3-dimethyl-butyric acid tert-butyl ester |
| 105 | 2-[methyl-(naphthalene-1-carbonyl)-amino]-5,6,7,8-tetrahydro-imidazo[1,2-a]pyridine-3-carboxylic acid (1-cyclohexyl-ethyl)-amide |
| 106 | 3-chloro-N-methyl-N-[3-(4-phenethyl-piperazine-1-carbonyl)-5,6,7,8-tetrahydro-imidazo[1,2-a]pyridin-2-yl]-benzamide |
| 107 | 2-[butyl-(3-chloro-benzoyl)-amino]-5,6,7,8-tetrahydro-imidazo[1,2-a]pyridine-3-carboxylic acid (2-phenoxy-ethyl)-amide |
| 108 | naphthalene-1-carboxylic acid [3-(4-benzofuran-2-ylmethyl-piperazine-1-carbonyl)-5,6,7,8-tetrahydro-imidazo[1,2-a]pyridin-2-yl]-methyl-amide |
| 109 | N-[3-([1,4']bipiperidinyl-1'-carbonyl)-5,6,7,8-tetrahydro-imidazo[1,2-a]pyridin-2-yl]-N-butyl-3-chloro-benzamide |
| 110 | N-butyl-3-chloro-N-[3-(8-fluoro-1,3,4,5-tetrahydro-pyrido[4,3-b]indole-2-carbonyl)-5,6,7,8-tetrahydro-imidazo[1,2-a]pyridin-2-yl]-benzamide |
| 111 | 2-[methyl-(naphthalene-1-carbonyl)-amino]-5,6,7,8-tetrahydro-imidazo[1,2-a]pyridine-3-carboxylic acid 4-dimethylamino-benzylamide |
| 112 | 2-[methyl-(naphthalene-1-carbonyl)-amino]-5,6,7,8-tetrahydro-imidazo[1,2-a]pyridine-3-carboxylic acid (1-methyl-3-phenyl-propyl)-amide |
| 113 | 2-[butyl-(3-chloro-benzoyl)-amino]-5,6,7,8-tetrahydro-imidazo[1,2-a]pyridine-3-carboxylic acid 3-methyl-benzylamide |
| 114 | 2-[(3-chloro-benzoyl)-methyl-amino]-5,6,7,8-tetrahydro-imidazo[1,2-a]pyridine-3-carboxylic acid (2,3-dihydro-benzo[1,4]dioxin-6-yl)-amide |
| 115 | naphthalene-1-carboxylic acid methyl-[3-(4-quinolin-2-ylmethyl-piperazine-1-carbonyl)-5,6,7,8-tetrahydro-imidazo[1,2-a]pyridin-2-yl]-amide |
| 116 | 2-[butyl-(3,4-difluoro-benzoyl)-amino]-5,6,7,8-tetrahydro-imidazo[1,2-a]pyridine-3-carboxylic acid (2-cyano-ethyl)-methyl-amide |
| 117 | 2-(methyl-phenylacetyl-amino)-5,6,7,8-tetrahydro-imidazo[1,2-a]pyridine-3-carboxylic acid (2-p-tolyl-ethyl)-amide |
| 118 | 2-[butyl-(3,4-difluoro-benzoyl)-amino]-5,6,7,8-tetrahydro-imidazo[1,2-a]pyridine-3-carboxylic acid [1-(4-fluoro-phenyl)-ethyl]-amide |
| 119 | N-butyl-N-{3-[4-(5-chloro-2-methyl-phenyl)-piperazine-1-carbonyl]-5,6,7,8-tetrahydro-imidazo[1,2-a]pyridin-2-yl}-3,4-difluoro-benzamide |
| 120 | 2-[butyl-(3-chloro-benzoyl)-amino]-5,6,7,8-tetrahydro-imidazo[1,2-a]pyridine-3-carboxylic acid cyclohexylamide |
| 121 | 2-[(3-chloro-benzoyl)-methyl-amino]-5,6,7,8-tetrahydro-imidazo[1,2-a]pyridine-3-carboxylic acid (benzo[1,3]dioxol-5-ylmethyl)-amide |
| 122 | 2-[butyl-(3,4-difluoro-benzoyl)-amino]-5,6,7,8-tetrahydro-imidazo[1,2-a]pyridine-3-carboxylic acid 3-methoxy-benzylamide |
| 123 | 3-tert-butoxy-2-({2-[(3-chloro-benzoyl)-methyl-amino]-5,6,7,8-tetrahydro-imidazo[1,2-a]pyridine-3-carbonyl}-amino)-methyl butyrate |
| 124 | 2-[butyl-(3-chloro-benzoyl)-amino]-5,6,7,8-tetrahydro-imidazo[1,2-a]pyridine-3-carboxylic acid (2-benzyloxy-cyclohexyl)-amide |
| 125 | N-{3-[4-(4-fluoro-phenyl)-piperazine-1-carbonyl]-5,6,7,8-tetrahydro-imidazo[1,2-a]pyridin-2-yl}-N-methyl-benzamide |
| 126 | 2-(benzoyl-methyl-amino)-5,6,7,8-tetrahydro-imidazo[1,2-a]pyridine-3-carboxylic acid (naphthalen-2-ylcarbamoylmethyl)-amide |
| 127 | 2-[butyl-(3-chloro-benzoyl)-amino]-5,6,7,8-tetrahydro-imidazo[1,2-a]pyridine-3-carboxylic acid 4-trifluoromethoxy-benzylamide |
| 128 | 2-[(3-chloro-benzoyl)-methyl-amino]-5,6,7,8-tetrahydro-imidazo[1,2-a]pyridine-3-carboxylic acid (3,3-diphenyl-propyl)-amide |
| 129 | 2-[(3-chloro-benzoyl)-methyl-amino]-5,6,7,8-tetrahydro-imidazo[1,2-a]pyridine-3-carboxylic acid (4-benzyloxy-phenyl)-amide |
| 130 | N-{3-[4-(5-bromo-2-ethoxy-benzyl)-piperazine-1-carbonyl]-5,6,7,8-tetrahydro-imidazo[1,2-a]pyridin-2-yl}-N-methyl-2-phenyl-acetamide |
| 131 | N-[3-(3,4-dihydro-1H-isoquinoline-2-carbonyl)-5,6,7,8-tetrahydro-imidazo[1,2-a]pyridin-2-yl]-N-methyl-benzamide |
| 132 | 2-[butyl-(3-chloro-benzoyl)-amino]-5,6,7,8-tetrahydro-imidazo[1,2-a]pyridine-3-carboxylic acid (1-phenyl-propyl)-amide |
| 133 | 2-[butyl-(3-chloro-benzoyl)-amino]-5,6,7,8-tetrahydro-imidazo[1,2-a]pyridine-3-carboxylic acid 2,3-dimethyl-benzylamide |

-continued

| Example | Name |
|---|---|
| 134 | 2-[butyl-(3-chloro-benzoyl)-amino]-5,6,7,8-tetrahydro-imidazo[1,2-a]pyridine-3-carboxylic acid [2-(4-phenoxy-phenyl)-ethyl]-amide |
| 135 | N-{3-[4-(4-ethoxy-phenyl)-piperazine-1-carbonyl]-5,6,7,8-tetrahydro-imidazo[1,2-a]pyridin-2-yl}-N-methyl-2-phenyl-acetamide |
| 136 | naphthalene-1-carboxylic acid {3-[4-(2-ethyl-phenyl)-piperazine-1-carbonyl]-5,6,7,8-tetrahydro-imidazo[1,2-a]pyridin-2-yl}-methyl-amide |
| 137 | N-[3-(4-benzo[1,3]dioxol-5-ylmethyl-piperazine-1-carbonyl)-5,6,7,8-tetrahydro-imidazo[1,2-a]pyridin-2-yl]-N-butyl-3,4-difluor-benzamide |
| 138 | N-butyl-N-{3-[4-(2,5-dimethyl-phenyl)-piperazine-1-carbonyl]-5,6,7,8-tetrahydro-imidazo[1,2-a]pyridin-2-yl}-3,4-difluoro-benzamide |
| 139 | 2-[methyl-(naphthalene-1-carbonyl)-amino]-5,6,7,8-tetrahydro-imidazo[1,2-a]pyridine-3-carboxylic acid [(4-chlor-phenyl)-phenyl-methyl]-amide |
| 140 | N-butyl-3-chloro-N-{3-[4-(4-chloro-benzyl)-piperazine-1-carbonyl]-5,6,7,8-tetrahydro-imidazo[1,2-a]pyridin-2-yl}-benzamide |
| 141 | 2-[butyl-(3-chloro-benzoyl)-amino]-5,6,7,8-tetrahydro-imidazo[1,2-a]pyridine-3-carboxylic acid (1-naphthalen-2-yl-ethyl)-amide |
| 142 | 2-(methyl-phenylacetyl-amino)-5,6,7,8-tetrahydro-imidazo[1,2-a]pyridine-3-carboxylic acid 2-fluoro-benzylamide |
| 143 | N-[3-(1,4-dioxa-8-aza-spiro[4.5]decane-8-carbonyl)-5,6,7,8-tetrahydro-imidazo[1,2-a]pyridin-2-yl]-N-methyl-2-phenyl-acetamide |
| 144 | naphthalene-1-carboxylic acid methyl-[3-(1,3,4,9-tetrahydro-b-carboline-2-carbonyl)-5,6,7,8-tetrahydro-imidazo[1,2-a]pyridin-2-yl]-amide |
| 145 | 2-[butyl-(3-chloro-benzoyl)-amino]-5,6,7,8-tetrahydro-imidazo[1,2-a]pyridine-3-carboxylic acid (1-methyl-3-phenyl-propyl)-amide |
| 146 | 3-chloro-N-methyl-N-{3-[4-(2,4,6-trimethoxy-benzyl)-piperazine-1-carbonyl]-5,6,7,8-tetrahydro-imidazo[1,2-a]pyridin-2-yl}-benzamide |
| 147 | 2-[butyl-(3-chloro-benzoyl)-amino]-5,6,7,8-tetrahydro-imidazo[1,2-a]pyridine-3-carboxylic acid benzhydryl-amide |
| 148 | naphthalene-1-carboxylic acid {3-[4-(2-chloro-phenyl)-piperazine-1-carbonyl]-5,6,7,8-tetrahydro-imidazo[1,2-a]pyridin-2-yl}-methyl-amide |
| 149 | 2-[butyl-(3-chloro-benzoyl)-amino]-5,6,7,8-tetrahydro-imidazo[1,2-a]pyridine-3-carboxylic acid (thiophen-2-ylmethyl)-amide |
| 150 | N-butyl-N-{3-[4-(4-chlorobenzyl)-piperazine-1-carbonyl]-5,6,7,8-tetrahydro-imidazo[1,2-a]pyridin-2-yl}-3,4-difluoro-benzamide |
| 151 | 2-(benzoyl-methyl-amino)-5,6,7,8-tetrahydro-imidazo[1,2-a]pyridine-3-carboxylic acid (3-phenyl-propyl)-amide |
| 152 | 2-[butyl-(3-chloro-benzoyl)-amino]-5,6,7,8-tetrahydro-imidazo[1,2-a]pyridine-3-carboxylic acid (4-tert-butyl-phenyl)-amide |
| 153 | 2-[butyl-(3-chloro-benzoyl)-amino]-5,6,7,8-tetrahydro-imidazo[1,2-a]pyridine-3-carboxylic acid (4-ethyl-phenyl)-amide |
| 154 | 2-[methyl-(naphthalene-1-carbonyl)-amino]-5,6,7,8-tetrahydro-imidazo[1,2-a]pyridine-3-carboxylic acid cyclohexylamide |
| 155 | 2-[methyl-(naphthalene-1-carbonyl)-amino]-5,6,7,8-tetrahydro-imidazo[1,2-a]pyridine-3-carboxylic acid [3-(methyl-phenyl-amino)-propyl]-amide |
| 156 | 2-(methyl-phenylacetyl-amino)-5,6,7,8-tetrahydro-imidazo[1,2-a]pyridine-3-carboxylic acid [2-(3-trifluoromethyl-phenyl)-ethyl]-amide |
| 157 | 2-(benzoyl-methyl-amino)-5,6,7,8-tetrahydro-imidazo[1,2-a]pyridine-3-carboxylic acid 4-chloro-benzylamide |
| 158 | 2-[butyl-(3-chloro-benzoyl)-amino]-5,6,7,8-tetrahydro-imidazo[1,2-a]pyridine-3-carboxylic acid 3-fluoro-benzylamide |
| 159 | 2-(methyl-phenylacetyl-amino)-5,6,7,8-tetrahydro-imidazo[1,2-a]pyridine-3-carboxylic acid p-tolylamide |
| 160 | 2-(benzoyl-methyl-amino)-5,6,7,8-tetrahydro-imidazo[1,2-a]pyridine-3-carboxylic acid (2-phenoxy-ethyl)-amide |
| 161 | 2-[butyl-(3,4-difluoro-benzoyl)-amino]-5,6,7,8-tetrahydro-imidazo[1,2-a]pyridine-3-carboxylic acid (2-benzyloxy-cyclohexyl)-amide |
| 162 | naphthalene-1-carboxylic acid {3-[4-(4-fluoro-phenyl)-piperazine-1-carbonyl]-5,6,7,8-tetrahydro-imidazo[1,2-a]pyridin-2-yl}-methyl-amide |
| 163 | 2-[methyl-(naphthalene-1-carbonyl)-amino]-5,6,7,8-tetrahydro-imidazo[1,2-a]pyridine-3-carboxylic acid [2-(4-chlor-phenyl)-propyl]-amide |
| 164 | N-butyl-3,4-difluoro-N-[3-(thiomorpholine-4-carbonyl)-5,6,7,8-tetrahydro-imidazo[1,2-a]pyridin-2-yl]-benzamide |
| 165 | 2-[(3-chloro-benzoyl)-methyl-amino]-5,6,7,8-tetrahydro-imidazo[1,2-a]pyridine-3-carboxylic acid (1-adamantan-1-yl-ethyl)-amide |
| 166 | 2-(benzoyl-methyl-amino)-5,6,7,8-tetrahydro-imidazo[1,2-a]pyridine-3-carboxylic acid [(4-chloro-phenyl)-phenyl-methyl]-amide |
| 167 | N-methyl-N-{3-[4-(4-trifluoromethyl-phenyl)-piperazine-1-carbonyl]-5,6,7,8-tetrahydro-imidazo[1,2-a]pyridin-2-yl}-benzamide |

| Example | Name |
|---|---|
| 168 | 2-(methyl-phenylacetyl-amino)-5,6,7,8-tetrahydro-imidazo[1,2-a]pyridine-3-carboxylic acid (1-biphenyl-4-ylmethyl-pyrrolidin-3-yl)-methyl-amide |
| 169 | N-[3-(4-benzoyl-piperidine-1-carbonyl)-5,6,7,8-tetrahydro-imidazo[1,2-a]pyridin-2-yl]-3-chloro-N-methyl-benzamide |
| 170 | 2-[methyl-(naphthalene-1-carbonyl)-amino]-5,6,7,8-tetrahydro-imidazo[1,2-a]pyridine-3-carboxylic acid (4-tert-butyl-phenyl)-amide |
| 171 | 2-[butyl-(3,4-difluoro-benzoyl)-amino]-5,6,7,8-tetrahydro-imidazo[1,2-a]pyridine-3-carboxylic acid (3,3-dimethyl-butyl)-amide |
| 172 | 2-[butyl-(3-chloro-benzoyl)-amino]-5,6,7,8-tetrahydro-imidazo[1,2-a]pyridine-3-carboxylic acid [1-(2-bromo-4,5-dimethoxy-benzyl)-pyrrolidin-3-yl]-amide |
| 173 | naphthalene-1-carboxylic acid methyl-{3-[4-(3-phenyl-allyl)-piperazine-1-carbonyl]-5,6,7,8-tetrahydro-imidazo[1,2-a]pyridin-2-yl}-amide |
| 174 | naphthalene-1-carboxylic acid methyl-[3-(4-phenethyl-piperazine-1-carbonyl)-5,6,7,8-tetrahydro-imidazo[1,2-a]pyridin-2-yl]-amide |
| 175 | N-butyl-3-chloro-N-{3-[4-hydroxy-4-(3-trifluoromethyl-phenyl)-piperidine-1-carbonyl]-5,6,7,8-tetrahydro-imidazo[1,2-a]pyridin-2-yl}-benzamide |
| 176 | N-methyl-2-phenyl-N-{3-[4-(3-phenyl-propyl)-piperazine-1-carbonyl]-5,6,7,8-tetrahydro-imidazo[1,2-a]pyridin-2-yl}-acetamide |
| 177 | 2-(benzoyl-methyl-amino)-5,6,7,8-tetrahydro-imidazo[1,2-a]pyridine-3-carboxylic acid 3-fluoro-benzylamide |
| 178 | N-butyl-N-{3-[4-(2-chloro-phenyl)-piperazine-1-carbonyl]-5,6,7,8-tetrahydro-imidazo[1,2-a]pyridin-2-yl}-3,4-difluoro-benzamide |
| 179 | 2-[methyl-(naphthalene-1-carbonyl)-amino]-5,6,7,8-tetrahydro-imidazo[1,2-a]pyridine-3-carboxylic acid benzo[1,3]dioxol-5-ylamide |
| 180 | 2-[butyl-(3,4-difluoro-benzoyl)-amino]-5,6,7,8-tetrahydro-imidazo[1,2-a]pyridine-3-carboxylic acid (3,3-diphenyl-propyl)-amide |
| 181 | 2-[butyl-(3-chloro-benzoyl)-amino]-5,6,7,8-tetrahydro-imidazo[1,2-a]pyridine-3-carboxylic acid (2,3-dihydro-benzo[1,4]dioxin-6-yl)-amide |
| 182 | 2-(benzoyl-methyl-amino)-5,6,7,8-tetrahydro-imidazo[1,2-a]pyridine-3-carboxylic acid [2-(3,4-dimethoxy-phenyl)-ethyl]-amide |
| 183 | naphthalene-1-carboxylic acid [3-(4-benzoyl-piperidine-1-carbonyl)-5,6,7,8-tetrahydro-imidazo[1,2-a]pyridin-2-yl]-methyl-amide |
| 184 | 4-methyl-2-({2-[methyl-(naphthalene-1-carbonyl)-amino]-5,6,7,8-tetrahydro-imidazo[1,2-a]pyridine-3-carbonyl}-amino)-valeric acid tert-benzyl ester |
| 185 | 2-[methyl-(naphthalene-1-carbonyl)-amino]-5,6,7,8-tetrahydro-imidazo[1,2-a]pyridine-3-carboxylic acid (4-phenoxy-phenyl)-amide |
| 186 | N-methyl-2-phenyl-N-[3-(4-phenyl-piperazine-1-carbonyl)-5,6,7,8-tetrahydro-imidazo[1,2-a]pyridin-2-yl]-acetamide |
| 187 | N-butyl-3,4-difluoro-N-{3-[4-(5-trifluoromethyl-pyridin-2-yl)-piperazine-1-carbonyl]-5,6,7,8-tetrahydro-imidazo[1,2-a]pyridin-2-yl}-benzamide |
| 188 | 2-(benzoyl-methyl-amino)-5,6,7,8-tetrahydro-imidazo[1,2-a]pyridine-3-carboxylic acid 2,4-dichloro-6-methyl-benzylamide |
| 189 | [4-({2-[butyl-(3-chloro-benzoyl)-amino]-5,6,7,8-tetrahydro-imidazo[1,2-a]pyridine-3-carbonyl}-amino)-phenyl]-carbamic acid tert-butyl ester |
| 190 | N-methyl-2-phenyl-N-[3-(2-pyrrolidin-1-ylmethyl-pyrrolidine-1-carbonyl)-5,6,7,8-tetrahydro-imidazo[1,2-a]pyridin-2-yl]-acetamide |
| 191 | 4-[2-(methyl-phenylacetyl-amino)-5,6,7,8-tetrahydro-imidazo[1,2-a]pyridine-3-carbonyl]-piperazine-1-carboxylic acid tert-butyl ester |

Pharmacological Data

The affinity of the substituted 5,6,7,8-tetrahydro-imidazo[1,2-a]pyridin-2-ylamine compounds according to the invention for the batrachotoxin-(BTX) binding site and the μ-opioid receptor, and also the agonistic and antagonistic activity of the substituted 5,6,7,8-tetrahydro-imidazo[1,2-a]pyridin-2-ylamine compounds according to the invention on the vanilloid receptor 1 (VR1/TRPV1-receptor) have been determined in the manner described hereinbefore.

The investigated 5,6,7,8-tetrahydro-imidazo[1,2-a]pyridin-2-ylamine compounds according to the invention exhibit excellent activity on the vanilloid receptor 1 (VR1/TRPV1-receptor).

In addition, these compounds according to the invention also exhibit excellent affinities for the batrachotoxin-(BTX) binding site of the sodium channel and the μ-opioid receptor.

| Compound according to Example | VR1 (rat) (% stimulation in comparison with 10 μM CP) | VR1 (rat) (% inhibition in comparison with 10 μM CP) | BTX inhibition (rat) (% inhibition) | μ-opioid receptor (man) (% inhibition) |
|---|---|---|---|---|
| 2 | | | 59 | |
| 3 | | | 34 | |
| 4 | | | | |
| 5 | | | | |
| 9 | | | 36 | |
| 11 | | | | |
| 12 | 48 | 73 | | |
| 14 | | | 41 | |

-continued

| Compound according to Example | VR1 (rat) (% stimulation in comparison with 10 μM CP) | VR1 (rat) (% inhibition in comparison with 10 μM CP) | BTX inhibition (rat) (% inhibition) | μ-opioid receptor (man) (% inhibition) |
|---|---|---|---|---|
| 15 | | | 68 | 35 |
| 16 | 90 | 100 | 47 | |
| 17 | | | | |
| 19 | 49 | 87 | | |
| 20 | | | | |
| 21 | | | | |
| 22 | | | | |
| 26 | | | 93 | |
| 27 | | | 35 | |
| 28 | | 43 | 42 | |
| 30 | | | 85 | |
| 31 | | | 70 | |
| 33 | | | 49 | |
| 34 | | | 83 | |
| 38 | | 40 | | |
| 39 | 38 | 99 | 47 | |
| 40 | | | | |
| 42 | 43 | 90 | | |
| 43 | 59 | 104 | 40 | |
| 45 | | | 41 | |
| 46 | | | 67 | |
| 47 | 60 | 81 | 44 | |
| 48 | | | 89 | |
| 49 | | | 37 | |
| 51 | 47 | 96 | 35 | |
| 52 | 53 | 101 | 45 | |
| 53 | | | 64 | |
| 56 | | 53 | 65 | |
| 57 | 40 | 103 | 31 | |
| 58 | | | 50 | |
| 59 | | | 95 | |
| 61 | | | 38 | |
| 65 | | 30 | | |
| 66 | | | | |
| 67 | | 52 | 51 | |
| 68 | | | 87 | |
| 69 | | 43 | 48 | |
| 71 | | | 36 | |
| 72 | | | 39 | |
| 73 | | 40 | | |
| 74 | 32 | 94 | | |
| 76 | | | 95 | |
| 77 | | 63 | 56 | |
| 79 | | 62 | 83 | |
| 81 | | | 33 | |
| 82 | | 77 | | |
| 83 | | | 80 | |
| 84 | | | 87 | |
| 85 | | | 30 | |
| 86 | 34 | 114 | 42 | |
| 87 | | | 93 | |
| 88 | 44 | 132 | 31 | |
| 91 | | 121 | 48 | |
| 93 | 51 | 171 | | |
| 95 | | 52 | 68 | 53 |
| 96 | | | 33 | |
| 99 | | | 33 | |
| 100 | | | 74 | |
| 101 | | | 54 | |
| 102 | 66 | 97 | | |
| 104 | | 45 | | |
| 105 | | 32 | | |
| 106 | | | 40 | 30 |
| 107 | | | 39 | |
| 108 | | | 41 | |
| 109 | 68 | 90 | | |
| 112 | | | | 51 |
| 113 | 39 | 89 | 31 | |
| 118 | | 66 | | |
| 119 | | | 83 | |
| 120 | 67 | 97 | 61 | |
| 122 | | 62 | | |
| 123 | 36 | 98 | | |
| 124 | 37 | 93 | 48 | |
| 127 | | | 60 | |
| 128 | | 39 | 85 | |
| 129 | | | 76 | |
| 130 | | | 67 | |
| 132 | 67 | 99 | | |
| 133 | | 64 | 34 | |
| 134 | | | 93 | |
| 136 | | | 54 | |
| 137 | | | 72 | |
| 138 | | | 80 | |
| 139 | | 43 | 73 | |
| 140 | | | 81 | |
| 141 | | | 41 | |
| 144 | | | 31 | |
| 145 | 30 | 82 | 67 | |
| 146 | | | 70 | |
| 147 | | 53 | 56 | |
| 148 | | | 35 | |
| 149 | 43 | 72 | | |
| 150 | | | 69 | |
| 152 | | | 92 | |
| 154 | | | 92 | |
| 156 | | 34 | 40 | |
| 157 | | | 43 | |
| 158 | 33 | 53 | 33 | |
| 159 | | | 37 | |
| 161 | 32 | 91 | 49 | |
| 163 | 83 | 53 | 40 | |
| 165 | | 47 | 39 | |
| 166 | | | 72 | |
| 167 | | | 44 | |
| 168 | | | 92 | |
| 170 | | | 80 | |
| 171 | 46 | 104 | 47 | |
| 172 | | | 96 | |
| 173 | | | 74 | |
| 174 | | | 47 | |
| 175 | | | 65 | |
| 176 | | | 71 | |
| 178 | | | 79 | |
| 179 | | | | |
| 180 | 56 | 102 | 62 | 47 |
| 181 | | | 82 | 58 |
| 184 | 35 | 41 | | |
| 185 | | 56 | 74 | |
| 186 | | | | 48 |
| 187 | | 37 | 41 | |
| 188 | | | | 59 |
| 189 | | | 93 | |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted 5,6,7,8-tetrahydro-imidazo[1,2-a]pyridin-2-ylamine compound corresponding to formula I,

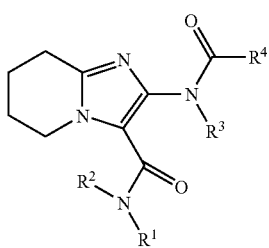

wherein

R¹ and R², independently of one another, each represent hydrogen;
—C(=O)—OR⁵;
—(CHR⁶)—(CH₂)$_m$—C(=O)—OR⁷ in which m=0, 1, 2, 3, 4 or 5;
—C(=O)—R⁸;
—(CH₂)$_n$—C(=O)—R⁹ in which n=1, 2, 3, 4 or 5;
—C(=O)—NH—R¹⁰;
—(CH₂)$_o$—C(=O)—NHR¹¹ in which o=0, 1, 2, 3, 4 or 5;
—C(=O)—NR¹²R¹³;
—(CH₂)$_p$—C(=O)—NR¹⁴R¹⁵ in which p=1, 2, 3, 4 or 5;
—(CHR¹⁶)—X$_q$—(CHR¹⁷)$_r$—Y$_s$—(CHR¹⁸)$_t$—Z$_u$—R¹⁹ in which q=0 or 1, r=0 or 1, s=0 or 1, t=0 or 1, u=0 or 1 and in which X, Y and Z, independently of one another, each represent O, S, NH, N(CH₃), N(C₂H₅) or N[CH(CH₃)₂];
or
a linear or branched, saturated or unsaturated, optionally substituted C$_{1-10}$ aliphatic group;
a saturated or unsaturated, optionally substituted 3-, 4-, 5-, 6-, 7-, 8- or 9-membered cycloaliphatic group which can be bridged with a linear or branched, optionally substituted C$_{1-5}$ alkylene group and/or condensed with a saturated, unsaturated or aromatic, optionally substituted monocyclic or polycyclic ring system; or
an optionally substituted 5- to 14-membered aryl or heteroaryl group which may be condensed with a saturated or unsaturated, optionally substituted monocyclic or polycyclic ring system; or R¹ and R², together with the nitrogen atom which binds them as the ring member, form a saturated or unsaturated, optionally substituted 4-, 5-, 6-, 7-, 8- or 9-membered heterocycloaliphatic group, which may be condensed with a saturated, unsaturated or aromatic, optionally substituted monocyclic or polycyclic ring system and/or, together with a saturated or unsaturated, optionally substituted 5-, 6- or 7-membered cycloaliphatic group, can form an optionally substituted spiro compound via a common ring atom,
in which the heterocycloaliphatic group and optionally the cycloaliphatic group of the spiro compound may each be substituted with 1, 2, 3, 4 or 5 substituents selected independently of one another from the group consisting of R²⁰, —(CHR²¹)—(CH₂)$_v$—(CH₂)$_w$—R²² in which v=0 or 1 and w=0 or 1, —CH=CH—R²³, —(CH₂)$_x$—C(=O)—OR²⁴ in which x=0, 1, 2, 3, 4 or 5; —(CH₂)$_y$—C(=O)—R²⁵ in which y=0, 1, 2, 3, 4 or 5; —(CH₂)$_z$—C(=O)—NHR²⁶ in which z=0, 1, 2, 3, 4 or 5; —(CH₂)$_{aa}$—C(=O)—NR²⁷R²⁸ in which aa=0, 1, 2, 3, 4 or 5; F; Cl; Br; —CN; —CF₃; —NO₂; oxo (=O); thioxo (=S); —C$_{1-5}$alkyl; —OH; —O—C$_{1-5}$ alkyl; —SH; —S—C$_{1-5}$ alkyl; —NH₂; NH—C$_{1-5}$ alkyl and —N(C$_{1-5}$ alkyl)₂ and/or may each have a further 1, 2, 3, 4 or 5 heteroatom(s) as the ring member(s) selected independently of one another from the group consisting of oxygen, nitrogen and sulphur;

R³ represents a hydrogen group;
a linear or branched, saturated or unsaturated, optionally substituted C$_{1-10}$ aliphatic group,
a saturated or unsaturated, optionally substituted 3-, 4-, 5-, 6-, 7-, 8- or 9-membered cycloaliphatic group which may be bound by a linear or branched, optionally substituted C$_{1-5}$ alkylene, C$_{2-5}$ alkenylene or C$_{2-5}$ alkynylene group, or
an optionally substituted 5- to 14-membered aryl or heteroaryl group which may be condensed with a saturated or unsaturated, optionally substituted monocyclic or polycyclic ring system and/or may be bound by a linear or branched, optionally substituted C$_{1-5}$ alkylene, C$_{2-5}$ alkenylene or C$_{2-5}$ alkynylene group;

R⁴ represents a linear or branched, saturated or unsaturated, optionally substituted C$_{1-10}$ aliphatic group,
a saturated or unsaturated, optionally substituted 3-, 4-, 5-, 6-, 7-, 8- or 9-membered cycloaliphatic group which may be bound by a linear or branched, optionally substituted C$_{1-5}$ alkylene, C$_{2-5}$ alkenylene or C$_{2-5}$ alkynylene group, or
an optionally substituted 5- to 14-membered aryl or heteroaryl group which may be condensed with a saturated or unsaturated, optionally substituted monocyclic or polycyclic ring system and/or may be bound by a linear or branched, optionally substituted C$_{1-5}$ alkylene, C$_{2-5}$ alkenylene or C$_{2-5}$ alkynylene group;

R⁵, R⁷, R⁸, R⁹, R¹⁰, R¹¹, R¹², R¹³, R¹⁴, R¹⁵, R²⁴, R²⁵, R²⁶, R²⁷ and R²⁸, independently of one another, each represent
a linear or branched, saturated or unsaturated, optionally substituted C$_{1-10}$ aliphatic group,
an unsaturated or saturated, optionally substituted 3-, 4-, 5-, 6-, 7-, 8- or 9-membered cycloaliphatic group which may be condensed with a saturated, unsaturated or aromatic, optionally substituted monocyclic or polycyclic ring system and/or may be bound by a linear or branched, optionally substituted C$_{1-5}$ alkylene, C$_{2-5}$ alkenylene or C$_{2-5}$ alkynylene group, or
an optionally substituted 5- to 14-membered aryl or heteroaryl group which may be condensed with a saturated or unsaturated, optionally substituted monocyclic or polycyclic ring system and/or may be bound by a linear or branched, optionally substituted C$_{1-5}$ alkylene, C$_{2-5}$ alkenylene or C$_{2-5}$ alkynylene group;

R⁶ represents hydrogen;
a linear or branched, saturated or unsaturated, optionally substituted C$_{1-10}$ aliphatic group, which may optionally have 1, 2, 3, 4 or 5 heteroatom(s) as the chain link(s) selected from the group consisting of oxygen, sulphur and nitrogen; or
an optionally substituted 5- to 14-membered aryl or heteroaryl group which may be condensed with a saturated or unsaturated, optionally substituted monocyclic or polycyclic ring system and/or may be bound by a linear or branched, optionally substituted $C_{1-5}$ alkylene, $C_{2-5}$ alkenylene or $C_{2-5}$ alkynylene group;

$R^{16}$, $R^{17}$ and $R^{18}$, independently of one another, each represent hydrogen;
a linear or branched, saturated or unsaturated, optionally substituted $C_{1-10}$ aliphatic group, which may have 1, 2, 3, 4 or 5 heteroatom(s) as the chain link(s) selected independently of one another from the group consisting of oxygen, sulphur and nitrogen; or
an optionally substituted 5- to 14-membered aryl or heteroaryl group which may be condensed with a saturated or unsaturated, optionally substituted monocyclic or polycyclic ring system;

$R^{19}$ represents an unsaturated or saturated, optionally substituted 3-, 4-, 5-, 6-, 7-, 8- or 9-membered cycloaliphatic group which can be bridged with 1, 2, 3, 4 or 5 linear or branched, optionally substituted $C_{1-5}$ alkylene groups and/or condensed with a saturated, unsaturated or aromatic, optionally substituted monocyclic or polycyclic ring system; or
an optionally substituted 5- to 14-membered aryl or heteroaryl group which may be condensed with a saturated or unsaturated, optionally substituted monocyclic or polycyclic ring system;

$R^{20}$ represents a linear or branched, saturated or unsaturated, optionally substituted $C_{1-10}$ aliphatic group;
an unsaturated or saturated, optionally substituted 3-, 4-, 5-, 6-, 7-, 8- or 9-membered cycloaliphatic group; or
an optionally substituted 5- to 14-membered aryl or heteroaryl group which may be condensed with a saturated or unsaturated, optionally substituted monocyclic or polycyclic ring system;

$R^{21}$ represents hydrogen;
a linear or branched, saturated or unsaturated, optionally substituted $C_{1-10}$ aliphatic group;
an unsaturated or saturated, optionally substituted 3-, 4-, 5-, 6-, 7-, 8- or 9-membered cycloaliphatic group; or
an optionally substituted 5- to 14-membered aryl or heteroaryl group which may be condensed with a saturated or unsaturated, optionally substituted monocyclic or polycyclic ring system; and $R^{22}$ and $R^{23}$, independently of one another, each represent an unsaturated or saturated, optionally substituted 3-, 4-, 5-, 6-, 7-, 8- or 9-membered cycloaliphatic group; or
an optionally substituted 5- to 14-membered aryl or heteroaryl group which may be condensed with a saturated or unsaturated, optionally substituted monocyclic or polycyclic ring system;

in which
the aforementioned $C_{1-10}$ aliphatic groups may optionally each be substituted with 1, 2, 3, 4 or 5 substituents selected independently of one another from the group consisting of F, Cl, Br, I, —CN, —NO$_2$, —OH, —SH and —NH$_2$;

the aforementioned cycloaliphatic groups may optionally each be substituted with 1, 2, 3, 4 or 5 substituents selected independently of one another from the group consisting of oxo (=O), thioxo (=S), F, Cl, Br, I, —CN, —CF$_3$, —SF$_5$, —OH, —O—$C_{1-5}$ alkyl, —NH$_2$, —NO$_2$, —O—CF$_3$, —S—CF$_3$, —SH, —S—$C_{1-5}$ alkyl, —$C_{1-5}$ alkyl, —C(=O)—OH, —C(=O)—O—$C_{1-5}$ alkyl, —NH—$C_{1-5}$ alkyl, —N($C_{1-5}$ alkyl)$_2$, —(CH$_2$)-benzo[b]furanyl, —O-phenyl, —O-benzyl, phenyl and benzyl, in which the respective cyclic portion of the —O-phenyl, —O-benzyl, phenyl, —(CH$_2$)— benzo[b]furanyl and benzyl groups may be substituted with 1, 2, 3, 4 or 5 substituents selected independently of one another from the group consisting of F, Cl, Br, —OH, —CF$_3$, —SF$_5$, —CN, —NO$_2$, —$C_{1-5}$ alkyl, —O—$C_{1-5}$ alkyl, —O—CF$_3$, —S—CF$_3$, phenyl and —O-benzyl and the aforementioned cycloaliphatic groups may optionally each have 1, 2, 3, 4 or 5 heteroatom(s) as the ring member(s) selected independently of one another from the group consisting of oxygen, nitrogen and sulphur;

the aforementioned $C_{1-5}$ alkylene, $C_{2-5}$ alkenylene or $C_{2-5}$ alkynylene groups may optionally each be substituted with 1, 2, 3, 4 or 5 substituents selected independently of one another from the group consisting of F, Cl, Br, —OH, —SH, —NH$_2$, —CN, NO$_2$ and phenyl;

the rings of the aforementioned monocyclic or polycyclic ring systems may optionally each be substituted with 1, 2, 3, 4 or 5 substituents selected independently of one another from the group consisting of oxo (=O), thioxo (=S), F, Cl, Br, I, —CN, —CF$_3$, —SF$_5$, —OH, —O—$C_{1-5}$ alkyl, —NH$_2$, —NO$_2$, —O—CF$_3$, —S—CF$_3$, —SH, —S—$C_{1-5}$ alkyl, —$C_{1-5}$ alkyl, —C(=O)—OH, —C(=O)—O—$C_{1-5}$ alkyl, —NH—$C_{1-5}$ alkyl, —N($C_{1-5}$ alkyl)$_2$, —(CH$_2$)-benzo[b]furanyl, —O-phenyl, —O-benzyl, phenyl and benzyl, in which the respective cyclic portion of the —O-phenyl, —O-benzyl, phenyl, —(CH$_2$)-benzo[b]furanyl and benzyl groups may be substituted with 1, 2, 3, 4 or 5 substituents selected independently of one another from the group consisting of F, Cl, Br, —OH, —CF$_3$, —SF$_5$, —CN, —NO$_2$, —$C_{1-5}$ alkyl, —O—$C_{1-5}$ alkyl, —O—CF$_3$, —S—CF$_3$, phenyl and —O-benzyl; and the rings of the aforementioned monocyclic or polycyclic ring systems each have 5, 6, or 7 members and may optionally each have 1, 2, 3, 4 or 5 heteroatom(s) as the ring member(s) selected independently of one another from the group consisting of oxygen, nitrogen and sulphur; and the aforementioned aryl or heteroaryl groups may optionally each be substituted with 1, 2, 3, 4 or 5 substituents selected independently of one another from the group consisting of F, Cl, Br, I, —CN, —CF$_3$, —SF$_5$, —OH, —O—$C_{1-5}$ alkyl, —NH$_2$, —NO$_2$, —O—CF$_3$, —S—CF$_3$, —SH, —S—$C_{1-5}$ alkyl, —$C_{1-5}$ alkyl, —C(=O)—OH, —C(=O)—O—$C_{1-5}$ alkyl, —NH—$C_{1-5}$ alkyl, —N($C_{1-5}$ alkyl)$_2$, —NH—C(=O)—O—$C_{1-5}$ alkyl, —C(=O)—H, —C(=O)—$C_{1-5}$ alkyl, —C(=O)—NH$_2$, —C(=O)—NH—$C_{1-5}$ alkyl, C(=O)—N—($C_{1-5}$ alkyl)$_2$, —(CH$_2$)-benzo[b]furanyl, —O-phenyl, —O-benzyl, phenyl and benzyl, in which the respective cyclic portion of the —O-phenyl, —O-benzyl, phenyl, —(CH$_2$)-benzo[b]furanyl and benzyl groups may be substituted with 1, 2, 3, 4 or 5 substituents selected independently of one another from the group consisting of F, Cl, Br, —OH, —CF$_3$, —SF$_5$, —CN, —NO$_2$, —$C_{1-5}$ alkyl, —O—$C_{1-5}$ alkyl, —O—CF$_3$, —S—CF$_3$, phenyl and —O-benzyl, and the aforementioned heteroaryl groups may optionally each have 1, 2, 3, 4 or 5 heteroatom(s) as the ring member(s) selected independently of one another from the group consisting of oxygen, nitrogen and sulphur or a corresponding salt thereof.

2. A compound according to claim 1, wherein said compound is in the form of a pure enantiomer or pure diastereomer or a racemic mixture.

3. A compound according to claim 1, wherein said compound is in the form of a mixture of stereoisomers.

4. A compound according to claim 1, wherein $R^1$ represents hydrogen; —C(=O)—OR$^5$; —(CHR$^6$)—(CH$_2$)$_m$—C(=O)—OR$^7$ in which m=0, 1, 2, 3, 4 or 5; —C(=O)—NH—R$^{10}$; —(CH$_2$)$_o$—C(=O)—NHR$^{11}$ in which o=0, 1, 2, 3, 4 or 5; —(CHR$^{16}$)—X$_q$—(CHR$^{17}$)$_r$—Y$_s$—(CHR$^{18}$)$_t$—Z$_u$—R$^{19}$ in which q=0 or 1, r=0 or 1, s=0 or 1, t=0 or 1, u=0 or 1 and in which X, Y and Z, independently of one another, each represent O, S, NH and N(CH$_3$);

an optionally substituted alkyl group selected from the group consisting of methyl, ethyl, n-propyl, isopropyl, —CH$_2$)—(CH$_2$)—(CN), n-butyl, sec-butyl, isobutyl, tert-butyl, —C(H)(CH$_3$)—C(H)(CH$_3$)$_2$ and —(CH$_2$)—(CH$_2$)—(C(CH$_3$)$_3$), an alkenyl group selected from the group consisting of vinyl, 1-propenyl and 2-propenyl, a (hetero)cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, (6,6)-dimethyl-[3.1.1]-bicycloheptyl, indanyl, indenyl, (1,4)-benzodioxanyl, (1,2,3,4)-tetrahydronaphthyl, (1,2,3,4)-tetrahydroquinolinyl and (1,2,3,4)-tetrahydroquinazolinyl, in which the respective (hetero)cycloaliphatic group can optionally be substituted with 1, 2, 3, 4 or 5 substituents selected independently of one another from the group consisting of F, Cl, Br, I, —CN, —CF$_3$, —SF$_5$, —OH, —NH$_2$, —O—CF$_3$, —SH, —O—CH$_3$, —O—C$_2$H$_5$, methyl, ethyl, n-propyl, isopropyl, n-butyl, sec-butyl, isobutyl, tert-butyl, —S—CH$_3$, —S—C$_2$H$_5$, —C(=O)—O—CH$_3$, —C(=O)—O—C$_2$H$_5$, Oxo (=O), —N(CH$_3$)$_2$, —N(C$_2$H$_5$)$_2$, —N(H)(CH$_3$), —N(H)(C$_2$H$_5$), —NO$_2$, —SCF$_3$, —C(=O)—OH, —(CH$_2$)-benzo[b]furanyl, —O-phenyl, —O-benzyl, phenyl and benzyl, in which the respective cyclic portion of the —(CH$_2$)-benzo[b]furanyl, —O-phenyl, —O-benzyl, benzyl and phenyl groups may be substituted with 1, 2, 3, 4 or 5 substituents selected independently of one another from the group consisting of F, Cl, Br, —OH, —CF$_3$, —SF$_5$, —CN, —NO$_2$, methyl, ethyl, isopropyl, n-propyl, —O—CH$_3$, —O—C$_2$H$_5$, —O—CF$_3$, phenyl and —O-benzyl or a group selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, in which the respective group may optionally be substituted with 1, 2, 3, 4 or 5 substituents selected independently of one another from the group consisting of F, Cl, Br, I, —CN, —NO$_2$, —OH, —SH, methyl, ethyl, n-propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$ and —NH—C(=O)—O—C(CH$_3$)$_3$.

5. A compound according to claim 1, wherein
$R^2$ represents hydrogen;
—(CHR$^{16}$)—R$^{19}$; or
an alkyl group selected from the group consisting of methyl, ethyl, n-propyl, isopropyl, n-butyl, sec-butyl, isobutyl and tert-butyl.

6. A compound according to claim 1, wherein
$R^1$ and $R^2$, together with the nitrogen atom which binds them as the ring member, form a heterocycloaliphatic group selected from the group consisting of pyrrolidinyl; piperidinyl; (1,2,3,6)-tetrahydropyridinyl; (1,2,3,4)-tetrahydropyridinyl and (1,4)-dioxa-8-aza-spiro[4.5]decane, in which the respective heterocycloaliphatic group may be substituted with 1 or 2 substituents selected independently of one another from the group consisting of R$^{20}$, —(CHR$^{21}$)—(CH$_2$)$_v$—R$^{22}$ in which v=0 or 1; —C(=O)—OR$^{24}$; —C(=O)—R$^{25}$; F; Cl; Br; —CN; —CF$_3$ and —OH, or $R^1$ and $R^2$, together with the nitrogen atom which binds them as the ring member, form a heterocycloaliphatic group selected from the group consisting of (1,3,4,5)-tetrahydropyrido[4,3-b]indolyl; (3,4)-dihydro-1H-isoquinolinyl and (1,3,4,9)-tetrahydro-[b]-carbolinyl, in which the respective heterocycloaliphatic group may be substituted with 1 or 2 substituents selected independently of one another from the group consisting of F, Cl, Br, —CN, —CF$_3$ and —OH, or $R^1$ and $R^2$, together with the nitrogen atom which binds them as the ring member, form a heterocycloaliphatic group selected from the group consisting of imidazolidinyl, (1,3)-thiazolidinyl, piperazinyl, morpholinyl and thiomorpholinyl, in which the respective heterocycloaliphatic group may be substituted with 1 or 2 substituents selected independently of one another from the group consisting of R$^{20}$, —(CHR$^{21}$)—(CH$_2$)$_v$—(CH$_2$)$_w$—R$^{22}$ in which v=0 or 1 and w=0 or 1, —CH=CH—R$^{23}$, —C(=O)—OR$^{24}$; —C(=O)—R$^{25}$; —(CH$_2$)$_z$—C(=O)—NHR$^{26}$ in which z=1 and —(CH$_2$)$_{aa}$—C(=O)—NR$^{27}$R$^{21}$ in which aa=1.

7. A compound according to claim 1, wherein
$R^3$ represents hydrogen or an alkyl group selected from the group consisting of methyl, ethyl, n-propyl, isopropyl, n-butyl, sec-butyl, isobutyl and tert-butyl and n-pentyl.

8. A compound according to claim 1, wherein
$R^4$ represents a phenyl or naphthyl group which may each be substituted with 1, 2, 3, 4 or 5 substituents selected independently of one another from the group consisting of methyl, ethyl, n-propyl, isopropyl, n-butyl, isobutyl, sec-butyl, tert-butyl, F, Cl, Br, —CN, —SF$_5$, —S—CF$_3$, —NH$_2$, —N(CH$_3$)$_2$, —N(C$_2$H$_5$)$_2$, —N(H)(CH$_3$), —N(H)(C$_2$H$_5$), —SH, —NO$_2$, —CF$_3$, —OCF$_3$, —OH, —O—CH$_3$ and —O—C$_2$H$_5$ and/or bound by a —(CH$_2$)—, —(CH$_2$)$_2$— or —(CH$_2$)$_3$ group.

9. A compound according to claim 1, wherein
$R^5$, $R^7$, $R^8$, $R^9$, $R^{10}$, $R^{11}$, $R^{12}$, $R^{13}$, $R^{14}$ and $R^{15}$, independently of one another, each represent an alkyl group selected from the group consisting of methyl, ethyl, n-propyl, isopropyl, n-butyl, sec-butyl, isobutyl and tert-butyl, in which the respective alkyl group may optionally be substituted with 1, 2, 3, 4 or 5 substituents selected independently of one another from the group consisting of F, Cl, Br, I, —CN, —NO$_2$, —OH, —SH and —NH$_2$, or a group selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, in which the respective group may be bound by a —(CH$_2$)—, —(CH$_2$)$_2$— or —(CH$_2$)$_3$ group and/or optionally substituted with 1, 2, 3, 4 or 5 substituents selected independently of one another from the group consisting of F, Cl, Br, I, —CN, —NO$_2$, —OH, —SH, methyl, ethyl, n-Propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$ and —NH—C(=O)—O—C(CH$_3$)$_3$.

10. A compound according to claim 1, wherein
R$^6$ represents hydrogen,
- a group selected from the group consisting of methyl, ethyl, n-propyl, isopropyl, n-butyl, sec-butyl, isobutyl, tert-butyl, n-pentyl, sec-pentyl, —C(H)(CH$_3$)—C(H)(CH$_3$)$_2$, —(CH$_2$)—(CH$_2$)—(C(CH$_3$)$_3$), —C(H)(CH$_3$)(O(C(CH$_3$)$_3$)) and n-hexyl, in which the respective group may optionally be substituted with 1, 2, 3, 4 or 5 substituents selected independently of one another from the group consisting of F, Cl, Br, I, —CN, —NO$_2$, —OH, —SH and —NH$_2$,
- or a group selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, in which the respective group may be bound by a —(CH$_2$)—, —(CH$_2$)$_2$— or —(CH$_2$)$_3$ group and/or optionally substituted with 1, 2, 3, 4 or 5 substituents selected independently of one another from the group consisting of F, Cl, Br, I, —CN, —NO$_2$, —OH, —SH, methyl, ethyl, n-propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$ and —NH—C(=O)—O—C(CH$_3$)$_3$.

11. A compound according to claim 1, wherein
R$^{16}$, R$^{17}$ and R$^{18}$, independently of one another, each represent hydrogen,
- a group selected from the group consisting of methyl, ethyl, n-propyl, isopropyl, n-butyl, sec-butyl, isobutyl, tert-butyl, n-pentyl, sec-pentyl, —C(H)(CH$_3$)—C(H)(CH$_3$)$_2$, —(CH$_2$)—(CH$_2$)—(C(CH$_3$)$_3$), —(CH$_2$)—O—(CH$_3$) and n-hexyl, in which the respective group may optionally be substituted with 1, 2, 3, 4 or 5 substituents, selected independently of one another from the group consisting of F, Cl, Br, I, —CN, —NO$_2$, —OH, —SH and —NH$_2$, or
- a group selected from the group consisting of phenyl and naphthyl, in which the respective group may be substituted with 1, 2, 3, 4 or 5 substituents selected independently of one another from the group consisting of F, Cl, Br, I, —CN, —NO$_2$, —OH, —SH, methyl, ethyl, n-propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$ and —NH—C(=O)—O—C(CH$_3$)$_3$.

12. A compound according to claim 1, wherein
R$^{19}$ represents a cycloaliphatic group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl, dithiolanyl, (6,6)-dimethyl-[3.1.1]-bicycloheptyl, adamantyl (tricyclo-[3.3.1.1$^{3,7}$]-decanyl), indanyl, indenyl, (1,4)-benzodioxanyl, (1,2,3,4)-tetrahydronaphthyl, (1,2,3,4)-tetrahydroquinolinyl and (1,2,3,4)-tetrahydroquinazolinyl, in which the respective cycloaliphatic group may optionally be substituted with 1, 2, 3, 4 or 5 substituents selected independently of one another from the group consisting of F, Cl, Br, I, —CN, —CF$_3$, —SF$_5$, —OH, —NH$_2$, —O—CF$_3$, —SH, —O—CH$_3$, —O—C$_2$H$_5$, methyl, ethyl, n-propyl, isopropyl, n-butyl, sec-butyl, isobutyl, tert-butyl, —S—CH$_3$, —S—C$_2$H$_5$, —C(=O)—O—CH$_3$, —C(=O)—O—C$_2$H$_5$, oxo (=O), —N(CH$_3$)$_2$, —N(C$_2$H$_5$)$_2$, —N(H)(CH$_3$), —N(H)(C$_2$H$_5$), —NO$_2$, —SCF$_3$, —C(=O)—OH, —(CH$_2$)-benzo[b]furanyl, —O-phenyl, —O-benzyl, phenyl and benzyl, and which cycloaliphatic group may optionally include at least one heteroatom
- or a group selected from the group consisting of phenyl, naphthyl, (1,3)-benzodioxolyl, (1,4)-benzodioxanyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, quinazolinyl, quinolinyl and isoquinolinyl, in which the respective group may optionally be substituted with 1, 2, 3, 4 or 5 substituents selected independently of one another from the group consisting of F, Cl, Br, I, —CN, —NO$_2$, —OH, —SH, methyl, ethyl, n-propyl, isopropyl, n-butyl, sec-butyl, isobutyl, tert-butyl, —CF$_3$, —O—CF$_3$, —S—CF$_3$, —SF$_5$, —O—CH$_3$, —O—C$_2$H$_5$, —O-phenyl, —O-benzyl, —NH$_2$, —N(CH$_3$)$_2$, —N(C$_2$H$_5$)$_2$, —N(H)(CH$_3$), —N(H)(C$_2$H$_5$), —NH—C(=O)—O—CH$_3$, —NH—C(=O)—O—C$_2$H$_5$ and —NH—C(=O)—O—C(CH$_3$)$_3$.

13. A compound according to claim 1, wherein
R$^{20}$ represents an alkyl group selected from the group consisting of methyl, ethyl, n-propyl, isopropyl, n-butyl, isobutyl, sec-butyl, tert-butyl and n-pentyl, a (hetero) cycloaliphatic group selected from the group consisting of cyclopentyl, cyclohexyl, piperidinyl and cycloheptyl, in which the respective (hetero)cycloaliphatic group may optionally be substituted with 1, 2, 3, 4 or 5 substituents selected independently of one another from the group consisting of F, Cl, Br, I, —CN, —CF$_3$, —SF$_5$, —OH, —NH$_2$, —O—CF$_3$, —SH, —O—CH$_3$, —O—C$_2$H$_5$, methyl, ethyl, n-propyl, isopropyl, n-butyl, sec-butyl, isobutyl and tert-butyl,
- or a group selected from the group consisting of phenyl, naphthyl, (1,3)-benzodioxolyl, thiophenyl, furanyl, pyridinyl, imidazolyl, indolyl, benzo[b]furanyl, benzo[b]thiophenyl, thiazolyl, oxazolyl, isoxazolyl, pyridazinyl, pyrazinyl, pyrimidinyl, and quinolinyl, in which the respective group may optionally be substituted with 1, 2, 3, 4 or 5 substituents selected independently of one another from the group consisting of methyl, ethyl, n-propyl, isopropyl, n-butyl, isobutyl, sec-butyl, tert-butyl, F, Cl, Br, —CN, —SF$_5$, —O—CF$_3$, —S—CF$_3$, —NH$_2$, —N(CH$_3$)$_2$, —N(C$_2$H$_5$)$_2$, —N(H)(CH$_3$), —N(H)(C$_2$H$_5$), —SH, —NO$_2$, —CF$_3$, —OCF$_3$, —OH, —O—CH$_3$ and —O—C$_2$H$_5$.

14. A compound according to claim 1, wherein
R$^{21}$ represents hydrogen
or a phenyl or naphthyl group, which may be substituted with 1, 2 or 3 substituents selected independently of one another from the group consisting of methyl, ethyl, n-propyl, isopropyl, n-butyl, isobutyl, sec-butyl, tert-butyl, F, Cl and Br.

15. A compound according to claim 1, wherein
R$^{22}$ and R$^{23}$, independently of one another, are each selected from the group consisting of pyrrolidinyl, morpholinyl and thiomorpholinyl, which may optionally be substituted with 1, 2, 3, 4 or 5 substituents selected independently of one another from the group consisting of F, Cl, Br, I, —CN, —CF$_3$, —SF$_5$, —OH, —NH$_2$, —O—CF$_3$, —SH, —O—CH$_3$, —O—C$_2$H$_5$, methyl, ethyl, n-propyl, isopropyl, n-butyl, sec-butyl, isobutyl and tert-butyl, or are selected from the group consisting of phenyl, naphthyl, (1,3)-benzodioxolyl, thiophenyl, furanyl, pyridinyl, imidazolyl, indolyl, benzo[b]furanyl, benzo[b]thiophenyl, thiazolyl, oxazolyl, isoxazolyl, pyridazinyl, pyrazinyl, pyrimidinyl, and quinolinyl, in which the respective group may optionally be substituted with 1, 2, 3, 4 or 5 substituents selected independently of one another from the group consisting of methyl, ethyl, n-propyl, isopropyl, n-butyl, isobutyl, sec-butyl, tert-butyl, F, Cl, Br, —CN, —SF$_5$, —O—CF$_3$, —S—CF$_3$, —NH$_2$, —N(CH$_3$)$_2$, —N(C$_2$H$_5$)$_2$, —N(H)(CH$_3$), —N(H)(C$_2$H$_5$), —SH, —NO$_2$, —CF$_3$, —OCF$_3$, —OH, —O—CH$_3$ and —O—C$_2$H$_5$.

16. A compound according to claim 1, wherein
R$^{24}$ represents an alkyl group selected from the group consisting of methyl, ethyl, n-propyl, isopropyl, n-butyl, sec-butyl, isobutyl and tert-butyl,
R$^{25}$ represents a group selected from the group consisting of phenyl, naphthyl, furanyl, pyrazinyl and pyrimidinyl, which may be bound by a —(CH$_2$)—, —(CH$_2$)$_2$— or —(CH$_2$)$_3$ group and/or substituted with 1, 2 or 3 substituents selected independently of one another from the group consisting of methyl, ethyl, n-propyl and isopropyl,
R$^{26}$ represents an alkyl group selected from the group consisting of methyl, ethyl, n-propyl and isopropyl,
R$^{27}$ represents an alkyl group selected from the group consisting of methyl, ethyl, isopropyl and n-propyl or a phenyl group, and
R$^{28}$ represents an alkyl group selected from the group consisting of methyl, ethyl, isopropyl and n-propyl or a phenyl group.

17. A compound according to claim 1, wherein
R$^1$ represents —C(=O)—OR$^5$; —(CHR$^6$)—C(=O)—OR$^7$;
—C(=O)—NHR$^{11}$; —(CH$_2$)—C(=O)—NHR$^{11}$;
—(CHR$^{16}$)—R$^{19}$; —(CHR$^{16}$)—(CHR$^{17}$)—R$^{19}$;
—(CHR$^{16}$)—(CHR$^{17}$)—O—R$^{19}$; —(CHR$^{16}$)—(CHR$^{17}$)—(CHR$^{18}$)—R$^{19}$; —(CHR$^{16}$)—(CHR$^{17}$)—S—(CHR$^{18}$)—R$^{19}$; —(CHR$^{16}$)—(CHR$^{17}$)—(CHR$^{18}$)—N(CH$_3$)—R$^{19}$, an optionally substituted alkyl group selected from the group consisting of methyl, ethyl, n-propyl, isopropyl, —CH$_2$—CH$_2$—CN, n-butyl, sec-butyl, isobutyl, tert-butyl, —CH(CH$_3$)—CH(CH$_3$)$_2$ and —CH$_2$—CH$_2$—C(CH$_3$)$_3$, an alkenyl group selected from the group consisting of 1-propenyl and 2-propenyl, a group selected from the group consisting of cyclopentyl, cyclohexyl, cycloheptyl, (6,6)-dimethyl-[3.1.1]-bicycloheptyl, indanyl and indenyl, in which the respective group may be substituted with 1, 2 or 3 substituents selected independently of one another from the group consisting of F, Cl, Br, methyl, ethyl, isopropyl, n-propyl and —O-benzyl, a pyrrolidinyl group which may be substituted with a —(CH$_2$)-benzo[b]furanyl or benzyl group, in which the respective cyclic portion of the benzyl group may be substituted with 1, 2 or 3 substituents selected independently of one another from the group consisting of F, Cl, Br, —OH, methyl, ethyl, isopropyl, n-propyl, —CF$_3$, —O—CH$_3$, —O—C$_2$H$_5$, phenyl and —O-benzyl, or a group selected from the group consisting of phenyl, naphthyl, (1,3)-benzodioxolyl and (1,4)-benzodioxanyl, in which the respective group may be substituted with 1, 2 or 3 substituents selected independently of one another from the group consisting of F, Cl, Br, I, methyl, ethyl, n-propyl, isopropyl, n-butyl, sec-butyl, isobutyl, tert-butyl, —O-phenyl, —O-benzyl, —NH—C(=O)—O—CH$_3$, —NH—C(=O)—O—C$_2$H$_5$ and —NH—C(=O)—O—C(CH$_3$)$_3$;

R$^2$ represents hydrogen,
—(CHR$^{16}$)—R$^{19}$,
or an alkyl group selected from the group consisting of methyl, ethyl, n-propyl, isopropyl, n-butyl, sec-butyl, isobutyl and tert-butyl; or R$^1$ and R$^2$, together with the nitrogen atom which binds them as the ring member, form a group selected from the group consisting of

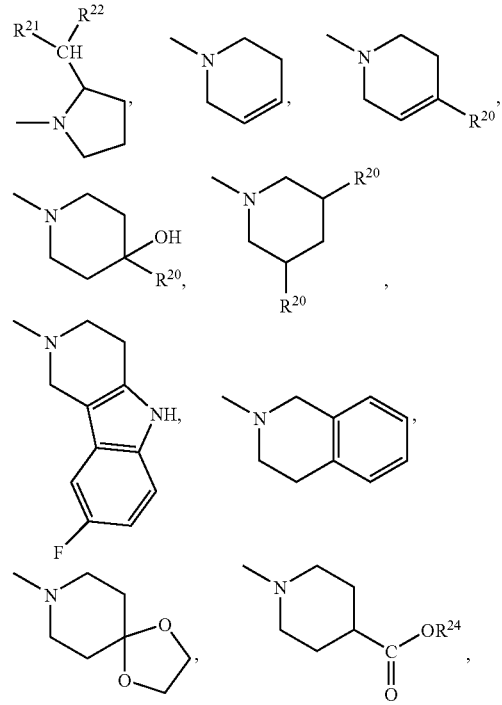

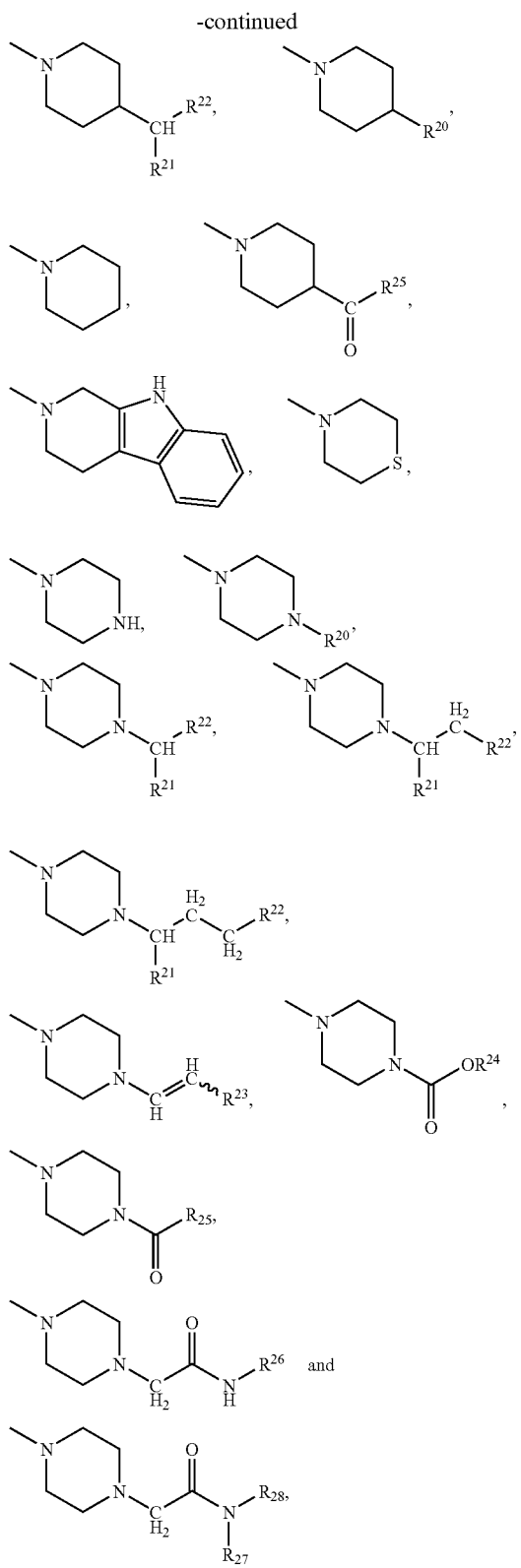

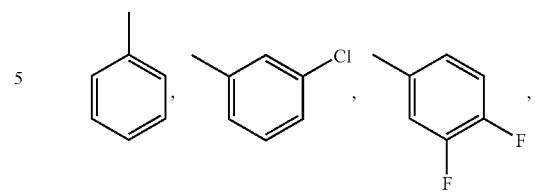

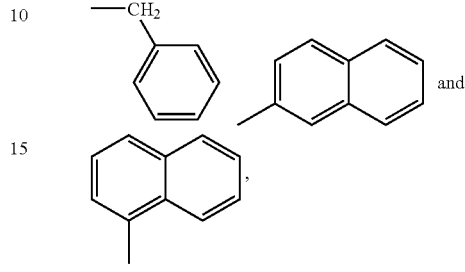

$R^5$, $R^7$ and $R^{11}$, independently of one another, each represent
  an alkyl group selected from the group consisting of methyl, ethyl, n-propyl, isopropyl, n-butyl, sec-butyl, isobutyl and tert-butyl;
  or benzyl or naphthyl group;

$R^6$ represents hydrogen,
  a group selected from the group consisting of methyl, ethyl, n-propyl, isopropyl, n-butyl, sec-butyl, isobutyl, tert-butyl, n-pentyl, sec-pentyl, neopentyl and —C(H)(CH$_3$)(O(C(CH$_3$)$_3$)),
  or an indolyl group, bound by a —(CH$_2$) group;

$R^{16}$ represents hydrogen,
  a group selected from the group consisting of methyl, ethyl, isopropyl, n-propyl, n-butyl, sec-butyl, isobutyl, tert-butyl and —(CH$_2$)—O—(CH$_3$),
  or a phenyl group;

$R^{17}$ represents hydrogen,
  an alkyl group selected from the group consisting of methyl, ethyl, n-propyl, isopropyl, n-butyl, isobutyl, sec-butyl and tert-butyl or a phenyl group;

$R^{18}$ represents hydrogen, or a phenyl group;

$R^{19}$ represents is selected from the group consisting of cyclopentyl, cyclohexyl, cycloheptyl, tetrahydrofuranyl, tetrahydrothiophenyl, pyrrolidinyl, piperidinyl, adamantyl (tricyclo-[3.3.1.1$^{3,7}$]-decanyl) and (1,4)-benzodioxanyl, which may be substituted with 1 or 2 substituents selected independently of one another from the group consisting of methyl, ethyl, isopropyl and n-propyl,
  or a group selected from the group consisting of phenyl, naphthyl, (1,3)-benzodioxolyl, (1,4)-benzodioxanyl, thiophenyl, furanyl, pyridinyl, imidazolyl, indolyl and isoindolyl, in which the respective group may be substituted with 1, 2, 3, 4 or 5 substituents selected independently of one another from the group consisting of F, Cl, Br, I, methyl, ethyl, n-propyl, isopropyl, n-butyl, sec-butyl, isobutyl, tert-butyl, —CF$_3$, —O—CH$_3$, —O—C$_2$H$_5$, —O—CF$_3$, —O-Phenyl, —O-Benzyl, —NH$_2$, —N(CH$_3$)$_2$, —N(C$_2$H$_5$)$_2$, —N(H)(CH$_3$) and —N(H)(C$_2$H$_5$);

$R^{20}$ represents a methyl or ethyl group,
  a (hetero)cycloaliphatic group selected from the group consisting of cyclopentyl, cyclohexyl, piperidinyl and cycloheptyl, $R^3$ represents an alkyl group selected from the group consisting of methyl, ethyl, n-propyl, isopropyl, n-butyl, sec-butyl, isobutyl and tert-butyl;

$R^4$ represents a group selected from the group consisting of or a phenyl or pyridinyl group, which may be substituted with 1, 2 or 3 substituents selected independently of one another from the group consisting of methyl, ethyl, n-propyl, isopropyl, n-butyl, isobutyl, sec-butyl, tert-butyl, F, Cl, Br, —CF$_3$, —OH, —O—CH$_3$ and —O—C$_2$H$_5$;

$R^{21}$ represents hydrogen or a phenyl group, which may be substituted with 1, 2 or 3 substituents selected independently of one another from the group consisting of methyl, ethyl, n-propyl, isopropyl, n-butyl, isobutyl, sec-butyl, tert-butyl, F, Cl and Br;

$R^{22}$ represents a pyrrolidinyl or morpholinyl group or a group selected from the group consisting of phenyl, naphthyl, (1,3)-benzodioxolyl, thiophenyl, benzo[b]furanyl, benzo[b]thiophenyl and quinolinyl, in which the respective group may be substituted with 1, 2 or 3 substituents selected independently of one another from the group consisting of methyl, ethyl, n-propyl, F, Cl, Br, —OH, —O—CH$_3$ and —O—C$_2$H$_5$;

$R^{23}$ represents a phenyl group;

$R^{24}$ represents an alkyl group selected from the group consisting of methyl, ethyl, n-propyl, isopropyl, n-butyl, isobutyl, sec-butyl and tert-butyl;

$R^{25}$ represents a group selected from the group consisting of phenyl, naphthyl, furanyl, pyrazinyl and pyrimidinyl, which may be bound by a —(CH$_2$) group and/or substituted with 1, 2 or 3 substituents selected independently of one another from the group consisting of methyl, ethyl, n-propyl and isopropyl;

$R^{26}$ represents an alkyl group selected from the group consisting of methyl, ethyl, n-propyl and isopropyl;

$R^{27}$ represents an alkyl group selected from the group consisting of methyl, ethyl, isopropyl and n-propyl and $R^{28}$ represents a phenyl group;

or a corresponding salt thereof.

18. A compound according to claim 1, wherein said compound is selected from the group consisting of:

[1] 2-[(3-chlorobenzoyl)-methyl-amino]-5,6,7,8-tetrahydro-imidazo[1,2-a]pyridine-3-carboxylic acid (2-thiophen-2-yl-ethyl)-amide,

[2] 2-[butyl-(3-chlorobenzoyl)-amino]-5,6,7,8-tetrahydro-imidazo[1,2-a]pyridine-3-carboxylic acid [2-(2,5-dimethoxy-phenyl)-ethyl]-amide,

[3] N-{3-[4-(2-ethyl-phenyl)-piperazine-1-carbonyl]-5,6,7,8-tetrahydro-imidazo[1,2-a]pyridin-2-yl}-N-methyl-benzamide,

[4] 2-(methyl-phenylacetyl-amino)-5,6,7,8-tetrahydro-imidazo[1,2-a]pyridine-3-carboxylic acid [3-(2-methyl-piperidin-1-yl)-propyl]-amide,

[5] 2-[(3-chlorobenzoyl)-methyl-amino]-5,6,7,8-tetrahydro-imidazo[1,2-a]pyridine-3-carboxylic acid (2-phenyl-propyl)-amide,

[6] 2-[(3-chlorobenzoyl)-methyl-amino]-5,6,7,8-tetrahydro-imidazo[1,2-a]pyridine-3-carboxylic acid (2-pyrrolidin-1-yl-ethyl)-amide,

[7] 2-[methyl-(naphthalene-1-carbonyl)-amino]-5,6,7,8-tetrahydro-imidazo[1,2-a]pyridine-3-carboxylic acid ethyl-pyridin-4-ylmethyl-amide,

[8] 2-(benzoyl-methyl-amino)-5,6,7,8-tetrahydro-imidazo[1,2-a]pyridine-3-carboxylic acid (2-thiophen-2-yl-ethyl)-amide,

[9] 2-[butyl-(3-chlorobenzoyl)-amino]-5,6,7,8-tetrahydro-imidazo[1,2-a]pyridine-3-carboxylic acid (3-imidazol-1-yl-propyl)-amide,

[10] 3-chloro-N-{3-[4-(3-chlorophenyl)-piperazine-1-carbonyl]-5,6,7,8-tetrahydro-imidazo[1,2-a]pyridin-2-yl}-N-methyl-benzamide,

[11] 3-chloro-N-methyl-N-[3-(4-phenyl-piperazine-1-carbonyl)-5,6,7,8-tetrahydro-imidazo[1,2-a]pyridin-2-yl]-benzamide,

[12] 2-[butyl-(3,4-difluorobenzoyl)-amino]-5,6,7,8-tetrahydro-imidazo[1,2-a]pyridine-3-carboxylic acid indan-1-ylamide,

[13] N-butyl-3-chloro-N-{3-[4-(2-morpholin-4-yl-ethyl)-piperazine-1-carbonyl]-5,6,7,8-tetrahydro-imidazo[1,2-a]pyridin-2-yl}-benzamide,

[14] 3-chloro-N-methyl-N-{3-[4-(3-trifluoromethyl-phenyl)-piperazine-1-carbonyl]-5,6,7,8-tetrahydro-imidazo[1,2-a]pyridin-2-yl}-benzamide,

[15] 2-[methyl-(naphthalene-1-carbonyl)-amino]-5,6,7,8-tetrahydro-imidazo[1,2-a]pyridine-3-carboxylic acid 3,5-bis-trifluoromethyl-benzylamide,

[16] 2-[butyl-(3,4-difluorobenzoyl)-amino]-5,6,7,8-tetrahydro-imidazo[1,2-a]pyridine-3-carboxylic acid (4-methyl-cyclohexyl)-amide,

[17] 2-(benzoyl-methyl-amino)-5,6,7,8-tetrahydro-imidazo[1,2-a]pyridine-3-carboxylic acid 3-methoxy-benzylamide,

[18] 2-[methyl-(naphthalene-1-carbonyl)-amino]-5,6,7,8-tetrahydro-imidazo[1,2-a]pyridine-3-carboxylic acid (1-p-tolyl-ethyl)-amide,

[19] 2-[butyl-(3-chlorobenzoyl)-amino]-5,6,7,8-tetrahydro-imidazo[1,2-a]pyridine-3-carboxylic acid (1,2-dimethyl-propyl)-amide,

[20] 2-(benzoyl-methyl-amino)-5,6,7,8-tetrahydro-imidazo[1,2-a]pyridine-3-carboxylic acid (4-methyl-cyclohexyl)-amide,

[21] 2-(benzoyl-methyl-amino)-5,6,7,8-tetrahydro-imidazo[1,2-a]pyridine-3-carboxylic acid (2-phenyl-propyl)-amide,

[22] 4-[2-(benzoyl-methyl-amino)-5,6,7,8-tetrahydro-imidazo[1,2-a]pyridine-3-carbonyl]-piperazine-1-carboxylic acid ethyl ester,

[23] 3-chloro-N-methyl-N-(3-{4-[(methyl-phenyl-carbamoyl)-methyl]-piperazine-1-carbonyl}-5,6,7,8-tetrahydro-imidazo[1,2-a]pyridin-2-yl)-benzamide,

[24] 3-chloro-N-{3-[4-(furan-2-carbonyl)-piperazine-1-carbonyl]-5,6,7,8-tetrahydro-imidazo[1,2-a]pyridin-2-yl}-N-methyl-benzamide,

[25] N-methyl-N-[3-(4-p-tolyl-piperazine-1-carbonyl)-5,6,7,8-tetrahydro-imidazo[1,2-a]pyridin-2-yl]-benzamide,

[26] N-butyl-3-chloro-N-{3-[4-(3-phenyl-propyl)-piperazine-1-carbonyl]-5,6,7,8-tetrahydro-imidazo[1,2-a]pyridin-2-yl}-benzamide,

[27] 2-[(3-chlorobenzoyl)-methyl-amino]-5,6,7,8-tetrahydro-imidazo[1,2-a]pyridine-3-carboxylic acid (2,6,6-trimethyl-bicyclo[3.1.1]hept-3-yl)-amide,

[28] 2-[butyl-(3,4-difluorobenzoyl)-amino]-5,6,7,8-tetrahydro-imidazo[1,2-a]pyridine-3-carboxylic acid (3-phenyl-propyl)-amide,

[29] naphthalene-1-carboxylic acid {3-[4-(4-methoxy-phenyl)-piperazine-1-carbonyl]-5,6,7,8-tetrahydro-imidazo[1,2-a]pyridin-2-yl}-methyl-amide,

[30] 2-[methyl-(naphthalene-1-carbonyl)-amino]-5,6,7,8-tetrahydro-imidazo[1,2-a]pyridine-3-carboxylic acid [1-(4-trifluoromethyl-benzyl)-pyrrolidin-3-yl]-amide,

[31] 2-[(3-chlorobenzoyl)-methyl-amino]-5,6,7,8-tetrahydro-imidazo[1,2-a]pyridine-3-carboxylic acid (4-ethyl-phenyl)-amide,

[32] 2-[methyl-(naphthalene-1-carbonyl)-amino]-5,6,7,8-tetrahydro-imidazo[1,2-a]pyridine-3-carboxylic acid (3-methoxy-benzyl)-(tetrahydro-furan-2-ylmethyl)-amide,

[33] 2-[methyl-(naphthalene-1-carbonyl)-amino]-5,6,7,8-tetrahydro-imidazo[1,2-a]pyridine-3-carboxylic acid 2,3-dichloro-benzylamide,

[34] 2-[butyl-(3,4-difluorobenzoyl)-amino]-5,6,7,8-tetrahydro-imidazo[1,2-a]pyridine-3-carboxylic acid (1-benzofuran-2-ylmethyl-pyrrolidin-3-yl)-methyl-amide,

[35] 3-chloro-N-{3-[4-(4-chlorophenyl)-piperazine-1-carbonyl]-5,6,7,8-tetrahydro-imidazo[1,2-a]pyridin-2-yl}-N-methyl-benzamide,

[36] 2-({2-[(3-chlorobenzoyl)-methyl-amino]-5,6,7,8-tetrahydro-imidazo[1,2-a]pyridine-3-carbonyl}-amino)-3-(1H-indol-3-yl)-propanoic acid methyl ester,

[37] N-butyl-3-chloro-N-[3-(4-phenylacetyl-piperazine-1-carbonyl)-5,6,7,8-tetrahydro-imidazo[1,2-a]pyridin-2-yl]-benzamide,

[38] 2-({2-[(3-chlorobenzoyl)-methyl-amino]-5,6,7,8-tetrahydro-imidazo[1,2-a]pyridine-3-carbonyl}-amino)-3-methyl-pentanoic acid-tert-butyl ester,

[39] 2-[butyl-(3-chlorobenzoyl)-amino]-5,6,7,8-tetrahydro-imidazo[1,2-a]pyridine-3-carboxylic acid (1-naphthalen-1-yl-ethyl)-amide,

[40] 2-[methyl-(naphthalene-1-carbonyl)-amino]-5,6,7,8-tetrahydro-imidazo[1,2-a]pyridine-3-carboxylic acid allyl-methyl-amide,

[41] N-butyl-N-[3-(3,6-dihydro-2H-pyridine-1-carbonyl)-5,6,7,8-tetrahydro-imidazo[1,2-a]pyridin-2-yl]-3,4-difluoro-benzamide,

[42] 2-({2-[(3-chlorobenzoyl)-methyl-amino]-5,6,7,8-tetrahydro-imidazo[1,2-a]pyridine-3-carbonyl}-amino)-4-methyl-pentanoic acid-benzyl ester,

[43] 2-[butyl-(3-chlorobenzoyl)-amino]-5,6,7,8-tetrahydro-imidazo[1,2-a]pyridine-3-carboxylic acid 2-ethoxy-benzylamide,

[44] N-butyl-3-chloro-N-{3-[4-(5-methyl-pyrazine-2-carbonyl)-piperazine-1-carbonyl]-5,6,7,8-tetrahydro-imidazo[1,2-a]pyridin-2-yl}-benzamide,

[45] N-[3-(4-benzo[1,3]dioxol-5-ylmethyl-piperazine-1-carbonyl)-5,6,7,8-tetrahydro-imidazo[1,2-a]pyridin-2-yl]-3-chloro-N-methyl-benzamide,

[46] 2-[methyl-(naphthalene-1-carbonyl)-amino]-5,6,7,8-tetrahydro-imidazo[1,2-a]pyridine-3-carboxylic acid (2,2-diphenyl-ethyl)-amide,

[47] 2-[butyl-(3-chlorobenzoyl)-amino]-5,6,7,8-tetrahydro-imidazo[1,2-a]pyridine-3-carboxylic acid 2,4-difluoro-benzylamide,

[48] N-butyl-3-chloro-N-{3-[4-(2-fluoro-phenyl)-piperazine-1-carbonyl]-5,6,7,8-tetrahydro-imidazo[1,2-a]pyridin-2-yl}-benzamide,

[49] 2-[methyl-(naphthalene-1-carbonyl)-amino]-5,6,7,8-tetrahydro-imidazo[1,2-a]pyridine-3-carboxylic acid (2-p-tolyl-ethyl)-amide,

[50] 2-[methyl-(naphthalene-1-carbonyl)-amino]-5,6,7,8-tetrahydro-imidazo[1,2-a]pyridine-3-carboxylic acid (pyridin-2-ylmethyl)-amide,

[51] 2-[butyl-(3-chlorobenzoyl)-amino]-5,6,7,8-tetrahydro-imidazo[1,2-a]pyridine-3-carboxylic acid 2-trifluoromethyl-benzylamide,

[52] 2-[butyl-(3-chlorobenzoyl)-amino]-5,6,7,8-tetrahydro-imidazo[1,2-a]pyridine-3-carboxylic acid indan-1-ylamide,

[53] 3-chloro-N-methyl-N-[3-(4-quinolin-2-ylmethyl-piperazine-1-carbonyl)-5,6,7,8-tetrahydro-imidazo[1,2-a]pyridin-2-yl]-benzamide,

[54] N-butyl-3,4-difluoro-N-[3-(4-methyl-piperazine-1-carbonyl)-5,6,7,8-tetrahydro-imidazo[1,2-a]pyridin-2-yl]-benzamide,

[55] 2-[(3-chlorobenzoyl)-methyl-amino]-5,6,7,8-tetrahydro-imidazo[1,2-a]pyridine-3-carboxylic acid 2,4-difluoro-benzylamide,

[56] N-[3-(4-benzhydryl-piperazine-1-carbonyl)-5,6,7,8-tetrahydro-imidazo[1,2-a]pyridin-2-yl]-N-butyl-3,4-difluoro-benzamide,

[57] 4-methyl-2-({2-[methyl-(naphthalene-1-carbonyl)-amino]-5,6,7,8-tetrahydro-imidazo[1,2-a]pyridine-3-carbonyl}-amino)-pentanoic acid-benzyl ester,

[58] 2-[butyl-(3-chlorobenzoyl)-amino]-5,6,7,8-tetrahydro-imidazo[1,2-a]pyridine-3-carboxylic acid (2-pyrrolidin-1-yl-ethyl)-amide,

[59] 2-[(3-chlorobenzoyl)-methyl-amino]-5,6,7,8-tetrahydro-imidazo[1,2-a]pyridine-3-carboxylic acid [1-(2-benzyloxy-benzyl)-pyrrolidin-3-yl]-amide,

[60] 2-[butyl-(3,4-difluorobenzoyl)-amino]-5,6,7,8-tetrahydro-imidazo[1,2-a]pyridine-3-carboxylic acid (pyridin-3-ylmethyl)-amide,

[61] 3-chloro-N-{3-[4-(4-fluorophenyl)-3,6-dihydro-2H-pyridine-1-carbonyl]-5,6,7,8-tetrahydro-imidazo[1,2-a]pyridin-2-yl}-N-methyl-benzamide,

[62] 2-[(3-chlorobenzoyl)-methyl-amino]-5,6,7,8-tetrahydro-imidazo[1,2-a]pyridine-3-carboxylic acid cyclohexylamide, c[63] N-[3-(4-Cycloheptyl-piperazine-1-carbonyl)-5,6,7,8-tetrahydro-imidazo[1,2-a]pyridin-2-yl]-N-methyl-benzamide,

[64] naphthalene-1-carboxylic acid methyl-[3-(4-thiophen-3-ylmethyl-piperazine-1-carbonyl)-5,6,7,8-tetrahydro-imidazo[1,2-a]pyridin-2-yl]-amide,

[65] 2-[butyl-(3-chlorobenzoyl)-amino]-5,6,7,8-tetrahydro-imidazo[1,2-a]pyridine-3-carboxylic acid 2,4-dimethoxy-benzylamide,

[66] 1-[2-(benzoyl-methyl-amino)-5,6,7,8-tetrahydro-imidazo[1,2-a]pyridine-3-carbonyl]-piperidine-4-carboxylic acid ethyl ester,

[67] 2-[(3-chlorobenzoyl)-methyl-amino]-5,6,7,8-tetrahydro-imidazo[1,2-a]pyridine-3-carboxylic acid (2-benzyloxy-cyclohexyl)-amide,

[68] 2-[methyl-(naphthalene-1-carbonyl)-amino]-5,6,7,8-tetrahydro-imidazo[1,2-a]pyridine-3-carboxylic acid [2-(4-phenoxy-phenyl)-ethyl]-amide,

[69] 2-[butyl-(3-chlorobenzoyl)-amino]-5,6,7,8-tetrahydro-imidazo[1,2-a]pyridine-3-carboxylic acid [2-(7-methyl-1H-indol-3-yl)-ethyl]-amide,

[70] naphthalene-1-carboxylic acid methyl-[3-(4-phenyl-piperazine-1-carbonyl)-5,6,7,8-tetrahydro-imidazo[1,2-a]pyridin-2-yl]-amide,

[71] 2-[(3-chloro-benzoyl)-methyl-amino]-5,6,7,8-tetrahydro-imidazo[1,2-a]pyridine-3-carboxylic acid [2-(3-trifluoromethyl-phenyl)-ethyl]-amide,

[72] N-butyl-3-chloro-N-[3-(4-pyridin-2-yl-piperazine-1-carbonyl)-5,6,7,8-tetrahydro-imidazo[1,2-a]pyridin-2-yl]-benzamide,

[73] 2-[methyl-(naphthalene-1-carbonyl)-amino]-5,6,7,8-tetrahydro-imidazo[1,2-a]pyridine-3-carboxylic acid 3-methoxy-benzylamide,

[74] 2-[butyl-(3,4-difluorobenzoyl)-amino]-5,6,7,8-tetrahydro-imidazo[1,2-a]pyridine-3-carboxylic acid 2,4-difluoro-benzylamide,

[75] 3-chloro-N-methyl-N-[3-(4-pyridin-2-yl-piperazine-1-carbonyl)-5,6,7,8-tetrahydro-imidazo[1,2-a]pyridin-2-yl]-benzamide,

[76] 2-[methyl-(naphthalene-1-carbonyl)-amino]-5,6,7,8-tetrahydro-imidazo[1,2-a]pyridine-3-carboxylic acid (1-biphenyl-4-ylmethyl-pyrrolidin-3-yl)-methyl-amide,

[77] 2-[butyl-(3-chlorobenzoyl)-amino]-5,6,7,8-tetrahydro-imidazo[1,2-a]pyridine-3-carboxylic acid (2,3-dihydro-benzo[1,4]dioxin-2-ylmethyl)-amide,

[78] 2-[butyl-(3-chlorobenzoyl)-amino]-5,6,7,8-tetrahydro-imidazo[1,2-a]pyridine-3-carboxylic acid [2-(1H-indol-3-yl)-ethyl]-methyl-amide,

[79] N-butyl-3-chloro-N-{3-[4-(3-trifluoromethyl-phenyl)-piperazine-1-carbonyl]-5,6,7,8-tetrahydro-imidazo[1,2-a]pyridin-2-yl}-benzamide,

[80] 2-(benzoyl-methyl-amino)-5,6,7,8-tetrahydro-imidazo[1,2-a]pyridine-3-carboxylic acid [2-(1H-indol-3-yl)-ethyl]-methyl-amide,

[81] 3-chloro-N-{3-[4-hydroxy-4-(3-trifluoromethyl-phenyl)-piperidine-1-carbonyl]-5,6,7,8-tetrahydro-imidazo[1,2-a]pyridin-2-yl}-N-methyl-benzamide,

[82] 2-[butyl-(3,4-difluorobenzoyl)-amino]-5,6,7,8-tetrahydro-imidazo[1,2-a]pyridine-3-carboxylic acid (1-methoxymethyl-2-phenyl-ethyl)-amide,

[83] 2-[(3-chlorobenzoyl)-methyl-amino]-5,6,7,8-tetrahydro-imidazo[1,2-a]pyridine-3-carboxylic acid [1-(2,6-dichloro-benzyl)-pyrrolidin-3-yl]-amide,

[84] 2-[(3-chlorobenzoyl)-methyl-amino]-5,6,7,8-tetrahydro-imidazo[1,2-a]pyridine-3-carboxylic acid [1-(2-bromo-4,5-dimethoxy-benzyl)-pyrrolidin-3-yl]-amide,

[85] 2-(benzoyl-methyl-amino)-5,6,7,8-tetrahydro-imidazo[1,2-a]pyridine-3-carboxylic acid benzo[1,3]dioxol-5-ylamide,

[86] 2-[butyl-(3-chlorobenzoyl)-amino]-5,6,7,8-tetrahydro-imidazo[1,2-a]pyridine-3-carboxylic acid (1-methoxymethyl-2-phenyl-ethyl)-amide,

[87] 2-[butyl-(3-chlorobenzoyl)-amino]-5,6,7,8-tetrahydro-imidazo[1,2-a]pyridine-3-carboxylic acid [1-(2,6-dichloro-benzyl)-pyrrolidin-3-yl]-methyl-amide,

[88] 2-[butyl-(3,4-difluorobenzoyl)-amino]-5,6,7,8-tetrahydro-imidazo[1,2-a]pyridine-3-carboxylic acid 2-trifluoromethoxy-benzylamide,

[89] N-butyl-3,4-difluoro-N-{3-[4-(isopropylcarbamoylmethyl)-piperazine-1-carbonyl]-5,6,7,8-tetrahydro-imidazo[1,2-a]pyridin-2-yl}-benzamide,

[90] 2-[(3-chloro-benzoyl)-methyl-amino]-5,6,7,8-tetrahydro-imidazo[1,2-a]pyridine-3-carboxylic acid (1-methyl-3-phenyl-propyl)-amide,

[91] 2-({2-[butyl-(3-chlorobenzoyl)-amino]-5,6,7,8-tetrahydro-imidazo[1,2-a]pyridine-3-carbonyl}-amino)-3-methyl-benzyl butyrate,

[92] 2-[(3-chloro-benzoyl)-methyl-amino]-5,6,7,8-tetrahydro-imidazo[1,2-a]pyridine-3-carboxylic acid (thiophen-2-ylmethyl)-amide,

[93] 2-[butyl-(3,4-difluorobenzoyl)-amino]-5,6,7,8-tetrahydro-imidazo[1,2-a]pyridine-3-carboxylic acid (2-methyl-cyclohexyl)-amide,

[94] 2-(benzoyl-methyl-amino)-5,6,7,8-tetrahydro-imidazo[1,2-a]pyridine-3-carboxylic acid benzyl-methyl-amide,

[95] 2-[butyl-(3-chlorobenzoyl)-amino]-5,6,7,8-tetrahydro-imidazo[1,2-a]pyridine-3-carboxylic acid [2-(2,6-dichloro-benzylsulphanyl)-ethyl]-amide,

[96] 2-[butyl-(3,4-difluorobenzoyl)-amino]-5,6,7,8-tetrahydro-imidazo[1,2-a]pyridine-3-carboxylic acid (2,3-dihydro-benzo[1,4]dioxin-2-ylmethyl)-amide,

[97] 2-[(3-chlorobenzoyl)-methyl-amino]-5,6,7,8-tetrahydro-imidazo[1,2-a]pyridine-3-carboxylic acid 4-trifluoromethyl-benzylamide,

[98] N-[3-(4-benzyl-piperidine-1-carbonyl)-5,6,7,8-tetrahydro-imidazo[1,2-a]pyridin-2-yl]-N-methyl-benzamide,

[99] 2-[methyl-(naphthalene-1-carbonyl)-amino]-5,6,7,8-tetrahydro-imidazo[1,2-a]pyridine-3-carboxylic acid 2-trifluoromethoxy-benzylamide,

[100] 3-chloro-N-{3-[4-(2,5-dimethyl-phenyl)-piperazine-1-carbonyl]-5,6,7,8-tetrahydro-imidazo[1,2-a]pyridin-2-yl}-N-methyl-benzamide,

[101] 2-(benzoyl-methyl-amino)-5,6,7,8-tetrahydro-imidazo[1,2-a]pyridine-3-carboxylic acid [1-(2,6-dichlorobenzyl)-pyrrolidin-3-yl]-amide,

[102] 2-[butyl-(3,4-difluorobenzoyl)-amino]-5,6,7,8-tetrahydro-imidazo[1,2-a]pyridine-3-carboxylic acid 2-chloro-6-methyl-benzylamide,

[103] N-butyl-3-chloro-N-[3-(3,5-dimethyl-piperidine-1-carbonyl)-5,6,7,8-tetrahydro-imidazo[1,2-a]pyridin-2-yl]-benzamide,

[104] 2-({2-[(3-chlorobenzoyl)-methyl-amino]-5,6,7,8-tetrahydro-imidazo[1,2-a]pyridine-3-carbonyl}-amino)-3,3-dimethyl-butyric acid tert-butylester,

[105] 2-[methyl-(naphthalene-1-carbonyl)-amino]-5,6,7,8-tetrahydro-imidazo[1,2-a]pyridine-3-carboxylic acid (1-cyclohexyl-ethyl)-amide,

[106] 3-chloro-N-methyl-N-[3-(4-phenethyl-piperazine-1-carbonyl)-5,6,7,8-tetrahydro-imidazo[1,2-a]pyridin-2-yl]-benzamide,

[107] 2-[butyl-(3-chlorobenzoyl)-amino]-5,6,7,8-tetrahydro-imidazo[1,2-a]pyridine-3-carboxylic acid (2-phenoxy-ethyl)-amide,

[108] naphthalene-1-carboxylic acid [3-(4-benzofuran-2-ylmethyl-piperazine-1-carbonyl)-5,6,7,8-tetrahydro-imidazo[1,2-a]pyridin-2-yl]-methyl-amide,

[109] N-[3-([1,4']bipiperidinyl-1'-carbonyl)-5,6,7,8-tetrahydro-imidazo[1,2-a]pyridin-2-yl]-N-butyl-3-chlorobenzamide,

[110] N-butyl-3-chloro-N-[3-(8-fluoro-1,3,4,5-tetrahydro-pyrido[4,3-b]indole-2-carbonyl)-5,6,7,8-tetrahydro-imidazo[1,2-a]pyridin-2-yl]-benzamide,

[111] 2-[methyl-(naphthalene-1-carbonyl)-amino]-5,6,7,8-tetrahydro-imidazo[1,2-a]pyridine-3-carboxylic acid 4-dimethylamino-benzylamide,

[112] 2-[methyl-(naphthalene-1-carbonyl)-amino]-5,6,7,8-tetrahydro-imidazo[1,2-a]pyridine-3-carboxylic acid (1-methyl-3-phenyl-propyl)-amide,

[113] 2-[butyl-(3-chlorobenzoyl)-amino]-5,6,7,8-tetrahydro-imidazo[1,2-a]pyridine-3-carboxylic acid 3-methyl-benzylamide,

[114] 2-[(3-chlorobenzoyl)-methyl-amino]-5,6,7,8-tetrahydro-imidazo[1,2-a]pyridine-3-carboxylic acid (2,3-dihydro-benzo[1,4]dioxin-6-yl)-amide,

[115] naphthalene-1-carboxylic acid methyl-[3-(4-quinolin-2-ylmethyl-piperazine-1-carbonyl)-5,6,7,8-tetrahydro-imidazo[1,2-a]pyridin-2-yl]-amide,

[116] 2-[butyl-(3,4-difluorobenzoyl)-amino]-5,6,7,8-tetrahydro-imidazo[1,2-a]pyridine-3-carboxylic acid (2-cyano-ethyl)-methyl-amide,

[117] 2-(methyl-phenylacetyl-amino)-5,6,7,8-tetrahydro-imidazo[1,2-a]pyridine-3-carboxylic acid (2-p-tolyl-ethyl)-amide,

[118] 2-[butyl-(3,4-difluorobenzoyl)-amino]-5,6,7,8-tetrahydro-imidazo[1,2-a]pyridine-3-carboxylic acid [1-(4-fluoro-phenyl)-ethyl]-amide,

[119] N-butyl-N-{3-[4-(5-chloro-2-methyl-phenyl)-piperazine-1-carbonyl]-5,6,7,8-tetrahydro-imidazo[1,2-a]pyridin-2-yl}-3,4-difluoro-benzamide,

[120] 2-[butyl-(3-chlorobenzoyl)-amino]-5,6,7,8-tetrahydro-imidazo[1,2-a]pyridine-3-carboxylic acid cyclohexylamide,

[121] 2-[(3-chlorobenzoyl)-methyl-amino]-5,6,7,8-tetrahydro-imidazo[1,2-a]pyridine-3-carboxylic acid (benzo[1,3]dioxol-5-ylmethyl)-amide,

[122] 2-[butyl-(3,4-difluorobenzoyl)-amino]-5,6,7,8-tetrahydro-imidazo[1,2-a]pyridine-3-carboxylic acid 3-methoxy-benzylamide,

[123] 3-tert-butoxy-2-({2-[(3-chlorobenzoyl)-methyl-amino]-5,6,7,8-tetrahydro-imidazo[1,2-a]pyridine-3-carbonyl}-amino)-methyl butyrate,

[124] 2-[butyl-(3-chlorobenzoyl)-amino]-5,6,7,8-tetrahydro-imidazo[1,2-a]pyridine-3-carboxylic acid (2-benzyloxy-cyclohexyl)-amide,

[125] N-{3-[4-(4-fluoro-phenyl)-piperazine-1-carbonyl]-5,6,7,8-tetrahydro-imidazo[1,2-a]pyridin-2-yl}-N-methyl-benzamide,

[126] 2-(benzoyl-methyl-amino)-5,6,7,8-tetrahydro-imidazo[1,2-a]pyridine-3-carboxylic acid (naphthalen-2-ylcarbamoylmethyl)-amide,

[127] 2-[butyl-(3-chlorobenzoyl)-amino]-5,6,7,8-tetrahydro-imidazo[1,2-a]pyridine-3-carboxylic acid 4-trifluoromethoxy-benzylamide,

[128] 2-[(3-chlorobenzoyl)-methyl-amino]-5,6,7,8-tetrahydro-imidazo[1,2-a]pyridine-3-carboxylic acid (3,3-diphenyl-propyl)-amide,

[129] 2-[(3-chlorobenzoyl)-methyl-amino]-5,6,7,8-tetrahydro-imidazo[1,2-a]pyridine-3-carboxylic acid (4-benzyloxy-phenyl)-amide,

[130] N-{3-[4-(5-bromo-2-ethoxy-benzyl)-piperazine-1-carbonyl]-5,6,7,8-tetrahydro-imidazo[1,2-a]pyridin-2-yl}-N-methyl-2-phenyl-acetamide,

[131] N-[3-(3,4-dihydro-1H-isoquinoline-2-carbonyl)-5,6,7,8-tetrahydro-imidazo[1,2-a]pyridin-2-yl]-N-methyl-benzamide,

[132] 2-[butyl-(3-chlorobenzoyl)-amino]-5,6,7,8-tetrahydro-imidazo[1,2-a]pyridine-3-carboxylic acid (1-phenyl-propyl)-amide,

[133] 2-[butyl-(3-chlorobenzoyl)-amino]-5,6,7,8-tetrahydro-imidazo[1,2-a]pyridine-3-carboxylic acid 2,3-dimethyl-benzylamide,

[134] 2-[butyl-(3-chlorobenzoyl)-amino]-5,6,7,8-tetrahydro-imidazo[1,2-a]pyridine-3-carboxylic acid [2-(4-phenoxy-phenyl)-ethyl]-amide,

[135] N-{3-[4-(4-ethoxy-phenyl)-piperazine-1-carbonyl]-5,6,7,8-tetrahydro-imidazo[1,2-a]pyridin-2-yl}-N-methyl-2-phenyl-acetamide,

[136] naphthalene-1-carboxylic acid {3-[4-(2-ethyl-phenyl)-piperazine-1-carbonyl]-5,6,7,8-tetrahydro-imidazo[1,2-a]pyridin-2-yl}-methyl-amide,

[137] N-[3-(4-benzo[1,3]dioxol-5-ylmethyl-piperazine-1-carbonyl)-5,6,7,8-tetrahydro-imidazo[1,2-a]pyridin-2-yl]-N-butyl-3,4-difluoro-benzamide,

[138] N-butyl-N-{3-[4-(2,5-dimethyl-phenyl)-piperazine-1-carbonyl]-5,6,7,8-tetrahydro-imidazo[1,2-a]pyridin-2-yl}-3,4-difluoro-benzamide,

[139] 2-[methyl-(naphthalene-1-carbonyl)-amino]-5,6,7,8-tetrahydro-imidazo[1,2-a]pyridine-3-carboxylic acid [(4-chloro-phenyl)-phenyl-methyl]-amide,

[140] N-butyl-3-chloro-N-{3-[4-(4-chloro-benzyl)-piperazine-1-carbonyl]-5,6,7,8-tetrahydro-imidazo[1,2-a]pyridin-2-yl}-benzamide,

[141] 2-[butyl-(3-chlorobenzoyl)-amino]-5,6,7,8-tetrahydro-imidazo[1,2-a]pyridine-3-carboxylic acid (1-naphthalen-2-yl-ethyl)-amide,

[142] 2-(methyl-phenylacetyl-amino)-5,6,7,8-tetrahydro-imidazo[1,2-a]pyridine-3-carboxylic acid 2-fluoro-benzylamide,

[143] N-[3-(1,4-dioxa-8-aza-spiro[4.5]decane-8-carbonyl)-5,6,7,8-tetrahydro-imidazo[1,2-a]pyridin-2-yl]-N-methyl-2-phenyl-acetamide,

[144] naphthalene-1-carboxylic acid methyl-[3-(1,3,4,9-tetrahydro-b-carboline-2-carbonyl)-5,6,7,8-tetrahydro-imidazo[1,2-a]pyridin-2-yl]-amide,

[145] 2-[butyl-(3-chlorobenzoyl)-amino]-5,6,7,8-tetrahydro-imidazo[1,2-a]pyridine-3-carboxylic acid (1-methyl-3-phenyl-propyl)-amide,

[146] 3-chloro-N-methyl-N-{3-[4-(2,4,6-trimethoxy-benzyl)-piperazine-1-carbonyl]-5,6,7,8-tetrahydro-imidazo[1,2-a]pyridin-2-yl}-benzamide,

[147] 2-[butyl-(3-chlorobenzoyl)-amino]-5,6,7,8-tetrahydro-imidazo[1,2-a]pyridine-3-carboxylic acid benzhydryl-amide,

[148] naphthalene-1-carboxylic acid {3-[4-(2-chloro-phenyl)-piperazine-1-carbonyl]-5,6,7,8-tetrahydro-imidazo[1,2-a]pyridin-2-yl}-methyl-amide,

[149] 2-[butyl-(3-chlorobenzoyl)-amino]-5,6,7,8-tetrahydro-imidazo[1,2-a]pyridine-3-carboxylic acid (thiophen-2-ylmethyl)-amide,

[150] N-butyl-N-{3-[4-(4-chlorobenzyl)-piperazine-1-carbonyl]-5,6,7,8-tetrahydro-imidazo[1,2-a]pyridin-2-yl}-3,4-difluoro-benzamide,

[151] 2-(benzoyl-methyl-amino)-5,6,7,8-tetrahydro-imidazo[1,2-a]pyridine-3-carboxylic acid (3-phenyl-propyl)-amide,

[152] 2-[butyl-(3-chlorobenzoyl)-amino]-5,6,7,8-tetrahydro-imidazo[1,2-a]pyridine-3-carboxylic acid (4-tert-butyl-phenyl)-amide,

[153] 2-[butyl-(3-chlorobenzoyl)-amino]-5,6,7,8-tetrahydro-imidazo[1,2-a]pyridine-3-carboxylic acid (4-ethyl-phenyl)-amide,

[154] 2-[methyl-(naphthalene-1-carbonyl)-amino]-5,6,7,8-tetrahydro-imidazo[1,2-a]pyridine-3-carboxylic acid cyclohexylamide,

[155] 2-[methyl-(naphthalene-1-carbonyl)-amino]-5,6,7,8-tetrahydro-imidazo[1,2-a]pyridine-3-carboxylic acid [3-(methyl-phenyl-amino)-propyl]-amide

[156] 2-(methyl-phenylacetyl-amino)-5,6,7,8-tetrahydro-imidazo[1,2-a]pyridine-3-carboxylic acid [2-(3-trifluormethyl-phenyl)-ethyl]-amide,

[157] 2-(benzoyl-methyl-amino)-5,6,7,8-tetrahydro-imidazo[1,2-a]pyridine-3-carboxylic acid 4-chloro-benzylamide,

[158] 2-[butyl-(3-chlorobenzoyl)-amino]-5,6,7,8-tetrahydro-imidazo[1,2-a]pyridine-3-carboxylic acid 3-fluoro-benzylamide,

[159] 2-(methyl-phenylacetyl-amino)-5,6,7,8-tetrahydro-imidazo[1,2-a]pyridine-3-carboxylic acid p-tolylamide,

[160] 2-(benzoyl-methyl-amino)-5,6,7,8-tetrahydro-imidazo[1,2-a]pyridine-3-carboxylic acid (2-phenoxy-ethyl)-amide,

[161] 2-[butyl-(3,4-difluorobenzoyl)-amino]-5,6,7,8-tetrahydro-imidazo[1,2-a]pyridine-3-carboxylic acid (2-benzyloxy-cyclohexyl)-amide,

[162] naphthalene-1-carboxylic acid {3-[4-(4-fluoro-phenyl)-piperazine-1-carbonyl]-5,6,7,8-tetrahydro-imidazo[1,2-a]pyridin-2-yl}-methyl-amide,

[163] 2-[methyl-(naphthalene-1-carbonyl)-amino]-5,6,7,8-tetrahydro-imidazo[1,2-a]pyridine-3-carboxylic acid [2-(4-chloro-phenyl)-propyl]-amide,
[164] N-butyl-3,4-difluoro-N-[3-(thiomorpholine-4-carbonyl)-5,6,7,8-tetrahydro-imidazo[1,2-a]pyridin-2-yl]-benzamide,
[165] 2-[(3-chlorobenzoyl)-methyl-amino]-5,6,7,8-tetrahydro-imidazo[1,2-a]pyridine-3-carboxylic acid (1-adamantan-1-yl-ethyl)-amide,
[166] 2-(benzoyl-methyl-amino)-5,6,7,8-tetrahydro-imidazo[1,2-a]pyridine-3-carboxylic acid [(4-chloro-phenyl)-phenyl-methyl]-amide,
[167] N-methyl-N-{3-[4-(4-trifluoromethyl-phenyl)-piperazine-1-carbonyl]-5,6,7,8-tetrahydro-imidazo[1,2-a]pyridin-2-yl}-benzamide,
[168] 2-(methyl-phenylacetyl-amino)-5,6,7,8-tetrahydro-imidazo[1,2-a]pyridine-3-carboxylic acid (1-biphenyl-4-ylmethyl-pyrrolidin-3-yl)-methyl-amide,
[169] N-[3-(4-benzoyl-piperidine-1-carbonyl)-5,6,7,8-tetrahydro-imidazo[1,2-a]pyridin-2-yl]-3-chloro-N-methyl-benzamide,
[170] 2-[methyl-(naphthalene-1-carbonyl)-amino]-5,6,7,8-tetrahydro-imidazo[1,2-a]pyridine-3-carboxylic acid (4-tert-butyl-phenyl)-amide,
[171] 2-[butyl-(3,4-difluoro-benzoyl)-amino]-5,6,7,8-tetrahydro-imidazo[1,2-a]pyridine-3-carboxylic acid (3,3-dimethyl-butyl)-amide,
[172] 2-[butyl-(3-chlorobenzoyl)-amino]-5,6,7,8-tetrahydro-imidazo[1,2-a]pyridine-3-carboxylic acid [1-(2-bromo-4,5-dimethoxy-benzyl)-pyrrolidin-3-yl]-amide,
[173] naphthalene-1-carboxylic acid methyl-{3-[4-(3-phenyl-allyl)-piperazine-1-carbonyl]-5,6,7,8-tetrahydro-imidazo[1,2-a]pyridin-2-yl}-amide,
[174] naphthalene-1-carboxylic acid methyl-[3-(4-phenethyl-piperazine-1-carbonyl)-5,6,7,8-tetrahydro-imidazo[1,2-a]pyridin-2-yl]-amide,
[175] N-butyl-3-chloro-N-{3-[4-hydroxy-4-(3-trifluoromethyl-phenyl)-piperidine-1-carbonyl]-5,6,7,8-tetrahydro-imidazo[1,2-a]pyridin-2-yl}-benzamide,
[176] N-methyl-2-phenyl-N-{3-[4-(3-phenyl-propyl)-piperazine-1-carbonyl]-5,6,7,8-tetrahydro-imidazo[1,2-a]pyridin-2-yl}-acetamide,
[177] 2-(benzoyl-methyl-amino)-5,6,7,8-tetrahydro-imidazo[1,2-a]pyridine-3-carboxylic acid 3-fluoro-benzylamide,
[178] N-butyl-N-{3-[4-(2-chlorophenyl)-piperazine-1-carbonyl]-5,6,7,8-tetrahydro-imidazo[1,2-a]pyridin-2-yl}-3,4-difluoro-benzamide,
[179] 2-[methyl-(naphthalene-1-carbonyl)-amino]-5,6,7,8-tetrahydro-imidazo[1,2-a]pyridine-3-carboxylic acid benzo[1,3]dioxol-5-ylamide,
[180] 2-[butyl-(3,4-difluorobenzoyl)-amino]-5,6,7,8-tetrahydro-imidazo[1,2-a]pyridine-3-carboxylic acid (3,3-diphenyl-propyl)-amide,
[181] 2-[butyl-(3-chlorobenzoyl)-amino]-5,6,7,8-tetrahydro-imidazo[1,2-a]pyridine-3-carboxylic acid (2,3-dihydro-benzo[1,4]dioxin-6-yl)-amide,
[182] 2-(benzoyl-methyl-amino)-5,6,7,8-tetrahydro-imidazo[1,2-a]pyridin-3-carboxylic acid [2-(3,4-dimethoxy-phenyl)-ethyl]-amide,
[183] naphthalene-1-carboxylic acid [3-(4-benzoyl-piperidine-1-carbonyl)-5,6,7,8-tetrahydro-imidazo[1,2-a]pyridin-2-yl]-methyl-amide,
[184] 4-methyl-2-({2-[methyl-(naphthalene-1-carbonyl)-amino]-5,6,7,8-tetrahydro-imidazo[1,2-a]pyridine-3-carbonyl}-amino)-pentanoic acid tert-butylester,
[185] 2-[methyl-(naphthalene-1-carbonyl)-amino]-5,6,7,8-tetrahydro-imidazo[1,2-a]pyridine-3-carboxylic acid (4-phenoxy-phenyl)-amide,
[186] N-methyl-2-phenyl-N-[3-(4-phenyl-piperazine-1-carbonyl)-5,6,7,8-tetrahydro-imidazo[1,2-a]pyridin-2-yl]-acetamide,
[187] N-butyl-3,4-difluoro-N-{3-[4-(5-trifluoromethyl-pyridin-2-yl)-piperazine-1-carbonyl]-5,6,7,8-tetrahydro-imidazo[1,2-a]pyridin-2-yl}-benzamide,
[188] 2-(benzoyl-methyl-amino)-5,6,7,8-tetrahydro-imidazo[1,2-a]pyridine-3-carboxylic acid 2,4-dichloro-6-methyl-benzylamide,
[189] [4-({2-[butyl-(3-chlorobenzoyl)-amino]-5,6,7,8-tetrahydro-imidazo[1,2-a]pyridine-3-carbonyl}-amino)-phenyl]-carbamic acid tert-butyl ester,
[190] N-methyl-2-phenyl-N-[3-(2-pyrrolidin-1-ylmethyl-pyrrolidine-1-carbonyl)-5,6,7,8-tetrahydro-imidazo[1,2-a]pyridin-2-yl]-acetamide and
[191] 4-[2-(methyl-phenylacetyl-amino)-5,6,7,8-tetrahydro-imidazo[1,2-a]pyridine-3-carbonyl]-piperazine-1-carboxylic acid tert-butyl ester, or a corresponding salt thereof.

19. A compound according to claim 1, wherein said compound inhibits the Ca2+ ion influx in the dorsal root ganglia of rats by at least 30%, in the FLIPR assay at a concentration of 10 10 μM, in comparison with the maximum level of inhibition of the Ca2+ ion influx of capsaicin at a concentration of 10 μM.

20. A method for preparing a substituted 5,6,7,8-tetrahydro-imidazole[1,2-a]pyridin-2-ylamine compound corresponding to formula I according to claim 1, comprising the steps of:

reacting a compound corresponding to formula II,

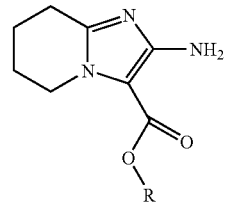

wherein R represents a linear or branched $C_{1-6}$ alkyl group, in a reaction medium in the presence of at least a reducing agent, optionally in the presence of an organic acid, with at least a compound of the general formula $R^3$—C(=O)—H, to form a compound corresponding to formula III,

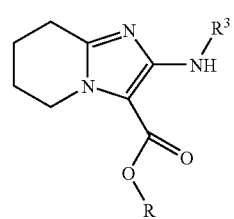

and optionally purifying and/or isolating said compound;
and reacting said compound corresponding to formula III in a reaction medium, optionally in the presence of at least a base, with at least a compound of the general formula $R^4$—C(=O)—X, wherein X represents a leaving group, or in a reaction medium in the presence of at least a coupling reagent, optionally in the presence of at least a base, with a compound of the general formula R⁴—C(=O)—OH, to form a compound corresponding to formula IV,

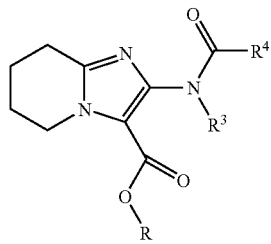

IV wherein R³ is not hydrogen, and said compound and optionally purifying and/or isolating said compound; or reacting at least a compound corresponding to formula II, wherein R represents a linear or branched C₁₋₆ alkyl group, in a reaction medium, optionally in the presence of at least a base, with at least a compound of the general formula R⁴—C(=O)—X, wherein and X represents a leaving group, or in a reaction medium in the presence of at least a coupling reagent, optionally in the presence of at least a base, with a compound of the general formula R⁴—C(=O)—OH, to form a compound corresponding to formula V,

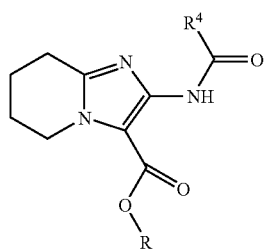

V and optionally purifying and/or isolating said compound;

and reacting at least a compound corresponding to formula V in a reaction medium in the presence of at least a base, with at least a compound of the general formula R³—X, in which R³ is not hydrogen and X represents a leaving group, preferably a halogen group, to form a compound corresponding to formula IV, and optionally purifying and/or isolating said compound;

and reacting at least a compound corresponding to formula IV, in a reaction medium in the presence of at least a base to form a compound corresponding to formula VI,

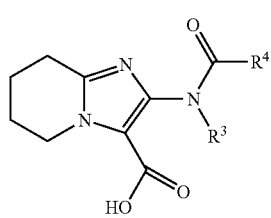

VI wherein R³ is not hydrogen, and optionally purifying and/or isolating said compound; and reacting at least a compound corresponding to formula VI, in a reaction medium in the presence of at least a coupling reagent, optionally in the presence of at least a base with at least a compound of the general formula HNR¹R², wherein R² represents hydrogen, to form a compound corresponding to formula I,

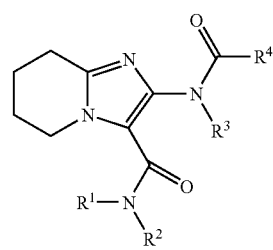

I wherein R³ is not hydrogen and R² represents hydrogen, and optionally purifying and/or isolating said compound;

and optionally reacting at least a compound corresponding to formula I, wherein R³ is not hydrogen and R² represents hydrogen, in a reaction medium in the presence of at least a base, with at least a compound of the general formula R²—X, in which R² is not hydrogen and X represents a leaving group, to form a compound corresponding to formula I, wherein R² and R³ are not hydrogen, and optionally purifying and/or isolating said compound;

or reacting at least a compound corresponding to formula VI in a reaction medium in the presence of at least a coupling reagent, optionally in the presence of at least a base, with at least a compound of the general formula HNR¹R², wherein R¹ and R² are not hydrogen, to form a compound corresponding to formula I, wherein R¹, R² and R³ are not hydrogen, and optionally purifying and/or isolating said compound.

21. The method of claim 20, wherein said organic acid is acetic acid or said leaving group is a halogen group.

22. The method of claim 20, wherein said step of reacting at least a compound corresponding to formula V or a compound corresponding to formula I in a reaction medium in the presence of at least a base includes the presence of a metal hydride salt; or the step of reacting at least a compound corresponding to formula IV in a reaction medium in the presence of at least a base, includes the presence of at least a metal hydroxide salt.

23. A method for preparing a substituted 5,6,7,8-tetrahydro-imidazole[1,2-a]pyridin-2-ylamine compound corresponding to formula I according to claim 1, comprising the steps of:

reacting a compound corresponding to formula II,

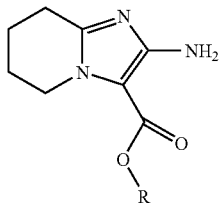

II wherein R represents a linear or branched $C_{1-6}$ alkyl group in a reaction medium, optionally in the presence of at least a base, with at least a compound of the general formula $R^4$—C(=O)—X, wherein X represents a leaving group which is optionally a halogen group, or in a reaction medium in the presence of at least a coupling reagent, optionally in the presence of at least a base with a compound of the general formula $R^4$—C(=O)—OH, to form a compound corresponding to formula IV,

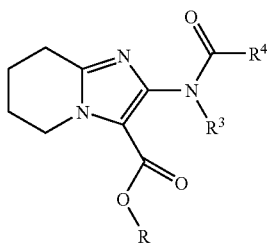

IV wherein $R^3$ is not hydrogen, and optionally purifying and/or isolating said compound, and reacting at least a compound corresponding to formula IV, in a reaction medium in the presence of at least a base, which reaction medium may optionally include a metal hydroxide salt to form a compound corresponding to formula VI,

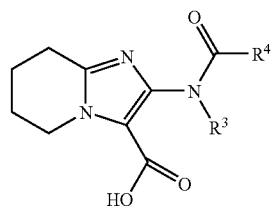

VI wherein $R^3$ is hydrogen, and optionally purifying and/or isolating said compound, and reacting at least a compound corresponding to formula VI, in a reaction medium in the presence of at least a coupling reagent, optionally in the presence of at least a base, with at least a compound of the general formula $HNR^1R^2$, to form a compound corresponding to formula I, wherein $R^3$ is hydrogen, and optionally purifying and/or isolating said compound.

24. A pharmaceutical formulation comprising at least one compound according to claim 1 and one or more physiologically acceptable auxiliary substance.

25. A method of treating or alleviating pain, said method comprising administering to a patient in need thereof a pharmaceutically effective amount of a compound according to claim 1.

* * * * *